(12) United States Patent
Karns et al.

(10) Patent No.: US 8,702,925 B2
(45) Date of Patent: Apr. 22, 2014

(54) POLAROGRAPHIC INSTRUMENT SYSTEM FOR OXYGEN AND HYDROGEN MEASUREMENT

(75) Inventors: Devin Karns, Seattle, WA (US);
Jonathan Meuser, Golden, CO (US);
Matthew Posewitz, Golden, CO (US);
Edward Dempsey, Littleton, CO (US)

(73) Assignee: Colorado School of Mines, Golden, CO (US)

( * ) Notice: Subject to any disclaimer, the term of this patent is extended or adjusted under 35 U.S.C. 154(b) by 125 days.

(21) Appl. No.: 13/108,960

(22) Filed: May 16, 2011

(65) Prior Publication Data

US 2012/0085642 A1 Apr. 12, 2012

Related U.S. Application Data

(60) Provisional application No. 61/334,977, filed on May 14, 2010.

(51) Int. Cl.
*G01N 27/26* (2006.01)
(52) U.S. Cl.
USPC .................. 204/403.01; 435/287.1; 422/68.1; 422/82.01
(58) Field of Classification Search
USPC ........................ 204/403.01–403.15, 400, 450; 435/287.1; 422/68.1, 82.01
See application file for complete search history.

(56) References Cited

U.S. PATENT DOCUMENTS

| | | | |
|---|---|---|---|
| 3,539,455 A | 11/1970 | Clark, Jr. | |
| 3,718,563 A | 2/1973 | Krull et al. | |
| 4,571,292 A | 2/1986 | Liu et al. | |
| 2009/0035856 A1* | 2/2009 | Galliher et al. | 435/383 |

OTHER PUBLICATIONS

Ananyev et al. (Biochemistry 1996, 35, 4102-4109).*
Meuser et al. (Journal of Biotechnology, 142, Jan. 15, 2009, 21-30).*
Kosourov et al. (Biotechnology and Bioengineering, vol. 78, No. 7, Jun. 30, 2002, 731-740).*
Ghirardi et al. (Proceedings of the 2000 DOE Hydrogen Program Review).*
Figueroa et al. (Journal of Photochemistry and Photobiology B: Biology 72, 2003, 35-44).*
Clark, W., "A Hydrogen Electrode Vessel", Journal of Biol. Chem., (1915), pp. 475-486.
Harrison, D.K. et al., "A Multiwire Hydrogen Electrode for In Vivo Use", Phys. Med. Biol., (1989), 34:10; pp. 1397-1412.

(Continued)

*Primary Examiner* — Jennifer Dieterle
(74) *Attorney, Agent, or Firm* — Dorsey & Whitney LLP

(57) ABSTRACT

A system for measuring hydrogen ($H_2$) and oxygen ($O_2$) including a sample system, a signal processing and system control device, at least one polarograph device and a computing device equipped with software for environmental and biological data analysis incorporating both user-defined and environmental data acquired by the signal processing and system control device. The system measures gas level or exchange (production and/or consumption) in the field or laboratory. In some embodiments, the system uses two Clark-type polarograph devices oppositely polarized with gas-specific polarographic circuits, wherein one polarograph device measures $H_2$ gas and the other measures $O_2$ gas. In some embodiments, the sample system includes an environmentally-controlled sample housing for accepting the polarograph devices and holding a test sample in a reservoir. The system measures $H_2$ or $O_2$ exchange in microbial samples, including microbial phototrophs which couple light harvesting to $H_2$ and/or $O_2$ exchange.

19 Claims, 77 Drawing Sheets

(56) References Cited

OTHER PUBLICATIONS

Kanwisher, J. 1959, "Polarographic Oxygen Electrode", Limnol. Oceanog. 4:210-217.

Gaffron, H., "Reduction of Carbon Dioxide Coupled With the Oxyhydrogen Reaction in Algae", Journal of Gen. Physiology (1942), pp. 241-267.

Meuser, J. et al., "Phenotypic Diversity of Hydrogen Production in Chlorophycean Algae Reflects Distinct Anaerobic Metabolisms", J Biotechnol., 142, (2009), pp. 21-30.

Posewitz, M. et al., Hydrogenases, Hydrogen Production, and Anoxia, Ch. 7, (2009), pp. 217-226.

Author Unknown, "Polarographic system for measurement of dissolved oxygen", [retrieved on May 5, 2011], Retrieved from the Internet: <URL: http://ruf.rice.edu/~bioslabs/studies/mitochondria/oxygraph.html>.

Author Unknown, "Oxygen Measurement: Biological Oxygen Monitoring Systems", Brochure published by Instech Laboratories, Inc., believed to be published at least as early as 1998.

* cited by examiner

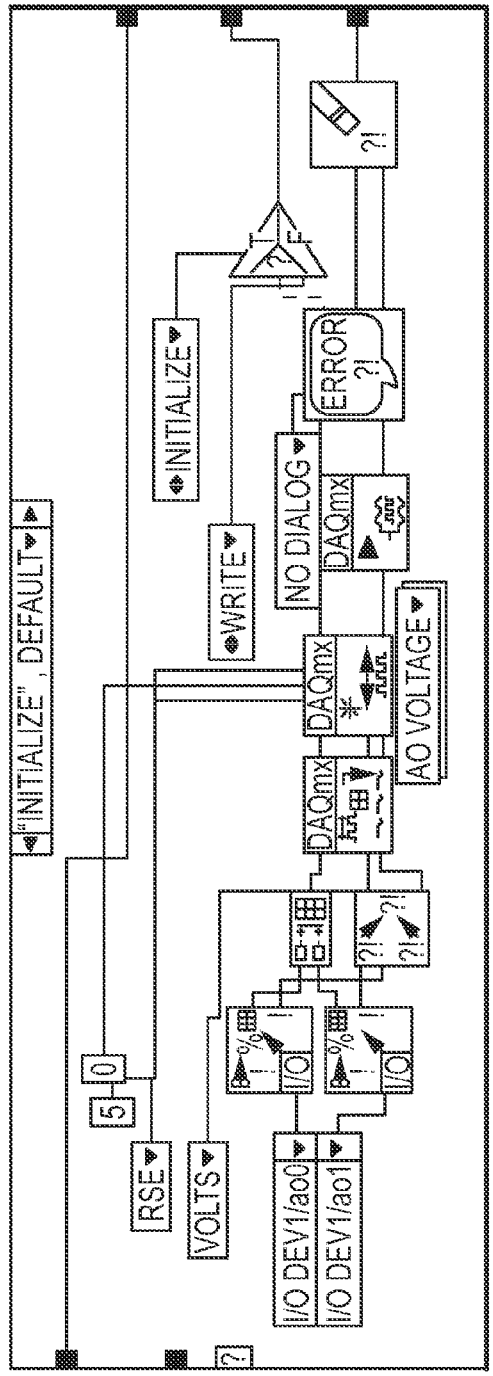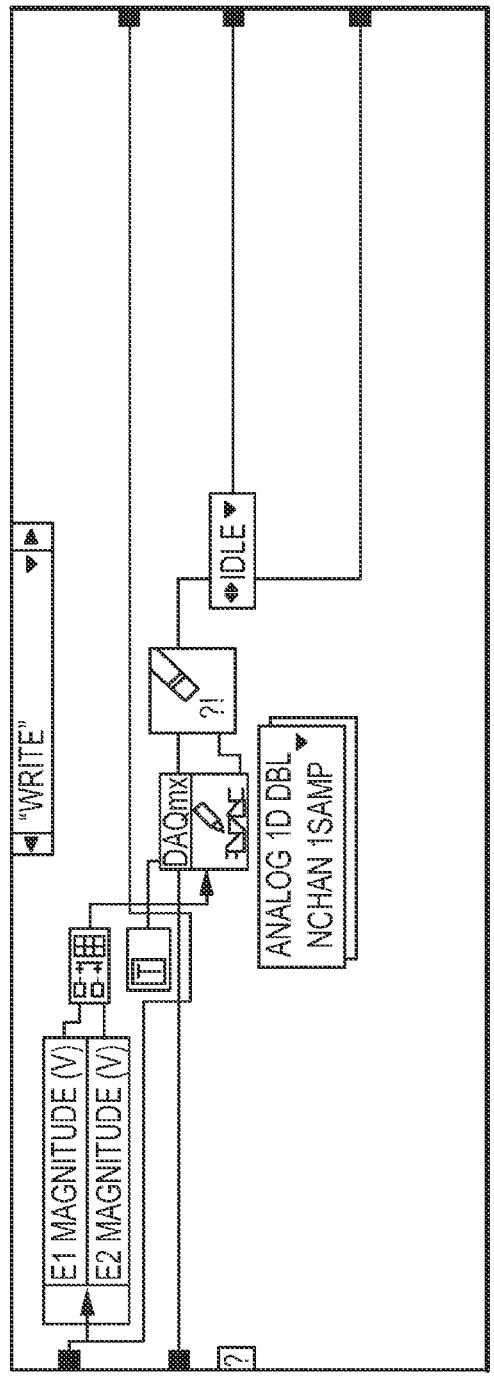
FIG. 19A
FIG. 19B

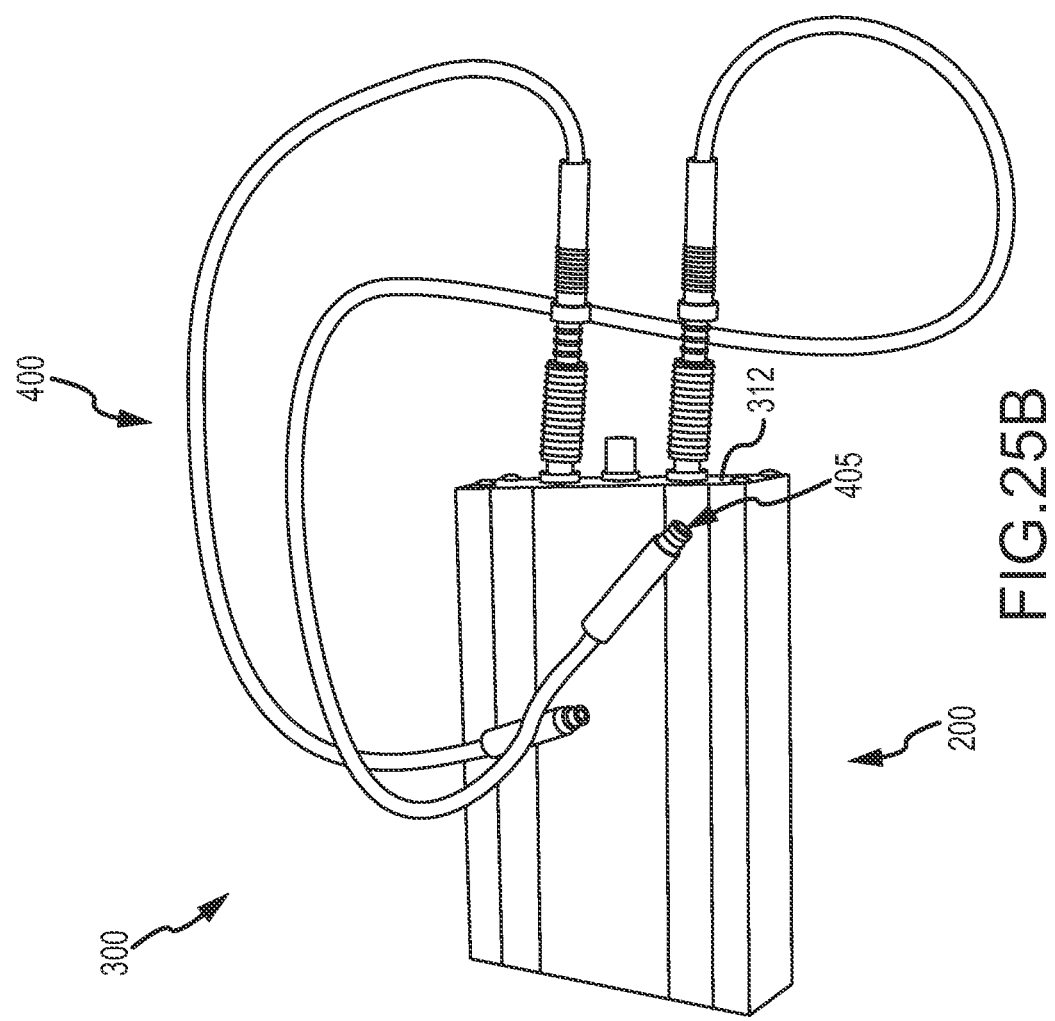

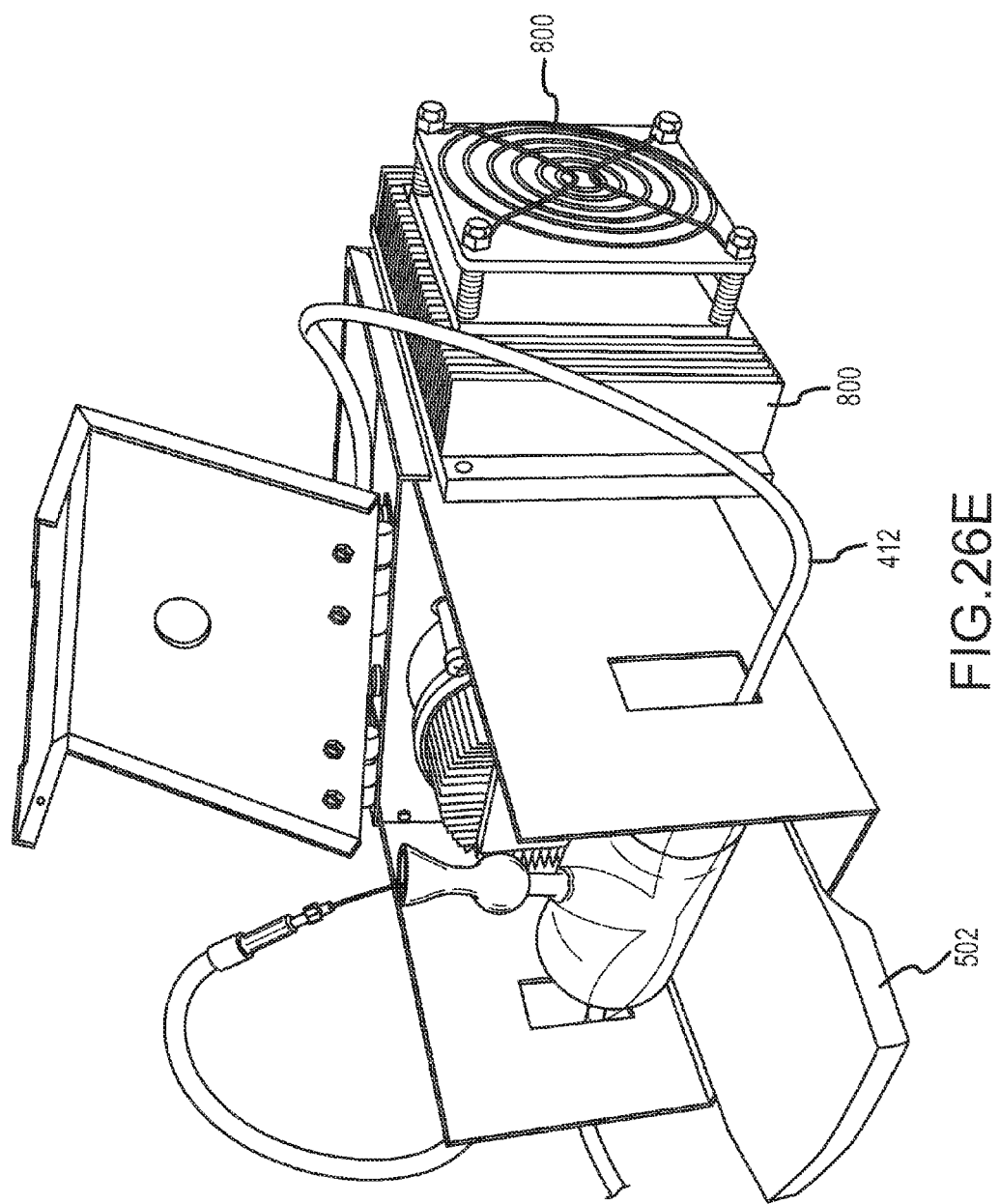

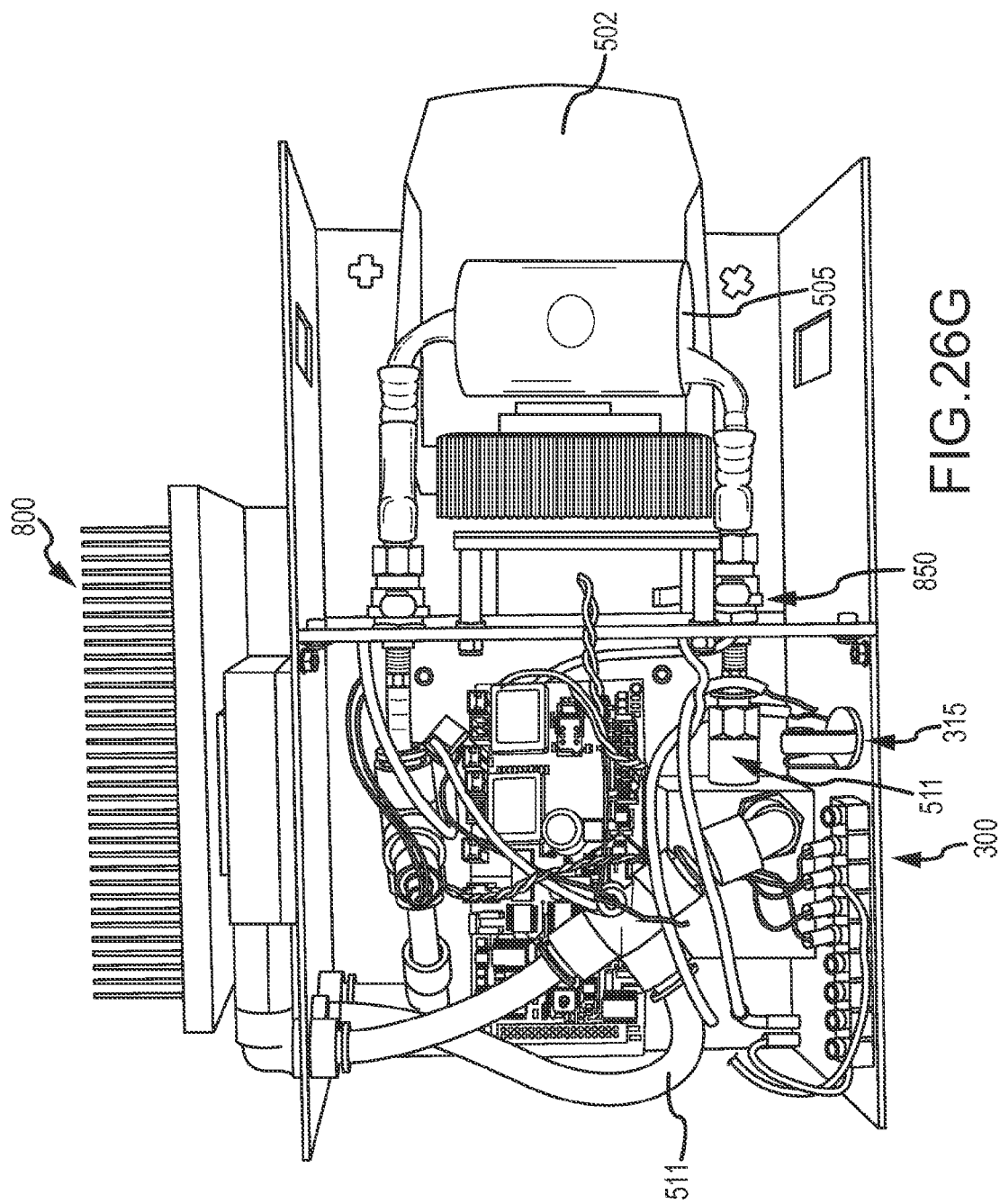

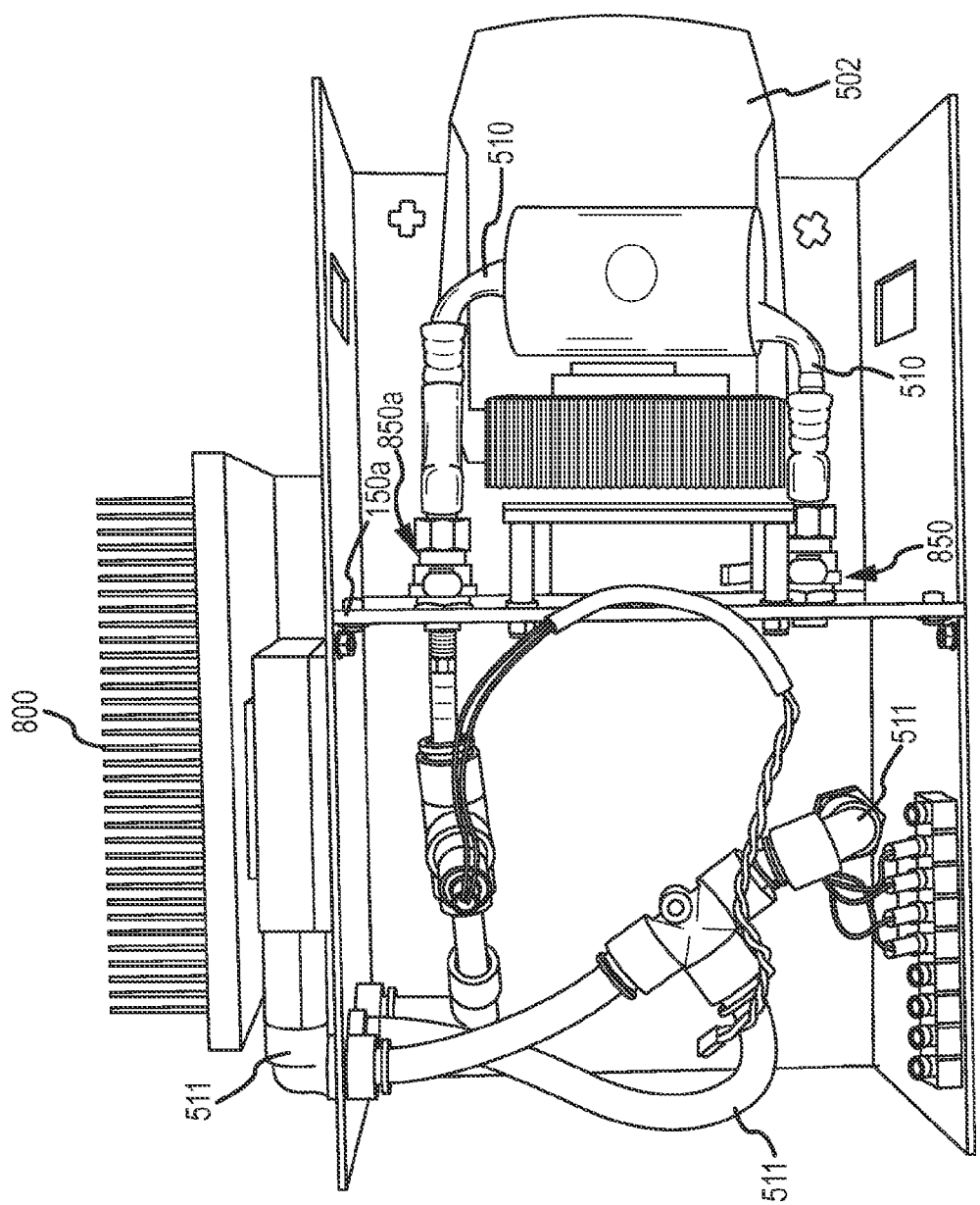

ent system including a sample system, a polarograph
POLAROGRAPHIC INSTRUMENT SYSTEM FOR OXYGEN AND HYDROGEN MEASUREMENT

CROSS REFERENCE TO RELATED APPLICATIONS

This application claims benefit under 35 U.S.C. §119(e) to U.S. Provisional Patent Application No. 61/334,977 filed May 14, 2010 entitled "A HYDROGEN AND OXYGEN SENSING CLARK-ELECTRODE SYSTEM FOR HYDROGEN-PRODUCING ALGAE CHARACTERIZATION," which is hereby incorporated by reference in its entirety.

TECHNICAL FIELD

The technology described herein is directed to a system and method for accurately determining hydrogen and oxygen levels and exchange from microorganisms and chemical gas-exchange reactions in a controlled gas, light and temperature environment.

BACKGROUND

Hydrogen ($H_2$) is the simplest energy carrier, and an important metabolite to many hydrogenase containing microorganisms. Industrial production of $H_2$ is primarily as a byproduct of petroleum refining or other types of chemical synthesis. The primary use of the approximately 3 billion cubic feet per year of $H_2$ produced in the U.S. is Haber ammonia synthesis. However, $H_2$ is also a compelling option as a fuel molecule because it is clean burning; compatible across multiple technologies (e.g. combustion, fuel cell and biological); and abundantly available from water. The low density of $H_2$ gas under ambient conditions is the primary argument against more widespread anthropogenic use. In contrast, demonstrations of its use in advanced technologies, beginning with the NASA space program, support that if $H_2$ could be produced at a significantly lower cost than traditional fuels, alternative systems do exist to couple the power of $H_2$ to human energy needs.

While $H_2$ is the most abundant chemical element in the Universe, light is clearly our most abundant energy source. While all biofuels rely on solar irradiance as the primary energy source, the efficiency of converting light energy into useable fuel requires consideration of the entire system, from source to final consumption. One promising approach is to leverage the natural ability of certain species of green algae (e.g. Chlorophyta) to produce $H_2$ coupled to photosynthetic light harvesting pathways.

A significant portion of $H_2$ assays are conducted using gas chromatography of headspace samples. Membrane inlet mass spectrometry (MIMS) systems may also be employed, but at a far greater cost than typical GC systems.

Against this backdrop, the present disclosure was developed.

SUMMARY

One aspect of the present invention involves a system for measuring oxygen and hydrogen. The system includes a polarograph system, a sample system, and a computing device. The polarograph system includes a signal processing and system control device, and a polarograph device that is communicatively coupled to the signal processing and system control device. The polarograph device includes at least one probe. The sample system includes a sample housing for containing a photobiological or biological redox reaction. The housing of the sample system is configured for receiving the at least one probe of the polarograph device. The computing device is communicatively coupled to the polarograph system, and includes a processor communicatively coupled to a memory. The processor is configured to execute instructions stored in the memory for computing oxygen and hydrogen measurements based on information received from the polarograph system. The housing of the system may further be environmentally-controlled and gas-impermeable. The system may further include at least one probe with modified or altered polarization. The system may further include varying the signal amplification of the at least one based on feedback from environmental and biological $H_2$ and $O_2$ measurements. The system may be portable. The system may further include a power source coupled to the system, an optical system operably connected to the sample system, and/or a water temperature control system, which may further include a fan, a heat sink, a water temperature system, and a water block. The water temperature control system may further include a peltier-controlled water temperature system. The at least one probe of the system may be a Clark-style electrode. The system may include a signal processing and system control device and sample system enclosed in the same housing, which may further include a wall configured to separate the signal processing and system control device and the sample system while allowing the device and sample system to remain coupled. The computing device of the system may further include an input/output device communicatively coupled to the processor and communicatively coupleable to a polarographic device to receive and transmit signals therebetween, the received signals being used by the processor to compute the oxygen and hydrogen measurements and the transmitted signals being used to control lighting, temperature or other operating parameters related to the photobiological redox reaction. The sample system of the system may further include a stir plate. The polarograph device of the system may further be configured to receive, filter and amplify signals representative of a current generated in the at least one probe coupled to the device, when the at least one probe is coupled to the sample system and exposed to a photobiological redox reaction, and the signal processing and system control device may be further configured to receive the filtered and amplified signals from the polarograph device and make the signals external to the polarograph system.

Another aspect of the present invention may be polarograph system including a polarograph device and a signal processing and system control device. The polarograph device and the signal processing and system control device may be communicatively coupled. The polarograph device may be configured to receive, filter and amplify signals representative of a current generated in one or more probes coupled to the device, when the one or more probes are coupled to the sample system and exposed to a photobiological redox reaction. The signal processing and system control device may be configured to receive the filtered and amplified signals and make the signals external to the polarograph system. The polarograph system may further include one or more probes configured to measure hydrogen in a first mode and oxygen in a second mode, and the two probes may further be oppositely polarized.

BRIEF DESCRIPTION OF THE DRAWINGS

FIG. 19A depicts an "initialize" state in LABVIEW® programming for an exemplary embodiment of an analog out case of the presently claimed system.

FIG. 19B depicts a "write" state in LABVIEW® programming for an exemplary embodiment of an analog out case of the presently claimed system.

FIGS. 25A-25D depict another embodiment of the polarograph system which may be used in a system as described herein.

DETAILED DESCRIPTION

Figure 1:
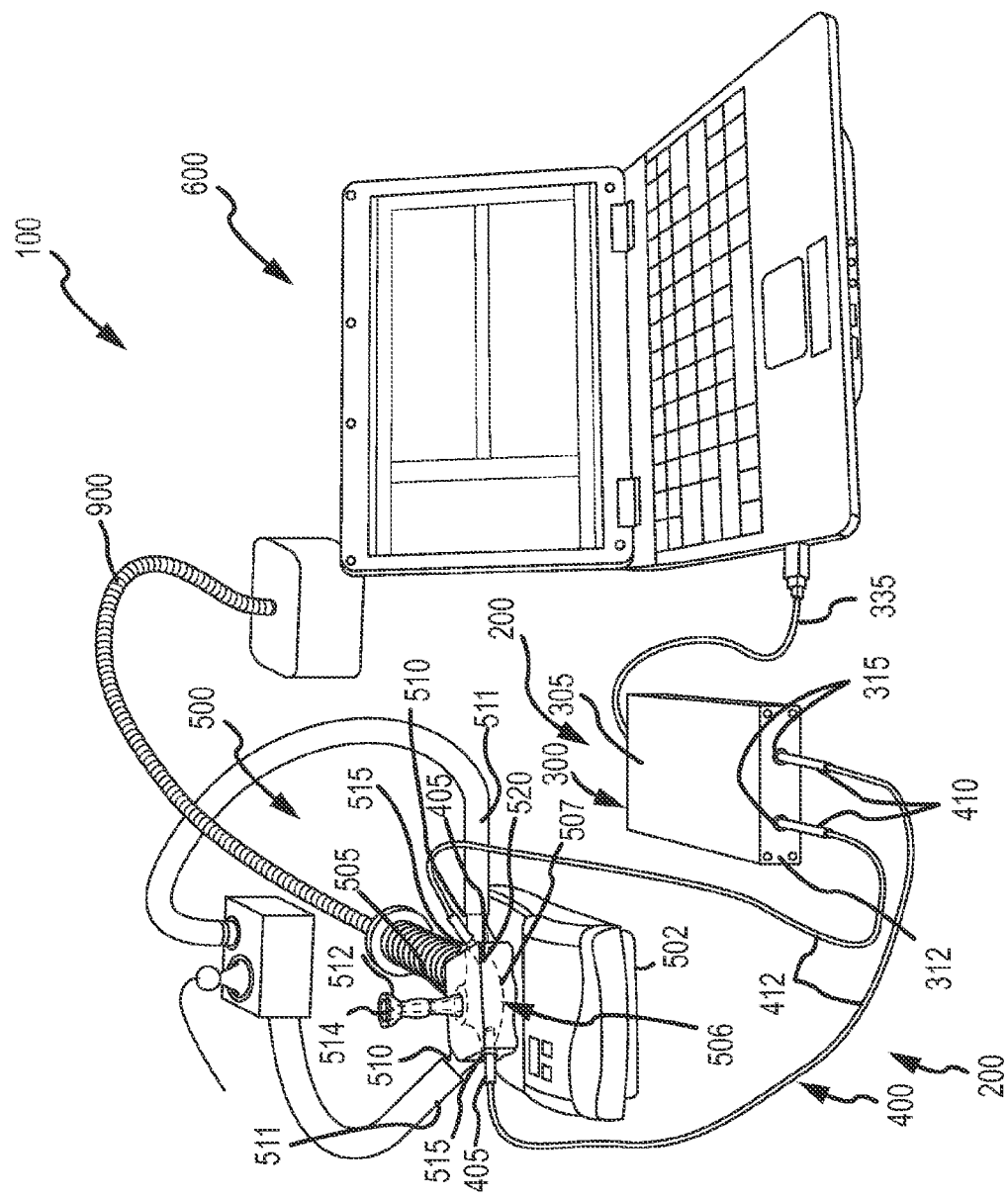
FIG. 1 depicts one embodiment of a $H_2$ and $O_2$ measurement system including a sample system, a polarograph device, a signal processing and system control device and a computing device according to aspects of the present disclosure.

Current efforts both to survey existing biological diversity of $H_2$-exchange, and to engineer photosynthetic bacteria- and microalgae-based $H_2$ producing systems that could particularly benefit from an accurate, reliable, and affordable instrument to assay microbial $H_2$ metabolism. Similarly, improvements in the existing Clark electrode system design(s) may also be applied to the assay of microbial oxygen ($O_2$) exchange for many types of experiments aimed at assessing the viability of a photosynthetic microbial fuel. An intriguing alternative to biological systems are solar chemical catalysts which can also produce $H_2$ from water and light. This is another field of research which could benefit from an affordable instrument capable of accurately assaying $H_2$ exchange under controlled conditions.

Disclosed herein is a measurement system for profiling $H_2$ and/or $O_2$ concentrations in a controlled experimental environment. In some embodiments, the system is portable, sensitive and robust, allowing the rapid characterization of $H_2$ and/or $O_2$ gas exchange by microorganisms or within natural microbial environments. In some embodiments the microorganism may be an algae or photosynthetic bacteria. The measurement system provides a more sophisticated platform to obtain new data that may substantially benefit scientific accuracy of biological $H_2$ and $O_2$ Clark-based assays, including algal $H_2$ exchange (production and/or consumption) measurements. In one embodiment, the measurement system includes a polarograph system for interrogating both $H_2$ and $O_2$ exchange from algae or photosynthetic bacteria using user-definable circuits with specific polarization and amplification respective to each gas type measurement. In some embodiments, the polarograph system may include a signal processing and system control device and a polarograph device including Clark-style $O_2$ probes, such as platinum/silver YSI 5331 Clark-style $O_2$ probes (Yellow Springs Instruments, Ohio, USA). The term "Clark-style," in relation to probes or electrodes, refers to electrodes which require voltage input to/from an external source to polarize the electrode. The system may also include a sample cell device and a computing device. In some embodiments, the measurement system includes a user-friendly software interface, for example, an interface programmed in LABVIEW®. The measurement system may also be used in the study of other biological $H_2$ and/or $O_2$ exchange processes. In some embodiments, the exchange process may be solar chemical catalysis. The measurement system allows for continuous and simultaneous $H_2$ and $O_2$ measurements and may include low cost components, thereby reducing the total cost for building and implementing the system.

Thus, herein is disclosed an accurate measurement system for both $H_2$ and $O_2$ exchange (consumption and/or production) to aid in assessing the potential of alternative solar fuel systems. Updated electronics and sample environment control, combined with commercially available Clark-type electrodes allows the measurement system to overcome the obstacles inhibiting an accelerated characterization of $H_2$-metabolizing microorganisms. This system is also beneficial in characterizing photosynthetic efficiencies in non-$H_2$ producing water-oxidizing or oxygen-consuming microbes by measurement of $O_2$ exchange.

The disclosed system may also reduce both cost and physical space required to characterize gas production from algae, compared to previous MIMS, GC, and Clark-electrode instruments. The system described herein may be small in size and have low power requirements. In some embodiments the presently described system, which may include a sample system, such as a water-jacketed glass reaction cell, probes, a signal processing and control device and a laptop, may be portable allowing it to be used in the field. In a portable embodiment, measurements may be collected without the need for an external power source, in these embodiments the signal processing and system control device may be powered by a laptop computer, connected to the signal processing and system control device, for example, by a USB cable. In other embodiments, the measurement system is configured for bench top use. This system's performance has been tested and compared to values obtained from algal control species using previous assaying methods, and the amounts and rates closely coincide. In one embodiment, linearity of $H_2$ measurements by the presently claimed system has been proven up to 9.6% $H_2$.

Figure 2:
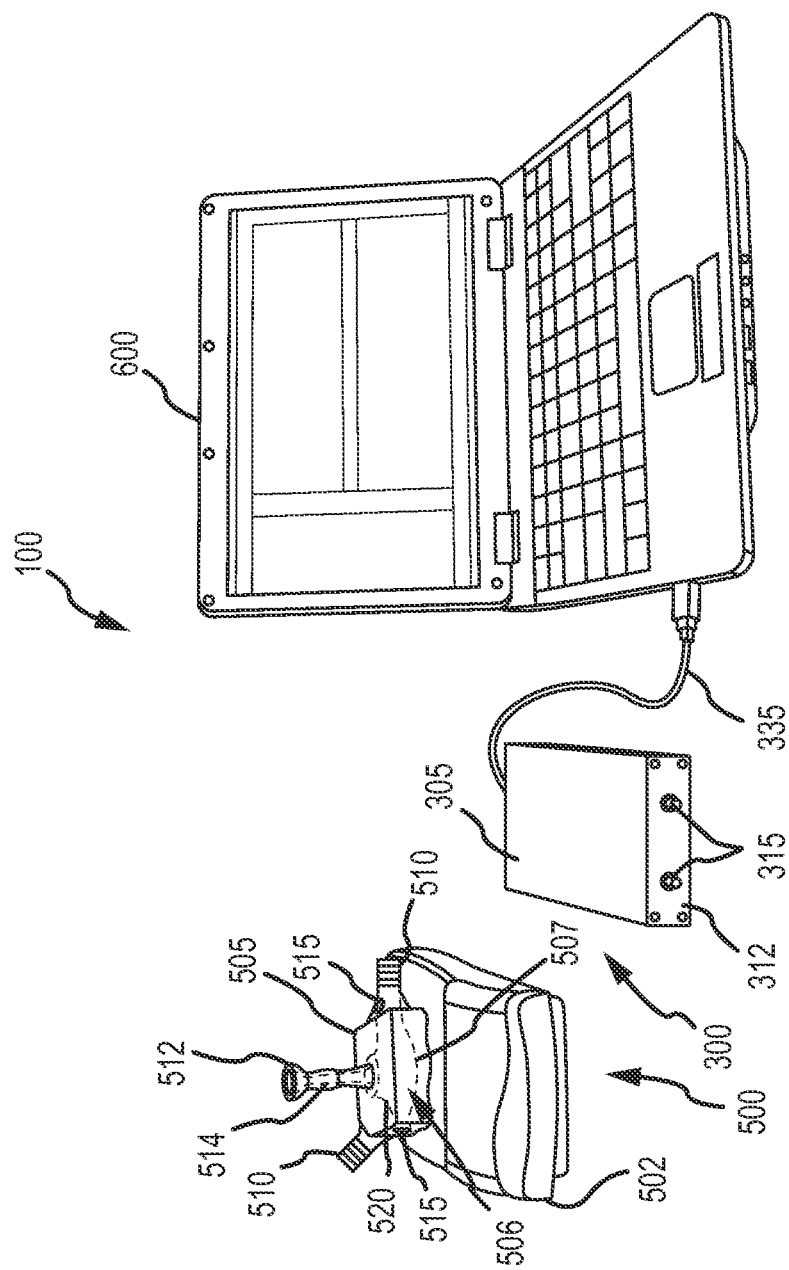
FIG. 2 depicts the system of FIG. 1, except the polarograph device is hidden for clarity.
Figure 3:
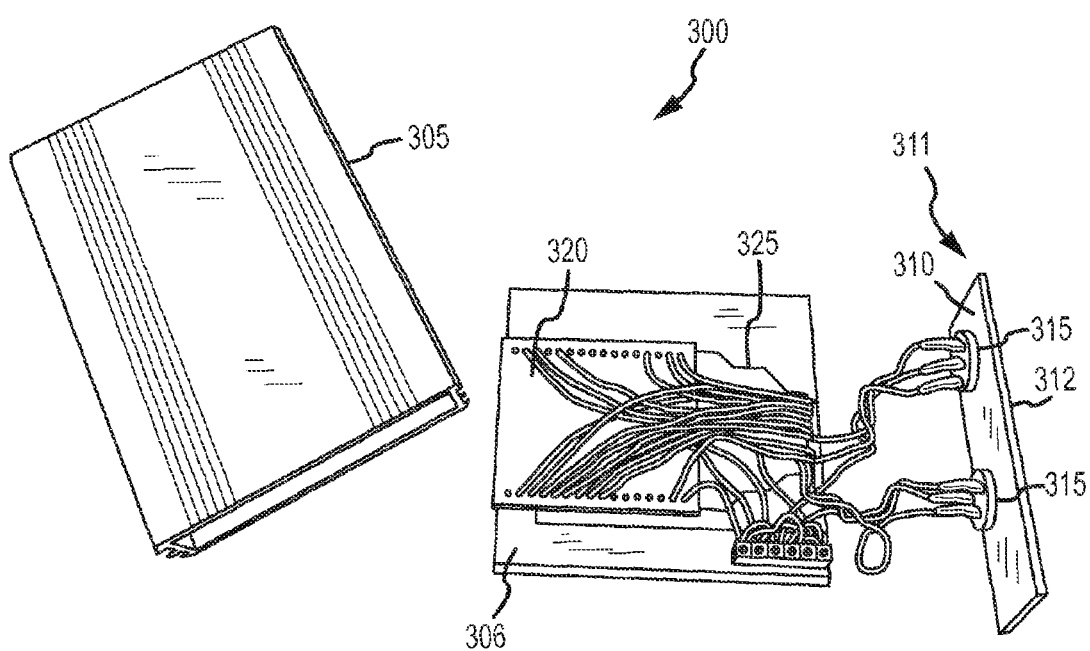
FIG. 3 depicts components of the signal processing and system control device of the system of FIGS. 1 and 2.
Figure 4:
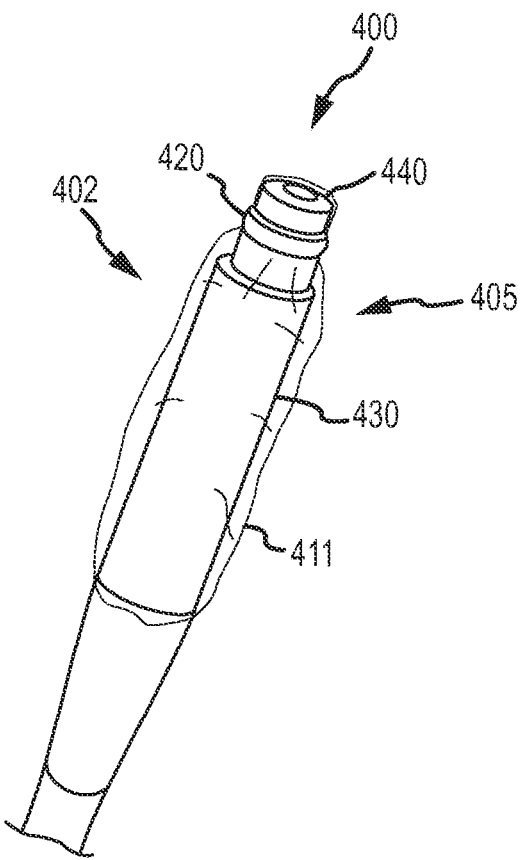
FIG. 4 depicts a proximal end of the polarograph device of the system of FIG. 1.
Figure 5:
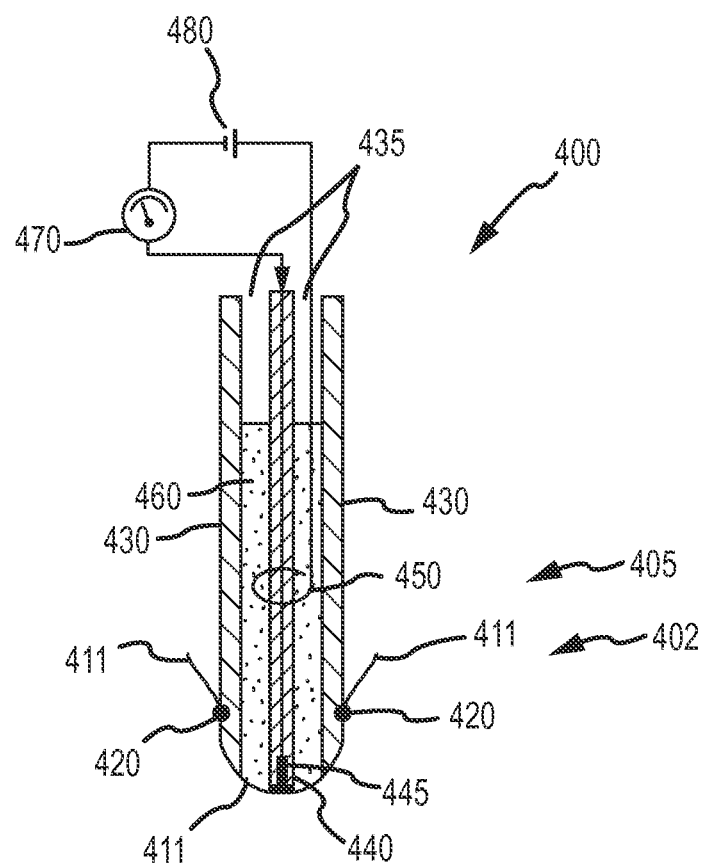
FIG. 5 depicts a cross section of polarograph device of FIG. 4.
Figure 6:
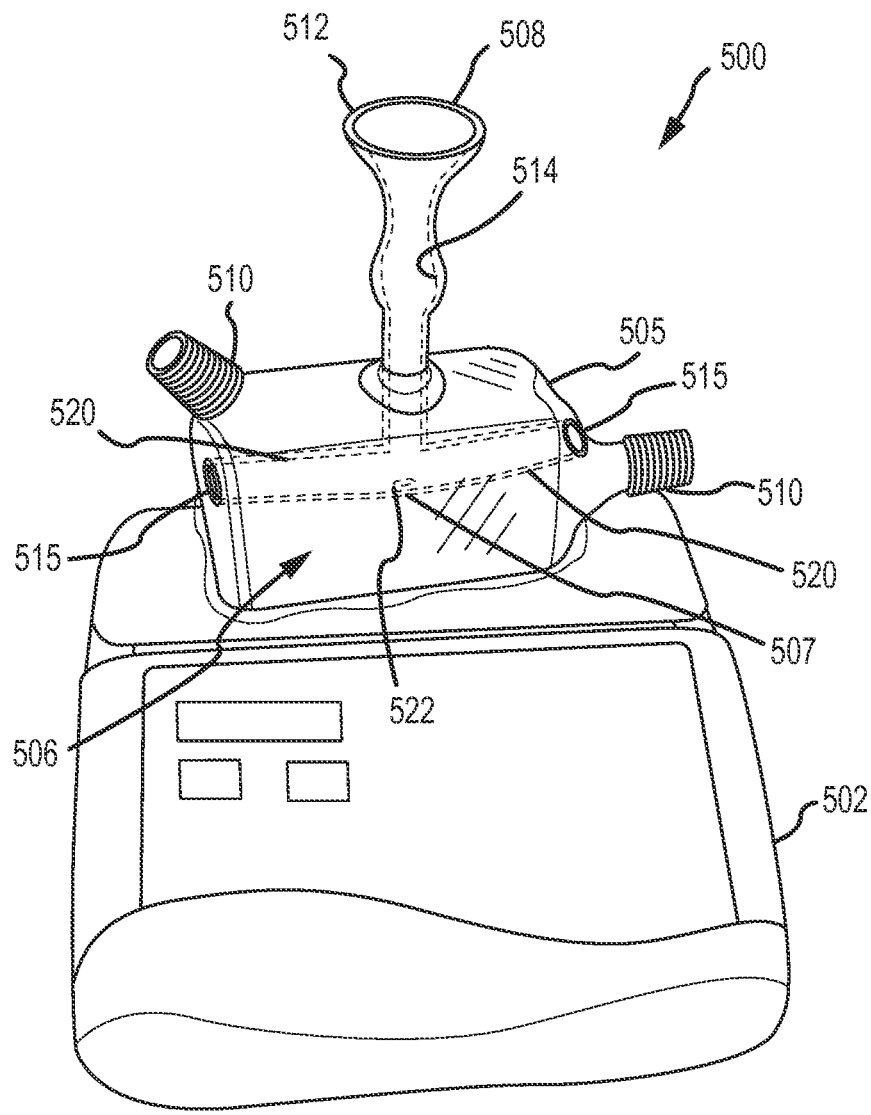
FIG. 6 depicts the sample system of the system of FIG. 1.

For a discussion of one embodiment of the system 100, reference is now made to FIGS. 1-6. FIG. 1 depicts one embodiment of the measurement system 100. In one embodiment, the system 100 includes a polarograph system 200, including a signal processing and system control device 300 and polarograph device 400. The system 100 also includes a sample system 500 and a computing device 600. FIG. 2 depicts the system of FIG. 1, except the polarograph device 400 is hidden for clarity. FIG. 3 depicts the components of the signal processing and system control device 300 of the system of FIG. 1. FIGS. 4 and 5 depict the proximal end 405 of the polarograph device 400. FIG. 6 depicts the sample system 500.

As can be understood from FIG. 3 and with reference to FIGS. 1 and 2, the polarograph system 200 includes a signal processing and system control device 300. In some embodiments, the signal processing and system control device 300 may include an enclosure or housing 305, a USB DAQ PCB 320 and signal processing and system control board or PCB 325, and a panel 310. The PCBs 320, 325 may be positioned on or mounted to a mounting plate 306. The mounting plate 306 is configured to be received in the housing 305. The panel 310 includes a PCB face 311 and an external face 312. The panel 310 also includes probe ports 315 configured to receive a distal end 410 of the polarograph device 400. The signal processing and system control device 300 houses at least some of the circuitry described in more detail below and communicatively or electronically couples the sample system 500, via the polarograph device 400, and the computing device 600 to take hydrogen and oxygen measurements.

Figure 25A:
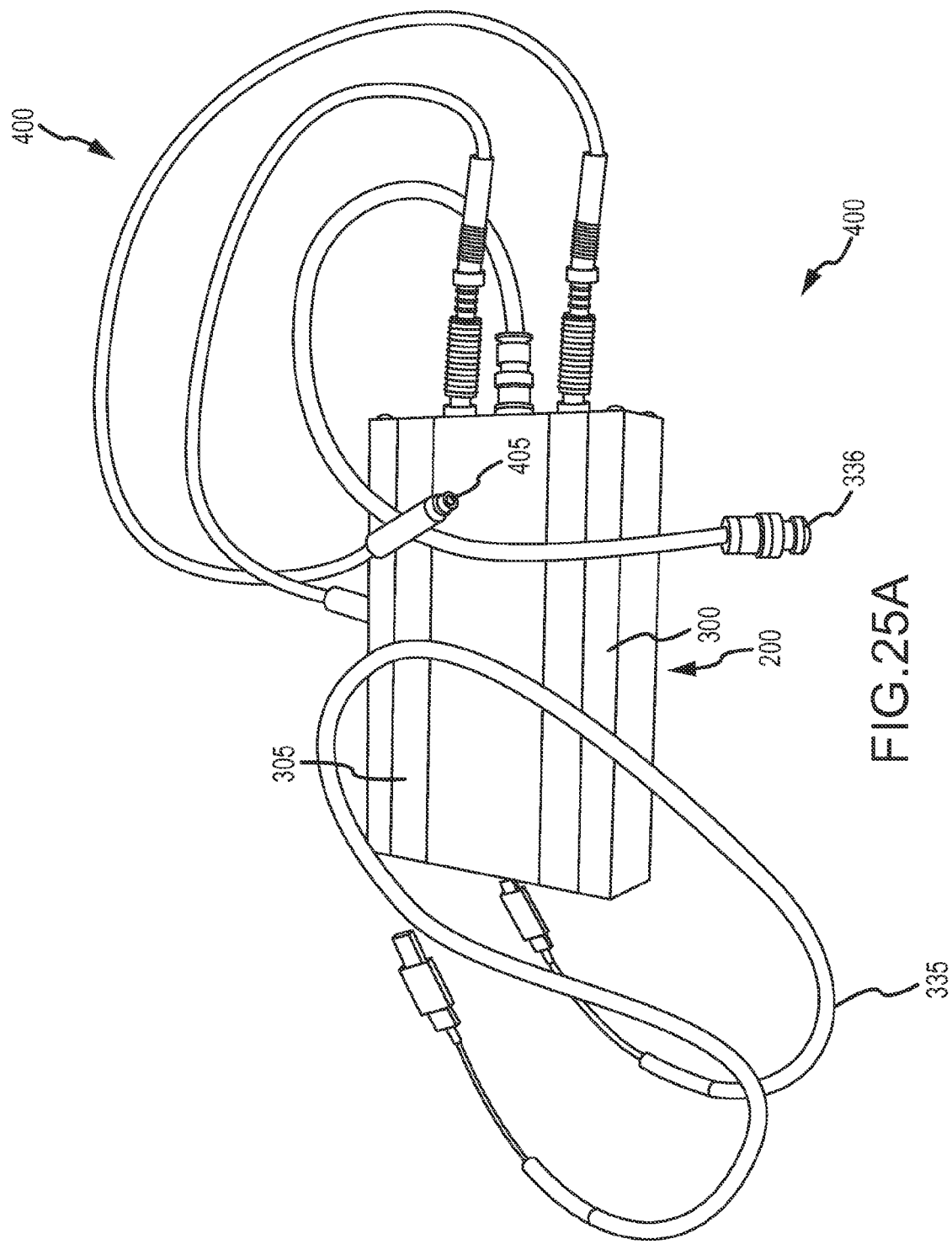
Figure 26A:
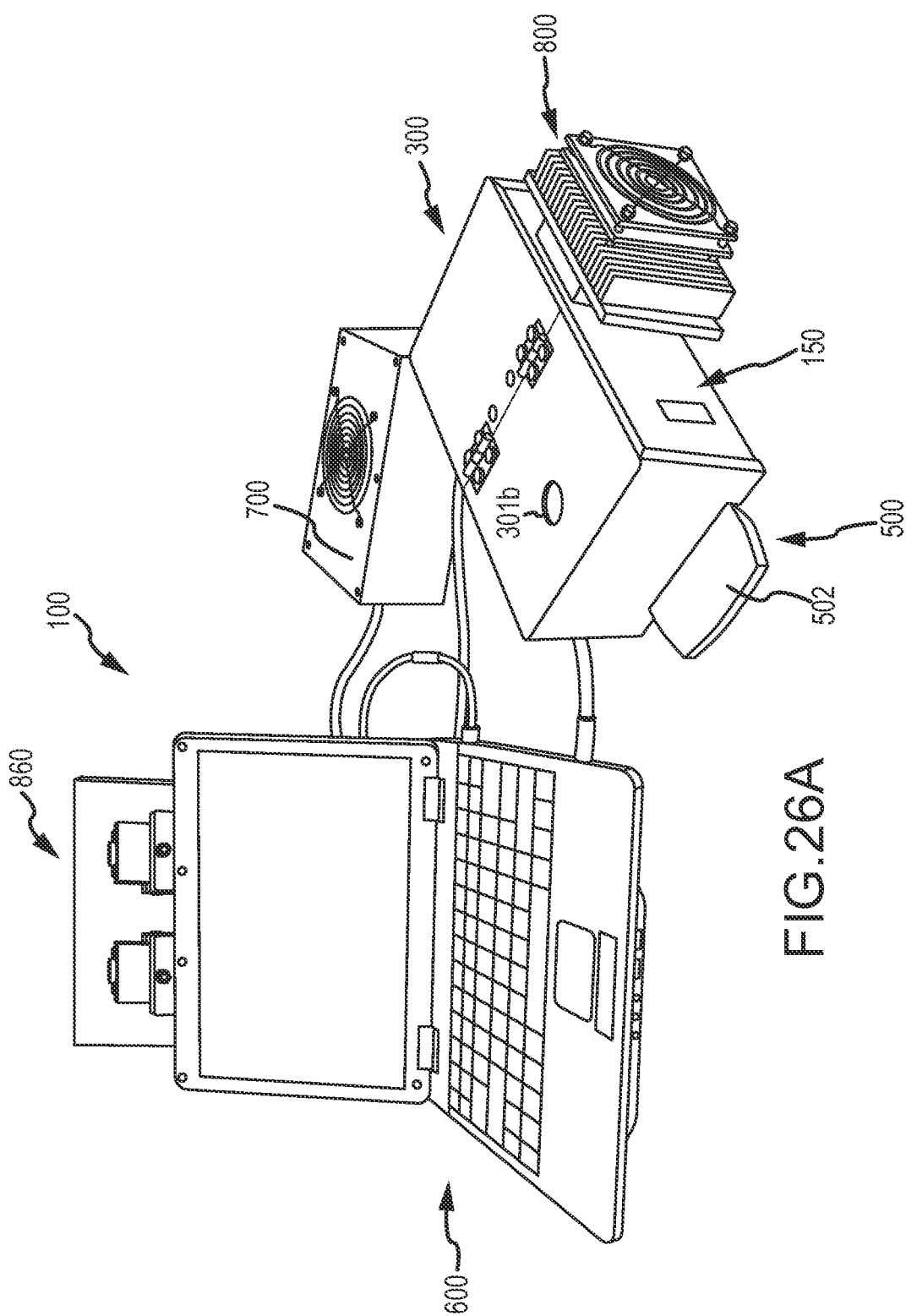
FIGS. 26A-26o depict still another embodiment of the a $H_2$ and $O_2$ measurement system including a sample cell device, a polarograph device, a signal processing and system control device and a computing device according to aspects of the present disclosure.
Figure 26B:
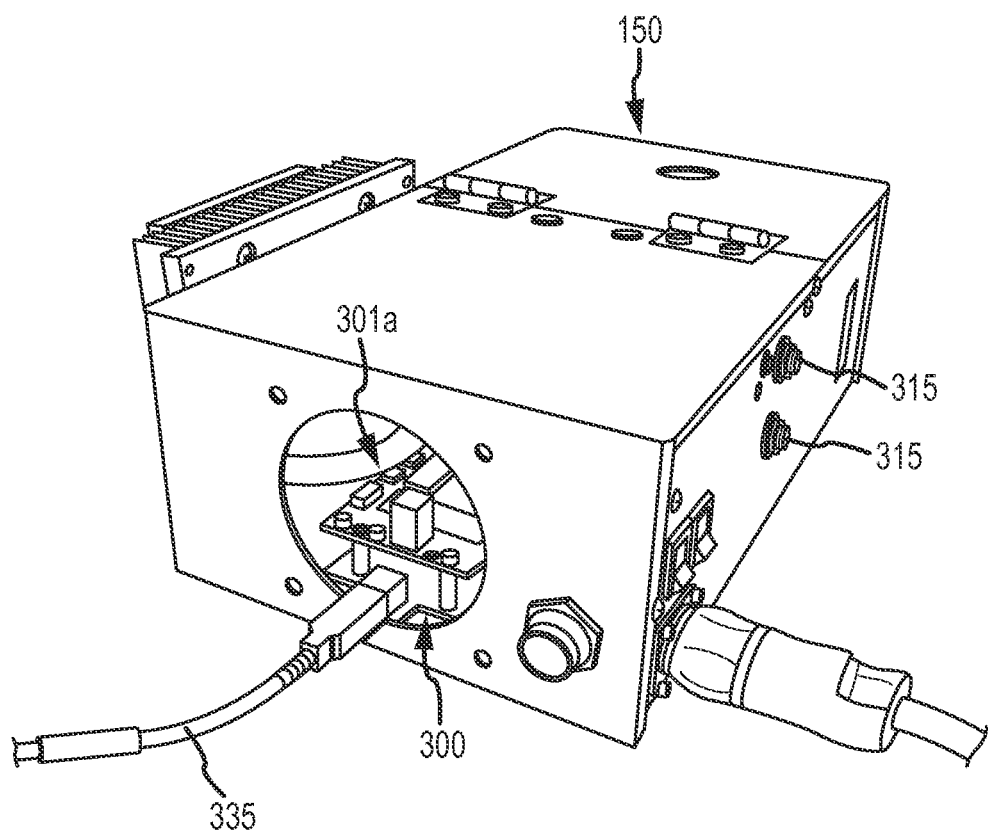
Figure 26C:
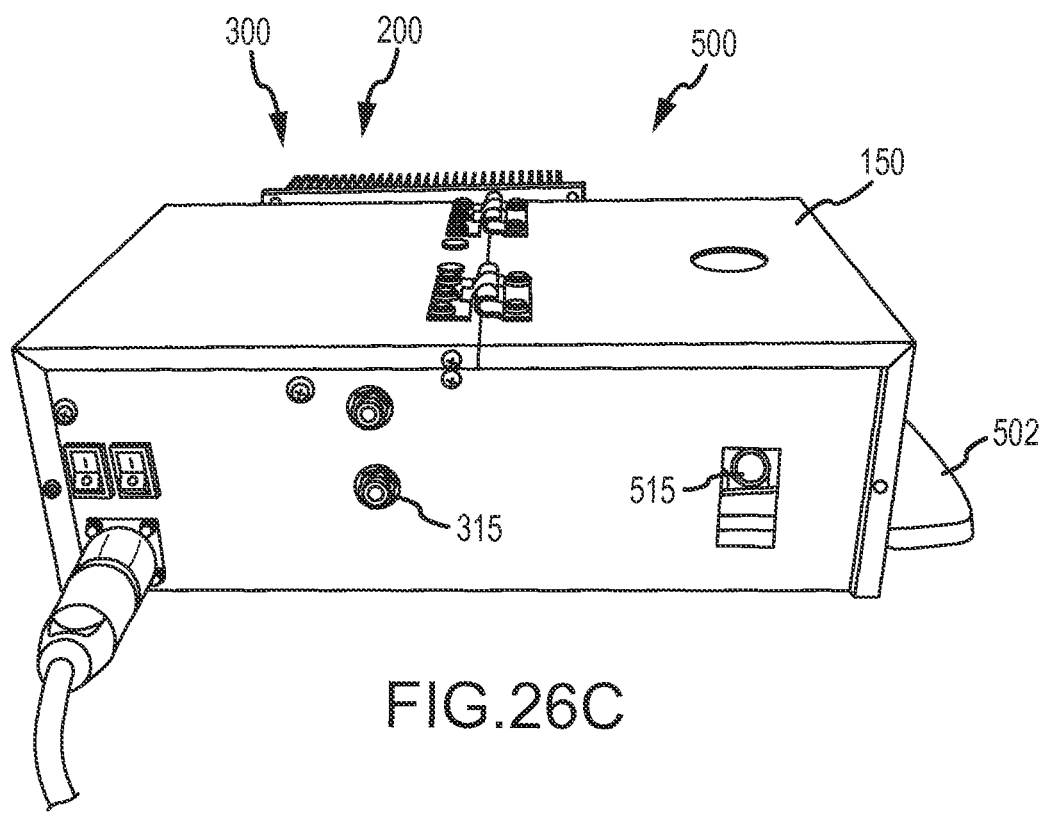

In some embodiments, as shown in FIGS. 1 and 25A, and others, the polarograph system, and more specifically, the signal processing and system control device, combines signal acquisition, filtering/conditioning, and amplification, as well as lighting control, into a relatively small (e.g., 1.18 H×4.27 W×6.3 L") anodized, extruded aluminum enclosure 305, which may be connected to a computing device 600, such as a laptop computer. In other embodiments, as shown in FIG. 26A and others, the signal processing and system control device 300 and the sample system 500 may be positioned within the same housing 150. In some embodiments, the housing 150 is still relatively small (e.g., 4.125 H×7 W×12 L").

Multiple identical $H_2/O_2$ measurement setups using this system are easily possible in a relatively small area. For simultaneous measurements, in some embodiments, the samples may be monitored by two polarograph devices; one positively polarized and the other negatively polarized. In other embodiments, the samples may be monitored by two polarograph devices where both are positively polarized and, in still other embodiments, the samples may be monitored by two polarograph devices where both are negatively polarized. Successive continuous measurements can rapidly be taken, with algal sample preparation time and the availability of species of interest being the only limiting factors in overall $H_2/O_2$ measurements. In some embodiments, the signal processing and system control device is also portable, as it may be powered solely from a universal serial bus (USB) plug, and can be toted along with a laptop for field measurements. The following considerations were taken into account during the construction of the signal processing and system control device: (1) Design functional hardware in $H_2$ and $O_2$ measurements using YSI 5331 $O_2$ probes; (a) probe current detection across a load resistor by means of a low input bias instrumentation amplifier; (b) probe polarization voltage output, allowing for both positive and negative polarization; (c) secondary gain control, using a digital potentiometer as a gain resistor on an amplifier; (d) hardware filtering to eliminate cable and component noise; (e) analog output for lighting unit control; and (f) analog output for temperature control; (2) Design software to control hardware and allow user-friendly control over experiments; (a) control of probe polarization voltage magnitude; (b) control of measurement mode ($H_2/O_2$); (c) programmatically assign lighting schema in software graphical user interface (GUI); (d) ease of input of experimental parameters; (e) calibration file acquisition for accurate 2-point scaling and calibration of acquired data; (f) signal stability indication to preserve successive experiments' accuracy; and (g) assign; (3) Design software to analyze, view, and export acquired data; (a) scaling, filtering, and calibration of acquisition files; (b) charts indicating gas amounts and production rates for both electrode acquisitions; (c) save finalized data to a separate file; and (d) option to calculate 2-point interpolation of production rates and of integrated amount produced; and (4) Validate Data; (a) prove $H_2$ linearity using multiple $H_2$ gas concentrations; (b) error analysis of input controls; and (c) perform control experiment as a comparison with previously acquired data.

As shown in FIGS. 4 and 5, and with reference to FIGS. 1 and 2, the polarograph system 200 includes a polarograph device 400. In one embodiment, the polarograph device 400 includes a proximal end 402 including a probe or electrode 405, a distal end 410 configured to be received in the probe port 315 of the signal processing and system control device 300, and a connector 412 for electrically coupling the proximal and distal ends 402, 410. In various embodiments, the probe 405 may include a body 430 having a head 440. The probe 405 may further include a membrane 411 and an O-ring 420. The membrane 410 may create a gas-permeable barrier over the head 440 and may be secured about the probe 405 by the O-ring 420. In some embodiments, the probe 405 may be a YSI Life Sciences 5331 $O_2$ probe. In other embodiments, the probe may be an $O_2$ sensor manufactured by UniSense A/S, Denmark. In other embodiments, the probe may be an $O_2$ sensor model 1302 manufactured by Warner Instruments, Hamden, Conn.

In some embodiments, the probe used with the system 100 may be based upon the Clark-electrode design. FIG. 5 depicts a cross-section of one embodiment of the probe electrode 405. The electrode 405, may be comprised of a body 430, a cathode 445, and an anode 450. The body 430 may define a head 440. The cathode 445 may be positioned proximal the head 440, and may be at least partially covered or enclosed by a membrane 411, which may be secured by an O-ring 420 positioned about the membrane 411. In some embodiments, the head 440 is fully enclosed by a membrane 411. The body 430 may define a chamber 435 configured to receive the cathode 445 and the anode 450 and an electrolyte solution 460. The anode 450 may be connected to a voltage or power supply 480, which may in turn may be connected to a galvanometer 470.

In various embodiments, the Clark-electrode may be comprised of a Pt cathode, a Ag anode, an electrolyte solution, and a gas-permeable membrane. In other embodiments, the Clark-electrode may be comprised of a Pt anode, a Ag cathode, an electrolyte solution, and a gas-permeable membrane. In various embodiments the electrolyte solution 460 may comprise a KCl solution. In various embodiments, the membrane 411 may be Teflon® or other suitable gas-permeable membrane. In some embodiments, the membrane may be coated to allow gas-specific diffusion, such as palladium coating for $H_2$ gas specific diffusion in $H_2S$ containing environments. In various other embodiments, other probes based on other electrode designs may be used with the presently described system. The probe may have a characteristic amperage at a given air pressure and oxygen concentration. In some embodiments, the probe may generate approximately 0.33 µA in open air at 760 mmHg, and approximately 1.6 µA in pure $O_2$. Prior to use, the probes may be prepared with KCl solution and a Teflon® membrane according to the YSI 5331 $O_2$ probe's accompanying documentation.

As can be understood from FIG. 1, the polarograph device 400 may interface with a signal processing and system control device 300 via the connector 412. In some embodiments, the connector may be a multi-channel phono-style plug connector. In some embodiments the connector may be a ⅛-inch or a ¼-inch phono plug. In other embodiments, the connector may be a connector that is not a phono-style connector but has a similar functionality.

In various embodiments, the probe may be designed to be used with a specific sample system, wherein the sample housing may be a gas-tight, temperature-controlled, water-jacketed sample cell, as discussed in more detail below with respect to the sample system 500. In some embodiments, any Ag/Pt-based electrode with a ¼" phono plug and similar expected current generation may be implemented with this device. Furthermore, the device can be easily modified to accommodate different plugs in other embodiments.

In some embodiments comprising a Clark-type electrode, the silver side may be polarized to a constant voltage and the platinum side may be held at ground. An electrolyte, KCl solution, may be dropped onto the head of the probe to act as an electrolyte and a permeable Teflon® or other suitable membrane may be stretched over the head to hold the KCl evenly over the active areas of the probe, as described in its accompanying documentation.

In various embodiments the probe may be able to sense $H_2$ or $O_2$, depending upon the relative polarization of the silver side to the platinum side. For example, where there is a positive polarization, metallic silver dissociates to $Ag^+$ and donates electrons to the platinum side to reduce $O_2$, as:

$$O_2 + 4e^- + 4p^+ \rightarrow 2H_2O$$

In embodiments wherein the probe has a negative polarization, $H_2$ oxidizes to $H^+$ at the Pt side and donates electrons to the Ag side (Hyman, 1961), as:

$$H_2 \rightarrow 2H^+ + 2e^-$$

In embodiments having a positive polarization or a negative polarization, there is a stoichiometric relationship between the amount of electrons flowing between the probe heads and the amount of gas in solution. Thus, the amount of $O_2$ or $H_2$ in the sample may be determined by monitoring the electrons flowing across a load resistor. Thus, the voltage is isolated and measured to determine the amount of gas present in the test sample.

According to the specifications of a YSI Life Sciences 5331 probe, at 760 mmHg in open air the probe would induce an approximately 0.33 μA $O_2$ signal, and would produce approximately 5V output without secondary gain. In some embodiments, depending upon probe quality and altitude, this can be less than 5 V. In other embodiments, the output may be between approximately 5V and approximately 10V. In various embodiments, a secondary gain may be desirable to increase calibration range and decrease error due to DAQ resolution.

In some embodiments, probe cleanliness may affect sensitivity. In various embodiments cleaning the probe with an $NH_4OH$ wash and or cleaning with sanding sheets (e.g. Micro-Mesh) may help maintain or restore probe sensitivity.

Several YSI Life Sciences $O_2$ probes have been tested. These different probes displayed differing sensitivity. For example, individual probes produced voltages in the 3-5 V range when measuring a 10% $H_2$ gas bubbling in a test sample. Thus, in various embodiments, where gain is applied, the gain may be tailored towards accommodating the maximum observed signal at 10% $H_2$ bubbling. Some probes produced values high enough to saturate the instrumentation amplifiers. Probes producing lower voltages may be chosen as benchmarks.

Thus, the presently described system may include circuitry able to detect the amount of current generated by an $O_2$ sensing probe, for example a YSI Life Sciences 5331 $O_2$ probe. This may be accomplished by allowing current to flow across a load resistor, and differentially sensing a voltage drop across that resistor by a low input bias instrumentation amplifier. Because current may be at the sub-microamp level, an integrated circuit (IC) with a 25 fA input bias current may be used in order to reduce or avoid significant signal infiltration. The resultant signal may then be amplified. In some embodiments, the signal may be amplified a second time by a second instrumentation amplifier, whose gain may be governed by a digital potentiometer. In order to help reduce or eliminate noise in the signal, capacitors may be placed across the probe's anode and cathode and/or across a load resistor. A data acquisition (DAQ) unit may provide polarization voltage, signal sensing, digital control, and power. For example, the DAQ may be a universal serial bus (USB) style DAQ, such as one made by National Instruments.

As can be understood from FIG. 6, and with reference to FIGS. 1 and 2, the measurement system 100 may also include a sample system 500. The sample system 500 is configured to monitor a test sample, such as a sample of algae. In one embodiment, the sample system 500 includes a sample housing 505 and a stir plate 502. The stir plate 502 may be any commercially or otherwise available stir plate, such as an Isotemp stir plate (Thermo Fisher Scientific Inc., Waltham, Mass.) The sample housing 505 defines a chamber 506 and a sample reservoir 507 within the chamber 506, the reservoir configured to receive a sample, such as an algae sample. The housing 505 may further include inlets/outlets 510 in fluid communication with the chamber 506 and gas inlet stem 512 and probe ports 515 defined in the housing 505 and in fluid communication with the reservoir 507. As used herein, a fluid may include, but is not limited to, a liquid or a gas. The inlet/outlets 510 may be stems (see FIG. 6) configured for coupling with tubing 511 (see FIG. 1) and, in some embodiments, the inlet/outlets 510 may be water inlet/outlets. The probe ports 515 may be fluidly connected with the sample reservoir 507 via a first channel 520 extending between each of the probe ports 515 and the reservoir 507. The gas inlet stem 512 is configured to receive a gas injection and may be fluidly connected with the sample reservoir 507 via a second channel 514 extending between the reservoir 507 and a first end 508 through the stem 512. In some embodiments, a stir bar 522 may be used to stir the contents of the sample reservoir 507. In one embodiment, the sample housing 505 may be a water jacketed, glass cell having two ports for accepting two polarograph devices and a capillary air-lock device affixed with a glass-to-glass joint (Allen Scientific Glass, Boulder, Colo., USA.)

The system 100 may also include a computing device 600. In some embodiments, the computing device 600 may include a processor and memory communicatively coupled to the processor, the processor configured to execute instructions stored in the memory. In some embodiments, the computing device 600 may be portable, such as a laptop.

Software may be designed for the presently disclosed system, which may aid in controlling various instruments, as well as receiving, recording, and analyzing signals and data generated by the system. In some embodiments, this software may be designed in LabVIEW®. In some embodiments, the software may interface with the signal processing and system control device through a graphical user interface (GUI). A GUI may aid in providing a user-friendly interface for experimental control and data analysis in the present system. In some embodiments, polarization voltage, sensing mode, gain level, and experimental parameters may be assigned on the software GUI and/or, in some embodiments, with physical controls on the unit. A GUI control may aid in decreasing the size of the presently described system and may further reduce attention towards the physical unit. In some embodiments, the presently disclosed system may include a device for providing light as discussed in more detail below with reference to the optical system 900. Thus, a lighting schema may also be programmed into the software for controlling such a light device. In some embodiments the lighting device (optical system 900) and software may allow for pulse-illuminated $H_2$-photoproduction activity measurements to be performed. In some embodiments, indicators may be provided by the software GUI. Indicators may aid in notifying the user of probe stability. Monitoring of probe stability may help provide proper scaling and translation of acquired signals and data into units that may be related to algal gas production.

In some embodiments, circuits which eliminate the need for a computer or associated software may be used. Such a circuit allows for a simple digital display of gas concentration, rates of exchange, or other elements that exist in the software described herein.

In some embodiments, the system 100 further includes a thermocouple or thermistor. Temperature compensation may require continuous sampling to dynamically account for temperature changes that may occur during an acquisition, and a thermocouple or thermistor in close proximity to the algal sample may be used. The lighting signal coming from the signal processing and system control device 300 may be a 0-5 V TTL signal or 0-5 V analog signal, and, in some embodiments, the system 100 further includes a separate lighting unit to receive the signal for light modulation. In some embodiments, the system 100 may further include a Luxeon LED (Light Emitting Diode) driver or equivalent mounted on the PCB that would provide up to 1 A to a Luxeon LED. In other embodiments, for example when the sample system 500 may be scaled up to bioreactor volumes, necessary LED control to supply the required power may be included on the PCB. In some embodiments, some or all components of the system 100 may be coupled with a Wi-Fi transmitter to facilitate multiple assaying setups about one computer.

Figure 25C:
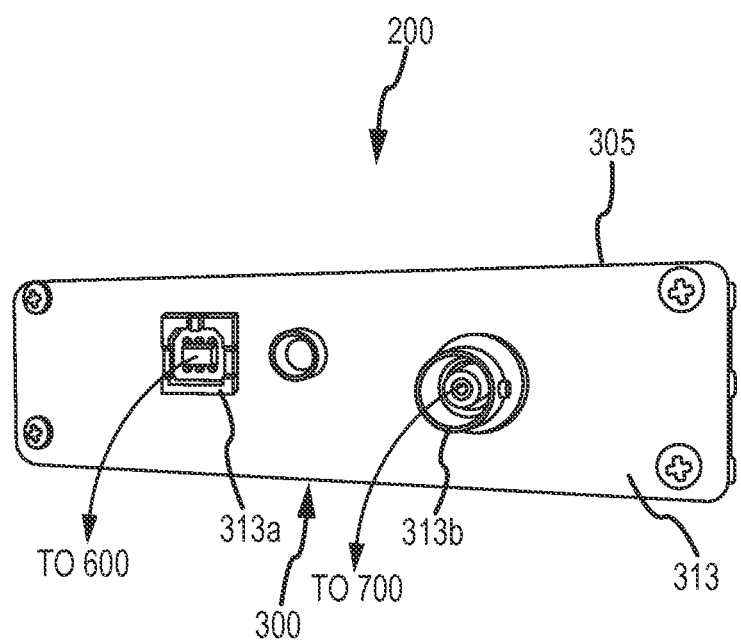
Figure 25D:
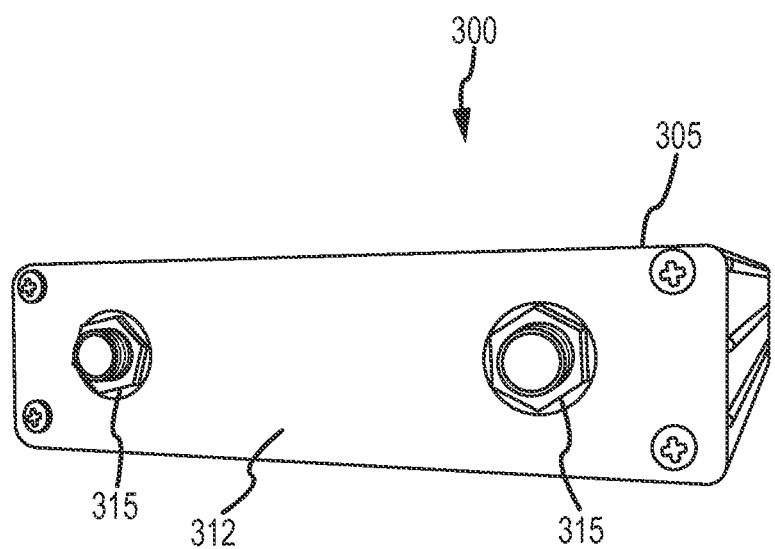

FIGS. 25A-25D depict another embodiment of the polarograph system 200 which may be used in a system 100 as described herein. FIG. 25A includes the polarograph device 400 and the signal processing and system control device 300. FIG. 25B illustrates the system 200 but the power supply connectors 335, 336 are hidden for clarity. FIGS. 25C-25D illustrate front and back panels 312, 313 of the system housing 305. The front panel 312 includes ports 315 configured to receive a distal end 410 of the polarograph device 400. The back panel 313 includes port 313a configured to receive a connector for the computing device 600 and port 313b configured to receive a connector to an external power supply 700.

Figure 26D:
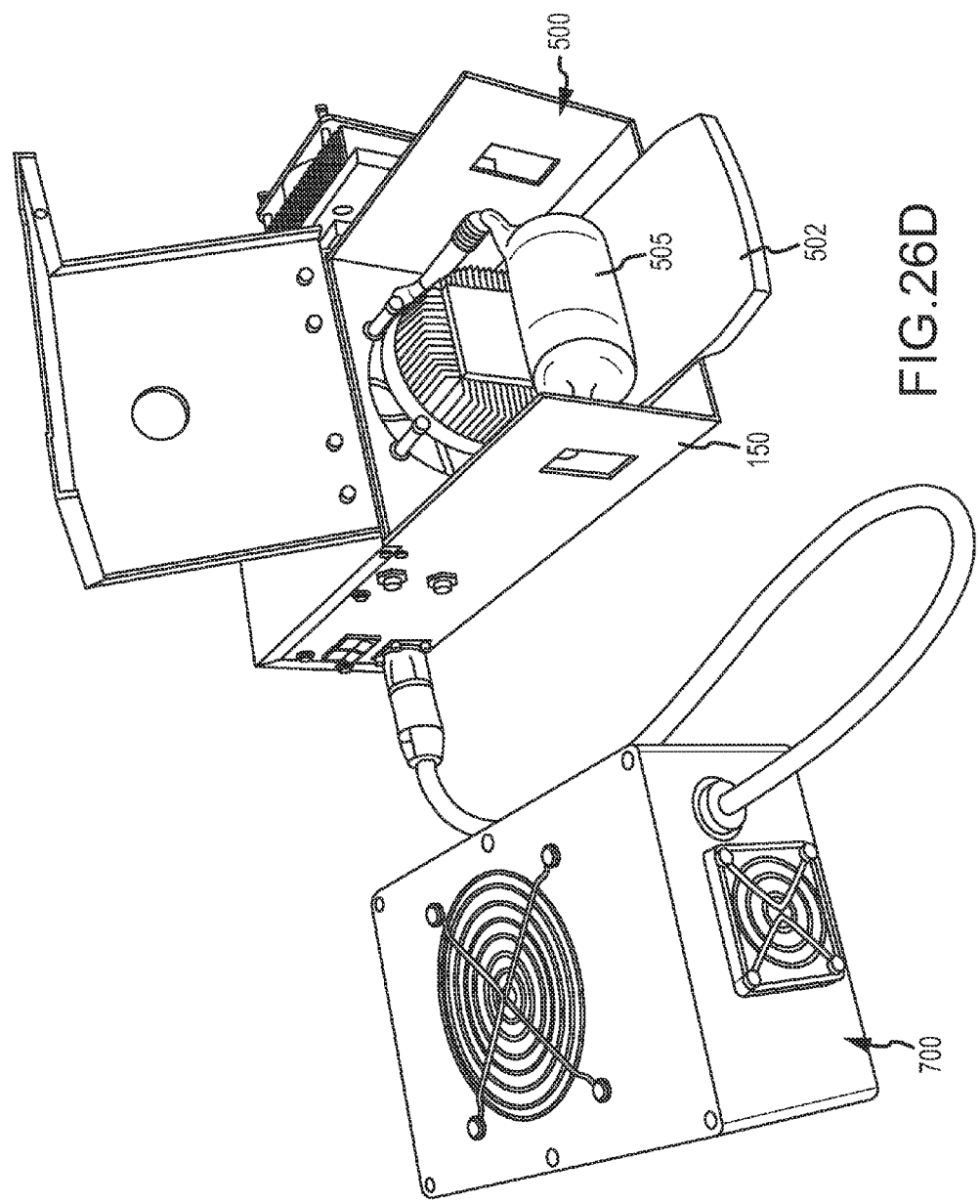
Figure 26F:
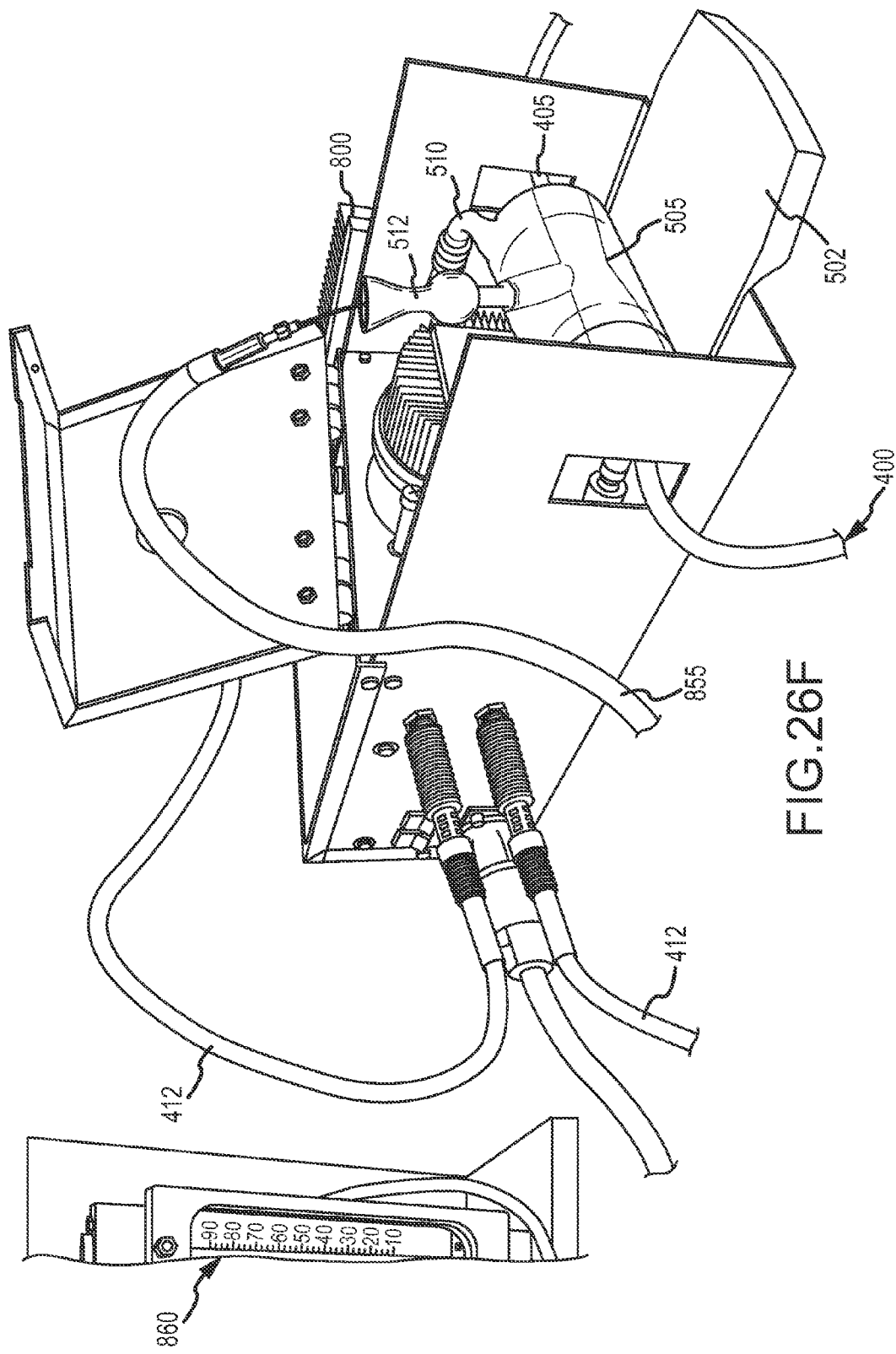
Figure 26I:
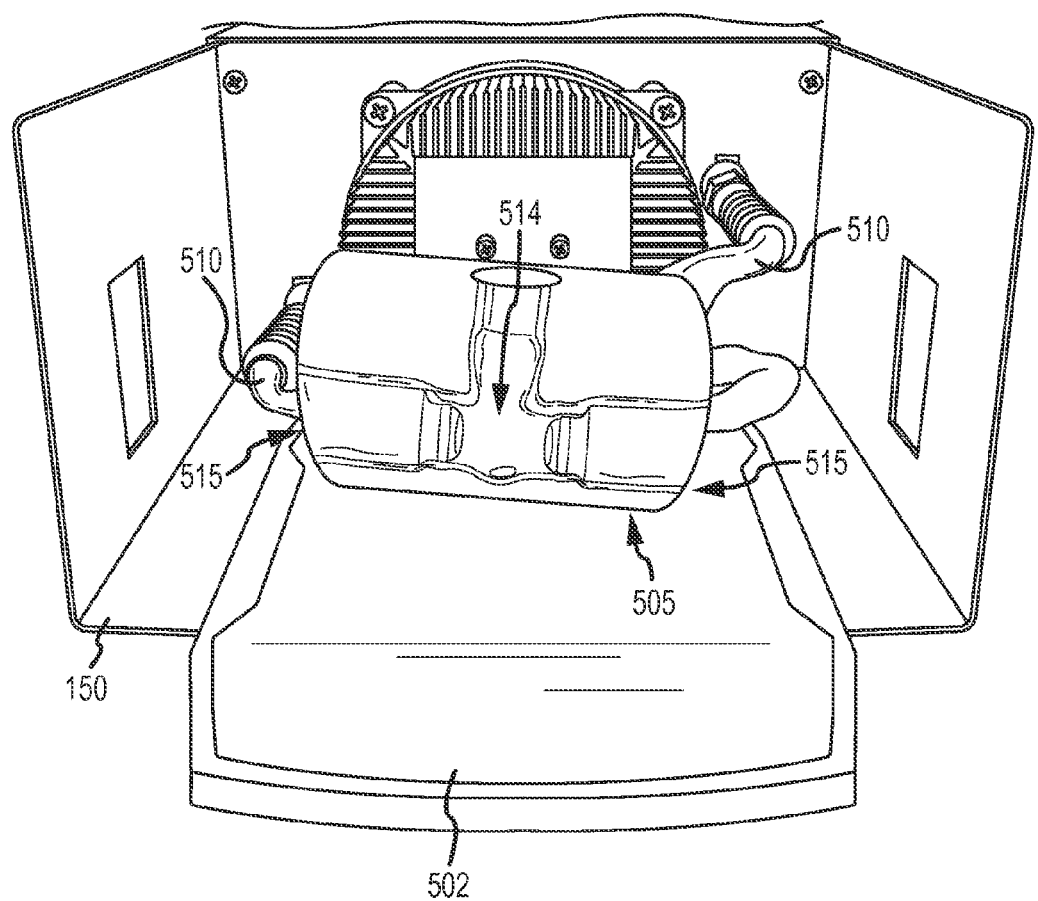
Figure 26J:
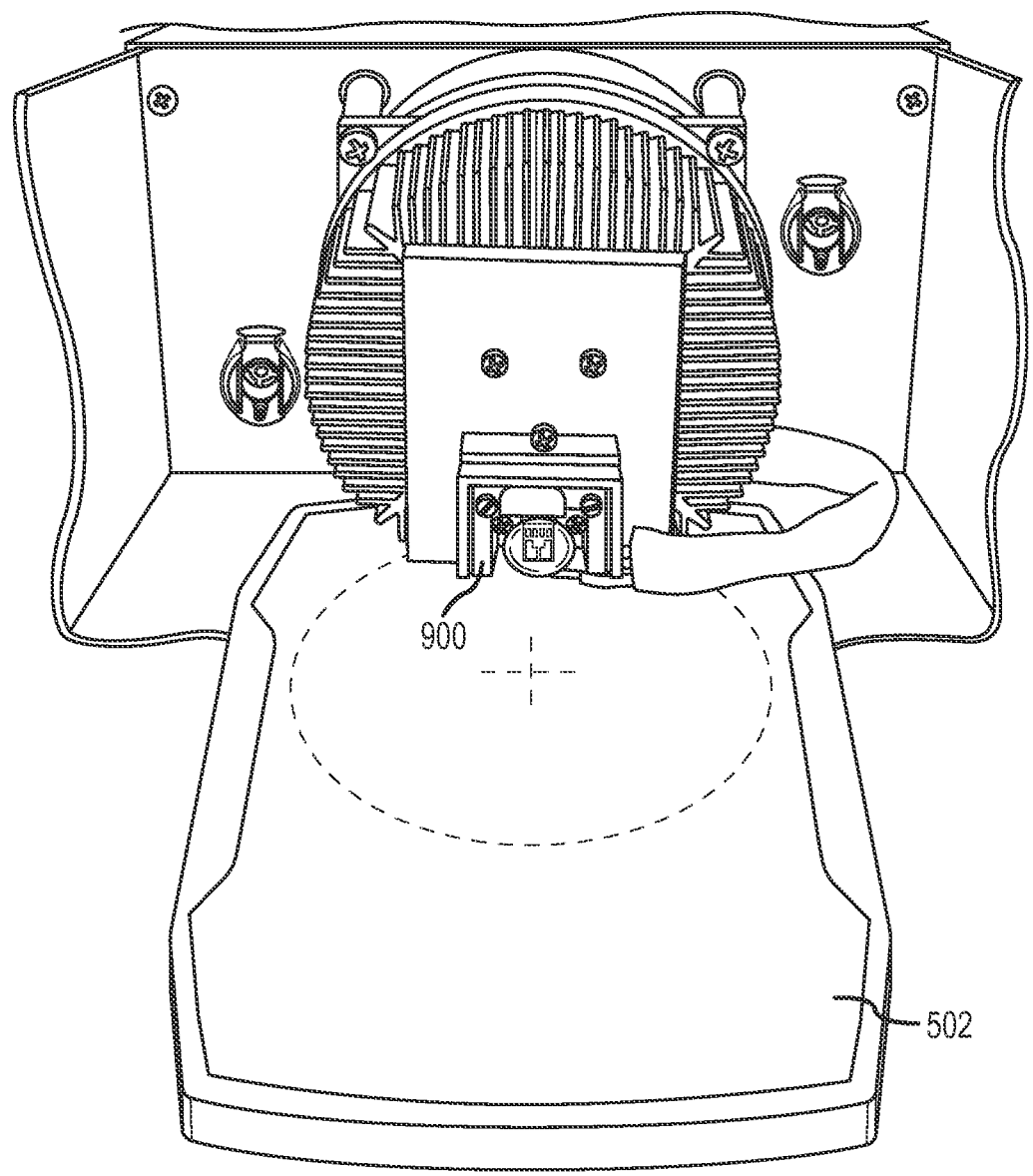
Figure 26K:
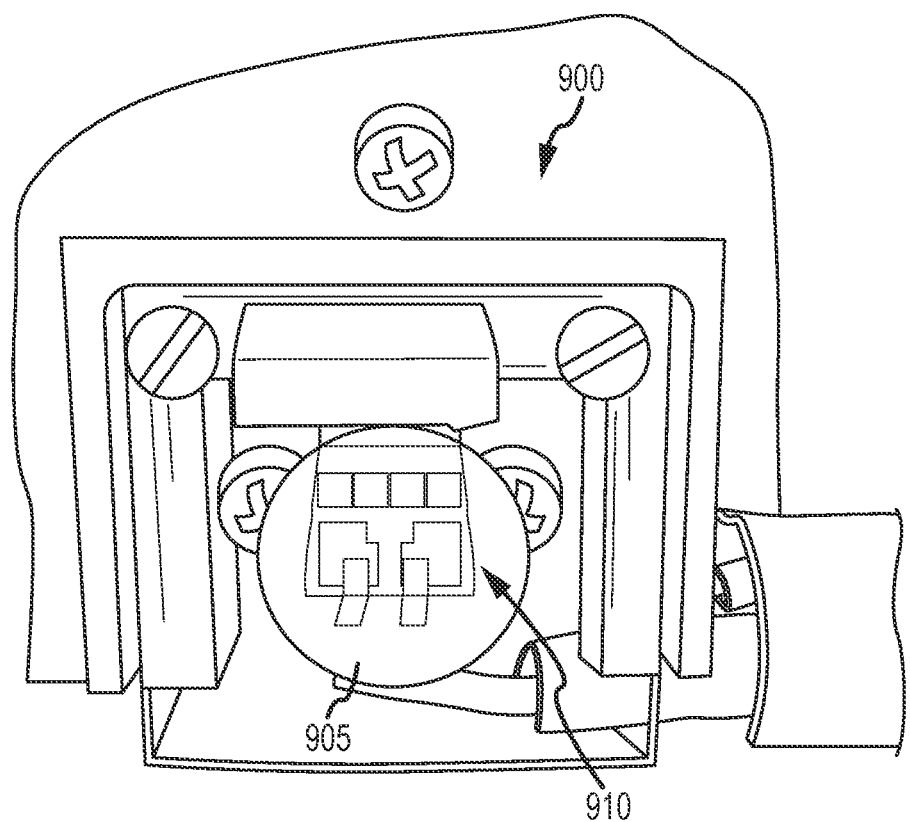
Figure 26L:
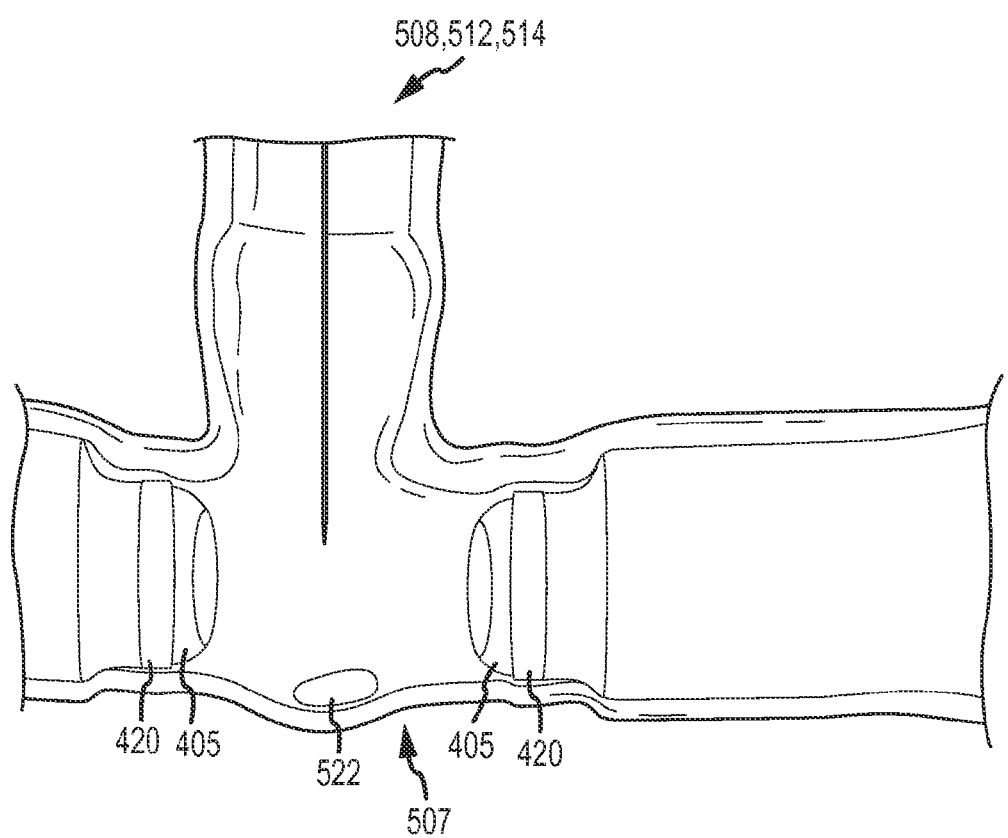
Figure 26M:
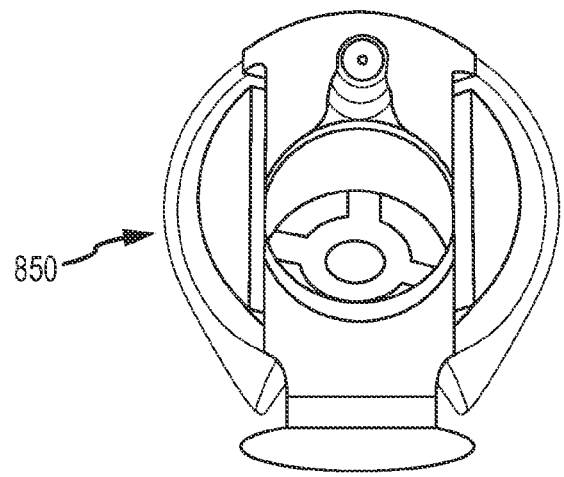
Figure 26N:
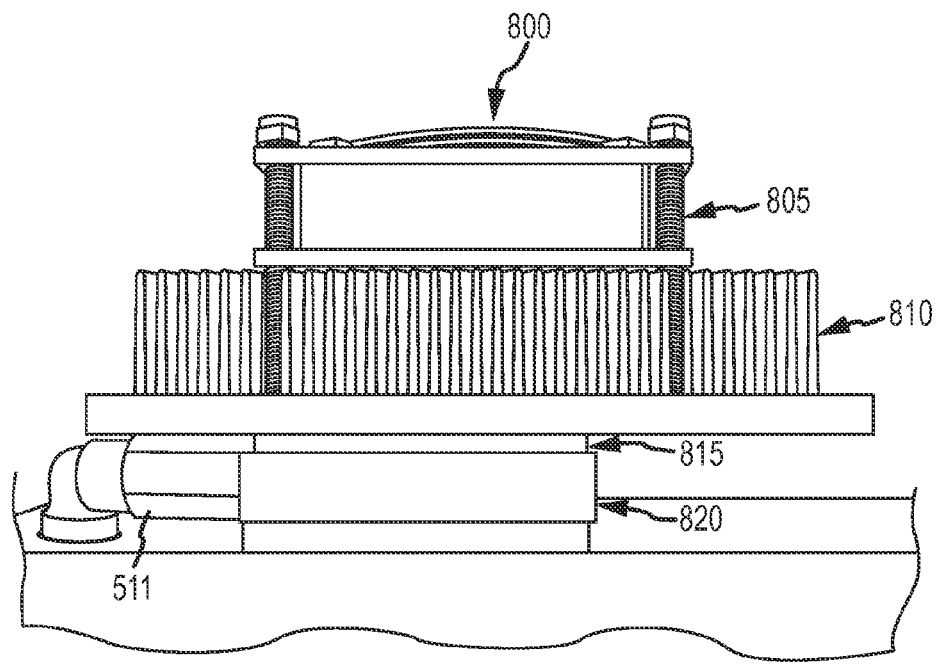
Figure 26O:
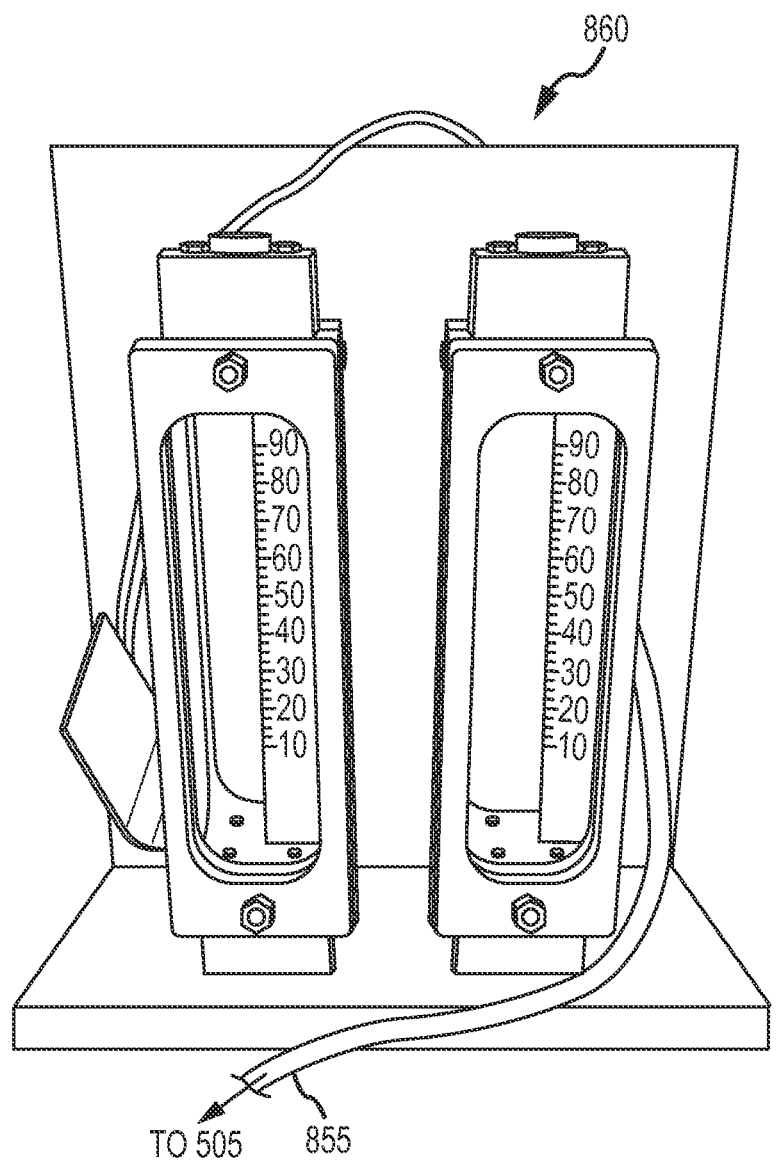

FIGS. 26A-26o depict still another embodiment of the system 100 wherein the polarograph system 200 (and more specifically, the signal processing and system control device 300) and the sample system 500 are enclosed in the same housing 150 and may be separated by a wall or partition 150a. The housing 150 may include various ports, such as port 315 and apertures 301a, 301b configured to provide airflow or receive various elements of the measurement system 100. For example, aperture 301a is configured to provide airflow to the components of the signal processing and control device 200. Aperture 301b provides a pass through in the housing 150 for the gas stem 512 of the sample system 500. The wall 150a may include various elements, ports and apertures configured to allow components of the sample system 500 and the signal processing and system control device 300 to be coupled together. For example, a quick connect fitting 850 is positioned in the wall 150a and is configured to receive a portion of the sample housing 505 via a coupling apparatus 850a. FIGS. 26A-26o include similar features as described with respect to FIGS. 1-6, which are indicated by similar numbering.

As can be understood with reference to FIG. 26A, 26D and others, in some embodiments, such as in systems with temperature control and illumination capabilities, the system may also include an external power supply 700. In some embodiments, the measurement system may derive its power for temperature control, lighting and water pumping from an Emerson/Astec switching power supply that is installed in an external enclosure that includes a cooling fan. This supply includes 24V, +12V, −12V and 5V DC supplies to power all additional components that cannot be powered from the USB supplied 5V power. This could be provided by A) DC batteries (form without power supply but instead only DC:DC converter(s)) or B) 110V power of any source to the power supply unit.

In some embodiments, as can be understood from FIGS. 26A, 26N and others, the system 100 may include a water temperature control system 800. In one embodiment, the system 800 includes a fan 805, a heat sink 810, a water temperature system 815, and a water block 820. Water is transported in and out of the water block 820 via the water lines 511. The water lines 511 are coupled to the sample system 500 via the water inlets/outlets 510. In one embodiment, the water temperature system 815 is a peltier-controlled water temperature system and is used to maintain the temperature of the sample housing 505, a water-jacketed glass cell. In some embodiments of the peltier-controlled water temperature system, the required controlling electronics are mounted on the signal processing and system control PCB 325 and controlled by the DAQ 320 via communication with the computer and software for user defined temperature control. Further, the same peltier control may be used to control the temperature of other sample cell designs by placement of the peltier and thermistor/thermocouple directly affixed to a sample cell design. In other embodiments, a compressor-based water-chiller (NesLab, Thermo Fisher) is used to maintain the temperature of a water-jacketed glass sample cell.

In some embodiments, as can be understood from FIGS. 26A, 26o and others, the system 100 may also include a gas purging apparatus 860. The gas purging apparatus 860 may provide or remove gas to the sample system 505 via a connector or tube 855. The gas apparatus allows for user-defined flow of gases with known concentrations of gases used for calibrations of the electrode response. In some embodiments this can be accomplished by manual valves as is common to the art, while in other embodiments digitally-controlled or computer controlled gas valves may be used and coupled to auto-calibration software-defined procedures. Typically, a compressed gas tank containing 5% $H_2$ gas solution with a balance of Ar or $N_2$ is used for calibration of an electrode polarized for $H_2$ measurement and either 10% $O_2$ with inert gas balance or air is used for $O_2$ electrode calibration. Gases are introduced to the sample cell via similar luer-style needles like those available from Scientific Glass Engineering (SGE); Ringwood, 3134 Australia); which may also be used to introduce experimental samples to the sample cell.

In some embodiments, as can be understood from FIGS. 26J-K and others, the system 100 may include an optical system 900. The optical system may include a lens 905 and a light source 910, such as an LED light source. The optical system 900 is configured to illuminate the sample system 500, as shown in FIG. 26D and others.

In use, and as shown in FIGS. 1 and 2, with reference to FIGS. 3-6, the various elements of the system 100 may be coupled together as described elsewhere herein to measure $H_2$ and $O_2$ in a sample. The signal processing and system control device 300 may be electrically coupled to the computing device 600 with a cable 335, for example a USB cable. The distal ends 410 of the polarograph device 400 are coupled to the signal processing and system control device 300 and received in the ports 315 of the signal processing and system control device 300. The sample may be placed in the sample reservoir of the sample cell 500 prior to coupling the polarograph device 400 to the sample cell 500. The polarograph device 400 is then coupled to the sample cell 500 and more specifically, the proximal ends 405 of the polarograph device 400, which include the probes 402, are received in the sample housing 505 of the sample cell 500. Tubing 511 may be attached to inlets/outlets 510 and water may be introduced to the system. Once the sample is in the reservoir, the appropriate gas and fluids are flowing, the stir plate is turned on and the sample is stirred with the stir bar.

Measurements are taken via the probes and the data or information is sent to the computing device via the signal processing and system control device for analysis.

Figure 9A:
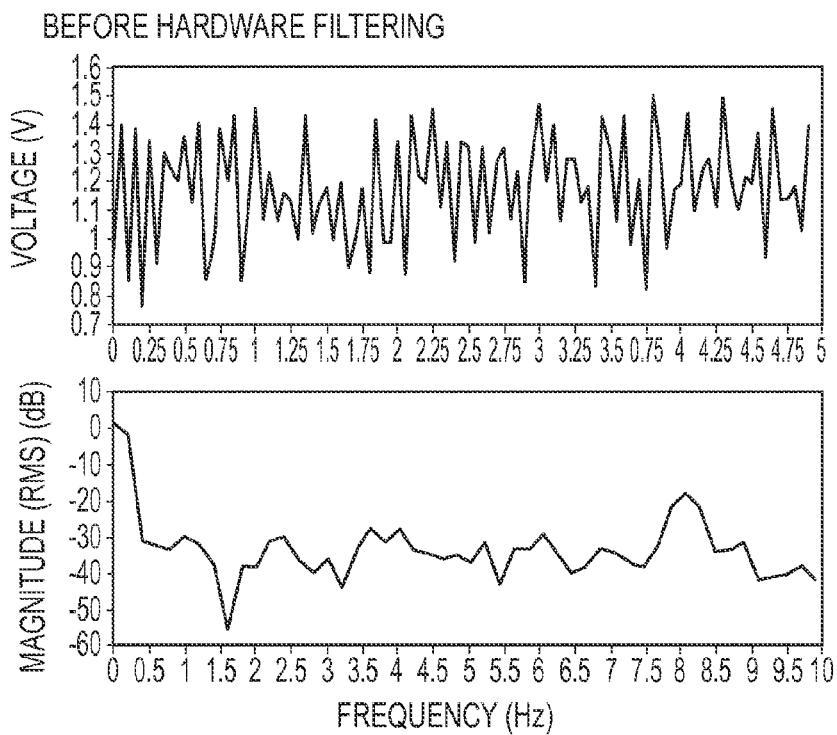
FIGS. 9A-9B illustrate sample signals (V vs. Hz) and noise profile (dB vs. Hz) taken before (FIG. 9A) and after (FIG. 9B) hardware filtering according to aspects of the present disclosure.
Figure 9B:
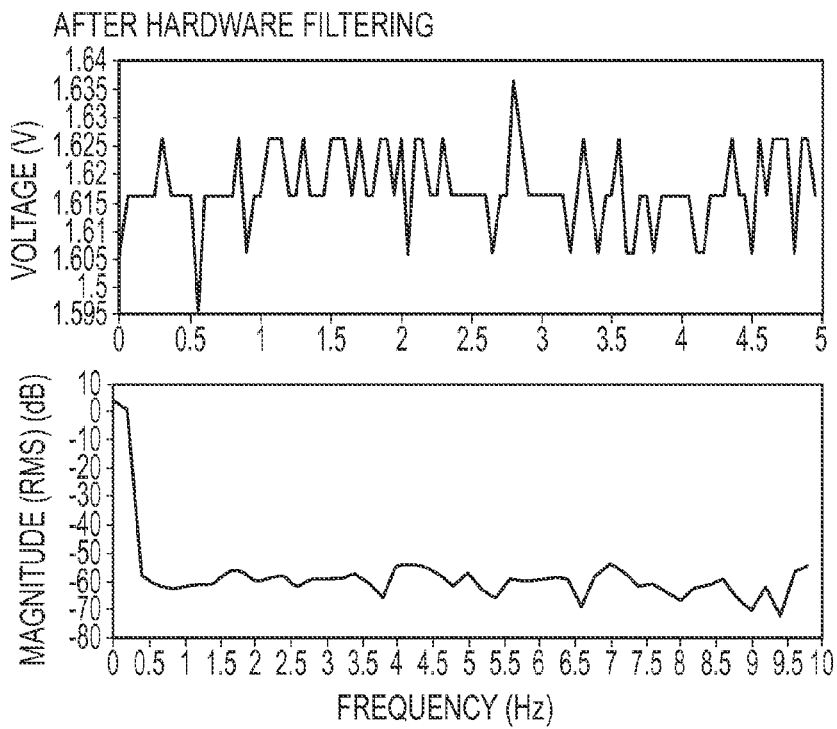
Figure 10:
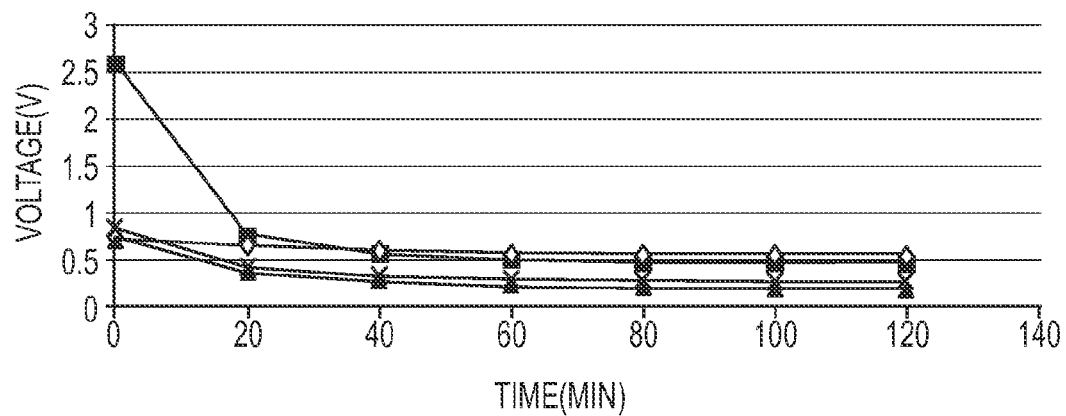
FIG. 10 is an exemplary voltage vs time graph according to aspects of the present disclosure.
Figure 11:
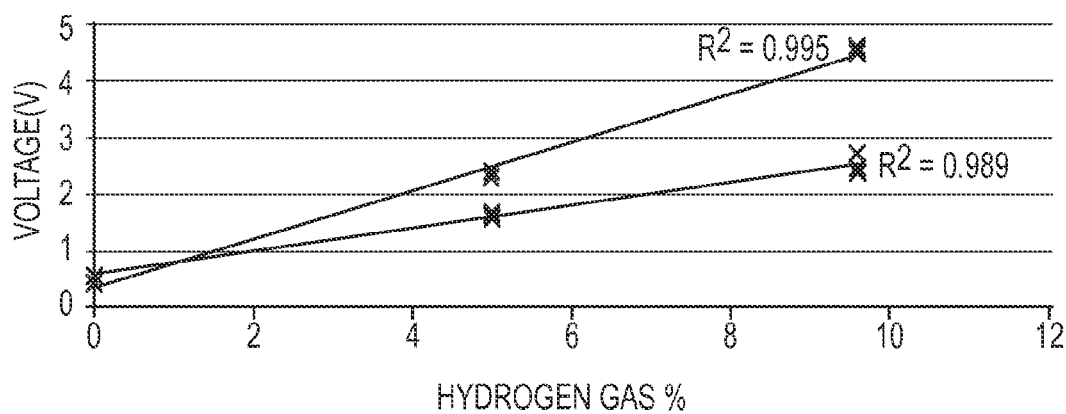
FIG. 11 is a graph and fit of data, showing voltage as a function of percent hydrogen gas according to aspects of the present disclosure.

For a more detailed discussion of various other aspects of the measuring system 100, reference is now made to FIGS. 7-24I which depict or illustrate various functional diagrams and elements of the circuitry that may be employed in the system and exemplary circuit diagrams related thereto, as well as experiments performed to test various aspects of the system or individual elements of the system (e.g. probe function was tested and some of the results described at FIGS. 10 and 11).

Circuitry

Figure 7:
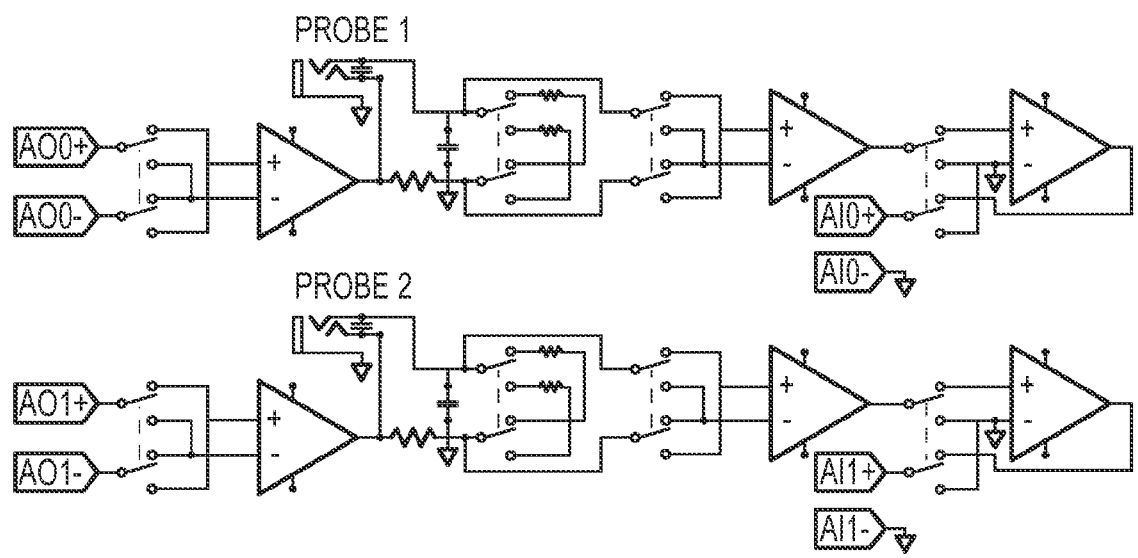
FIG. 7 illustrates a functional schematic diagram of one embodiment of the signal processing and system control device of FIG. 1.
Figure 8A:
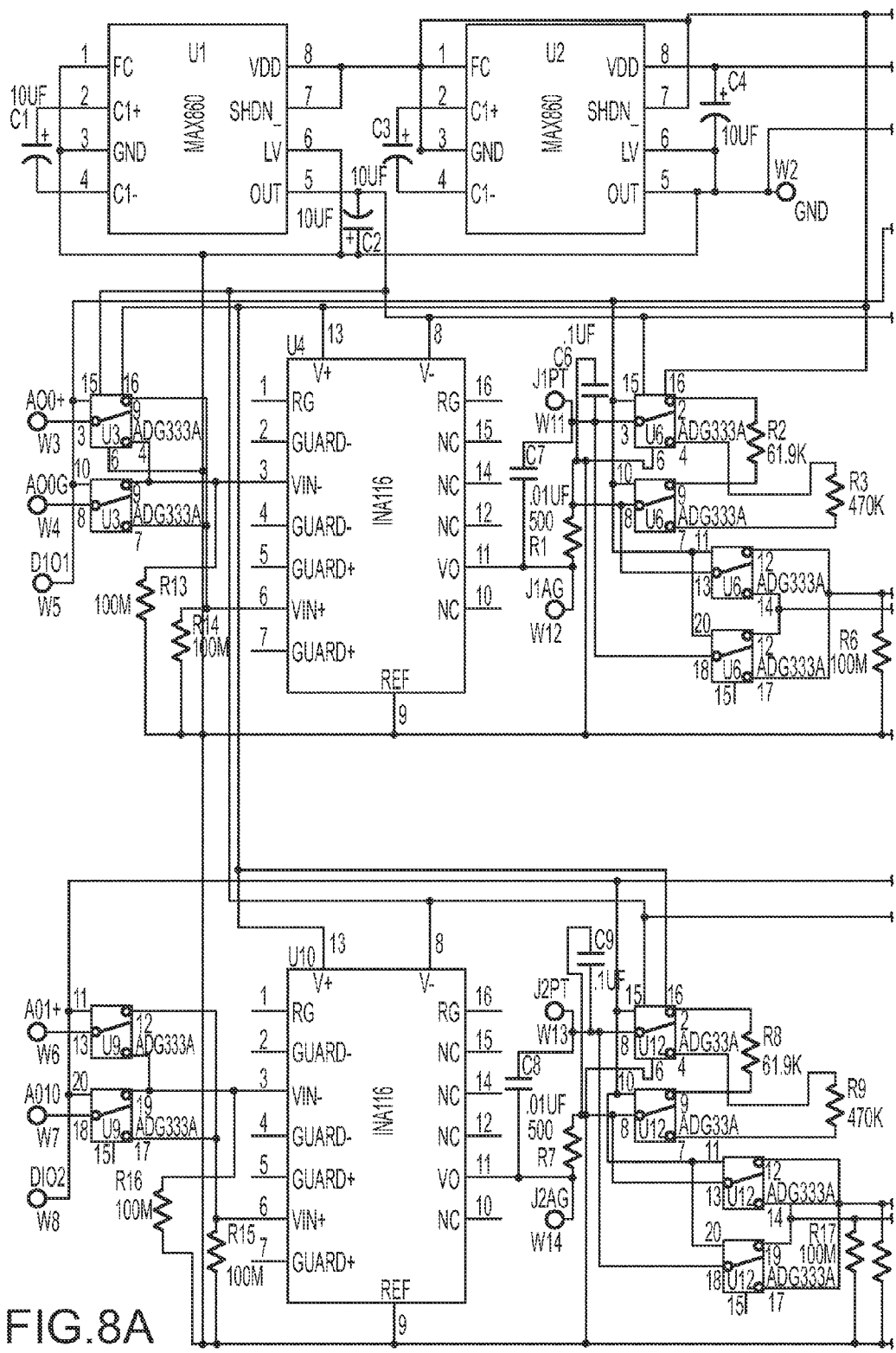
FIGS. 8A-8B illustrate an exemplary circuit wiring diagram for use with the system as disclosed herein.
Figure 8B:
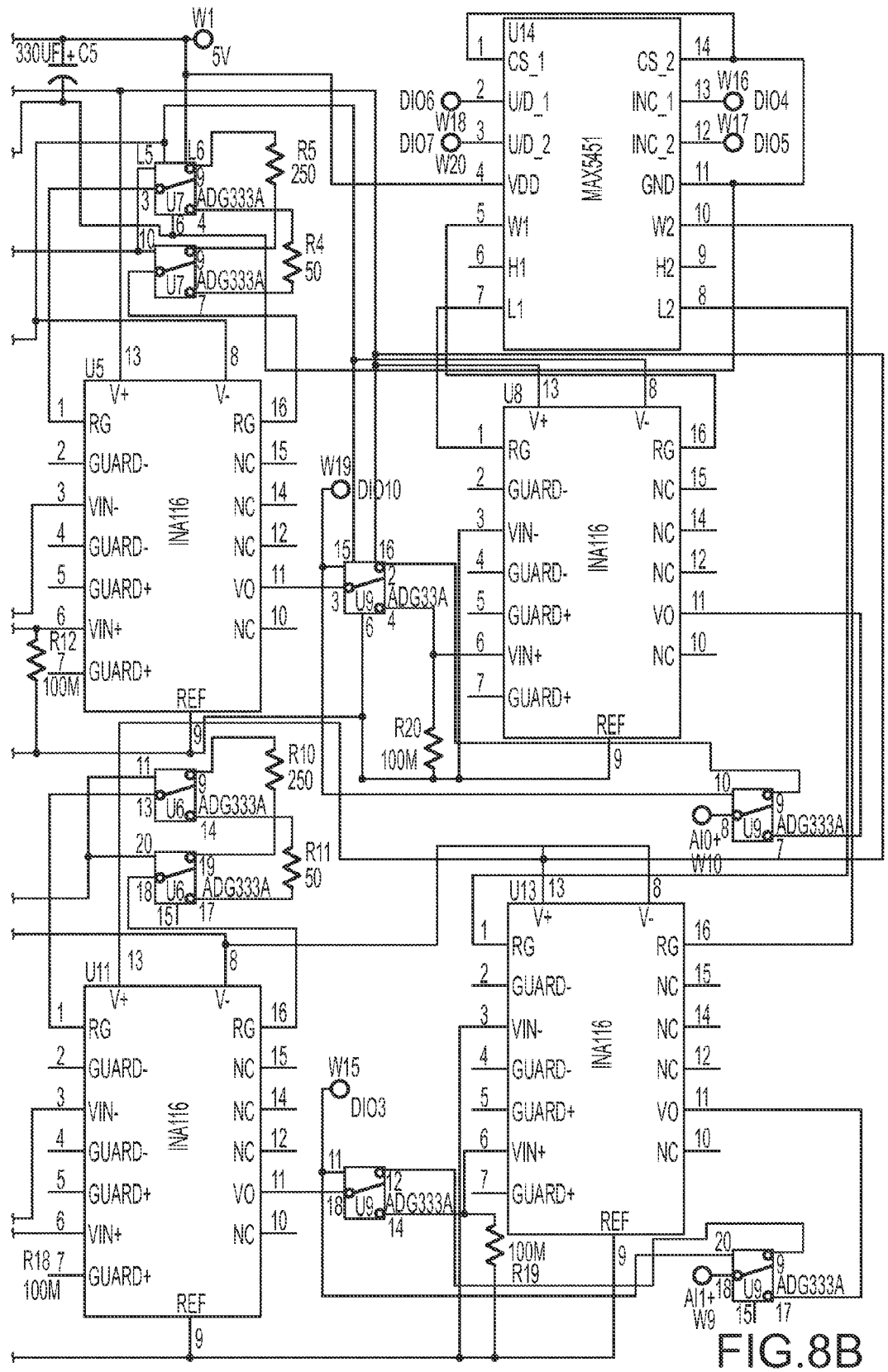
Figure 27A:
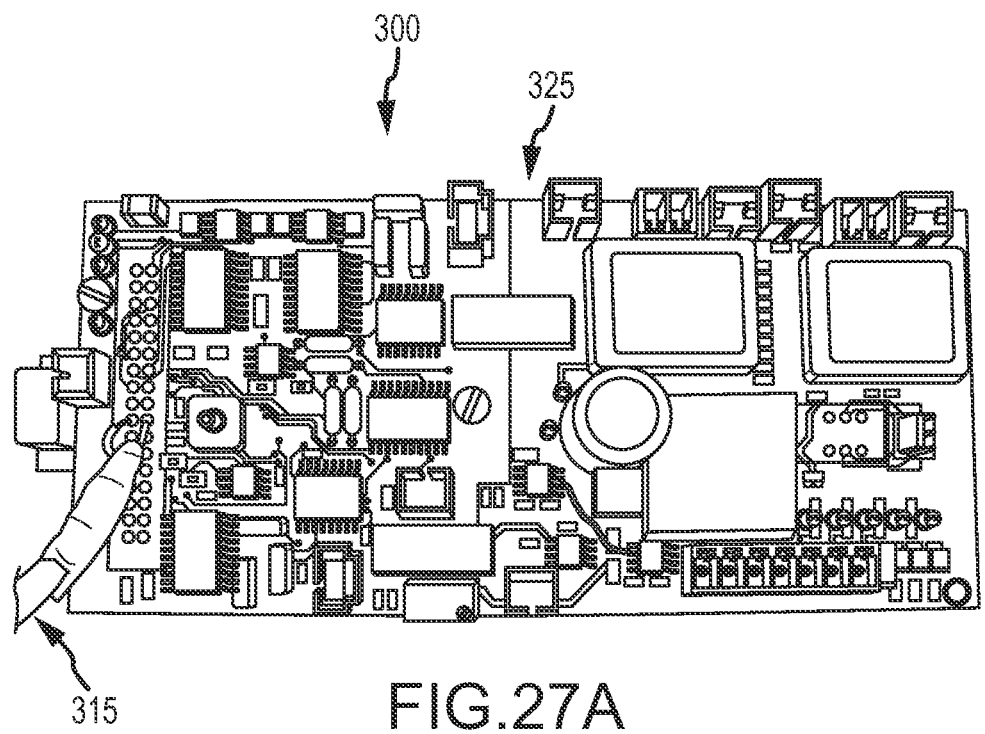
FIGS. 27A-27B depict a DAQ PCB and a signal processing and system control board of the signal processing and system control device of the system of FIG. 26A.
Figure 27B:
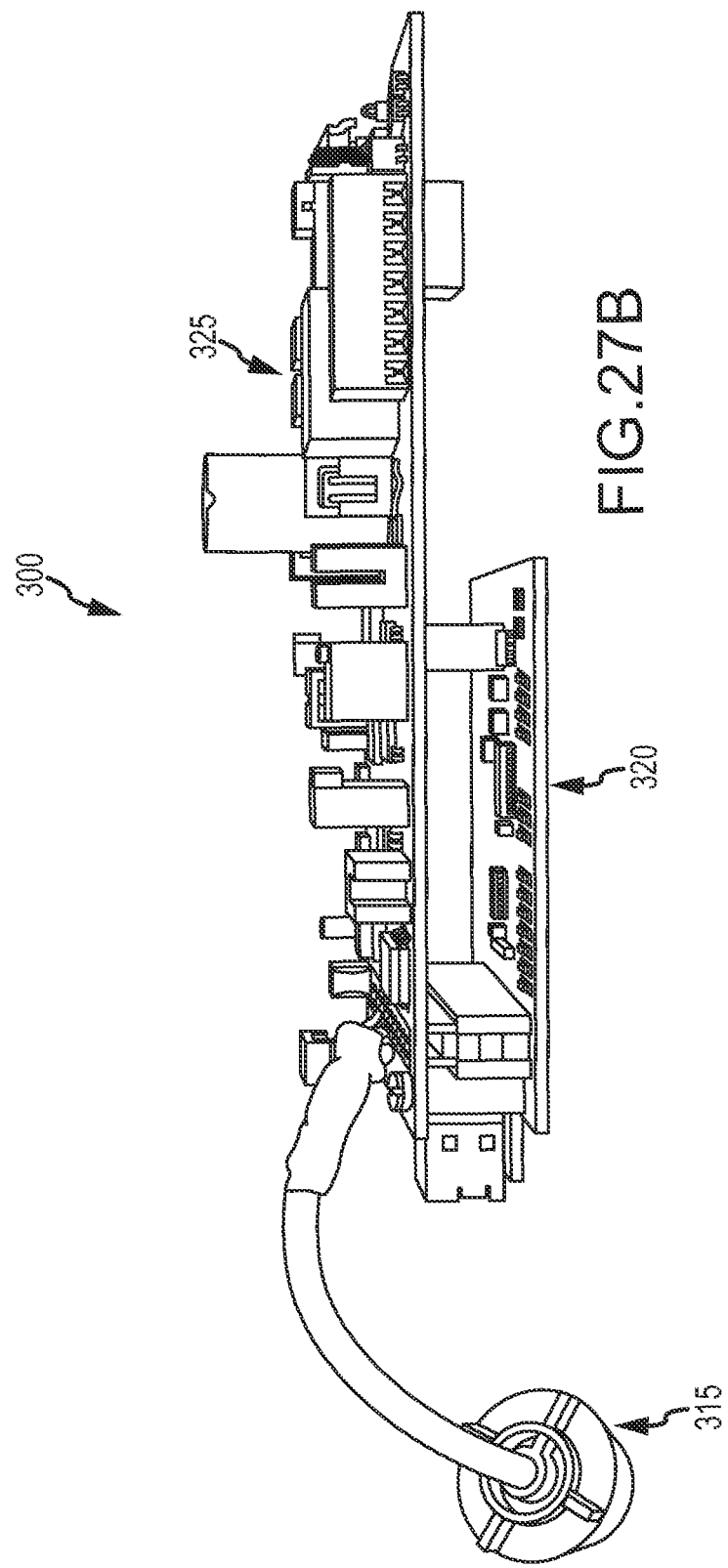

One embodiment of the circuitry is shown in FIGS. 7-8B, with reference to the signal processing and system control device shown in FIG. 3 and others. FIG. 7 illustrates a functional schematic diagram of one embodiment of the disclosed signal processing and system control device. FIGS. 8A and 8B illustrate one embodiment of an exemplary circuit wiring diagram. Another embodiment of the circuitry is shown in FIGS. 27C-27o, with reference to the signal processing and system control device shown in FIGS. 27A and 27B and others. FIGS. 27A-B depict a DAQ PCB and a signal processing and system control board of the signal processing and system control device of the system of FIG. 26A. FIGS. 27C-27K are functional diagrams and circuit diagrams of the signal processing and system control board of FIGS. 27A-27B. As discussed above, the circuitry allows for acquisition, filtering, smoothing and amplification of signals for making oxygen and hydrogen measurements in a photobiologic redox reaction. Photo-biologic may refer to a process wherein metabolism is initiated or enhanced by exposure to light from a light source. The signals or information produced in this system may be provided to a computing device for further processing, storage and analysis of the signals. As shown in the respective circuit diagrams and in the description found below, a specific part number may be provided as one example of a part that may be used to perform the specific function. For example, INA116 from Texas Instruments is specifically referenced. However, it can be appreciated that substitute parts may be used for the specific part numbers described herein while still providing the same functionality to the circuit and the specific part numbers should be understood to be only one embodiment. That is, another instrumentation amplifier may be used while still maintaining the amplification function in the system. Such substitution that maintains the same functionality is still within the spirit and scope of the invention. In addition, it can be appreciated that the circuits described herein could be implemented in FPGA (Field Programmable Gate Array) or other application specific integrated circuit.

A software controlled voltage may be applied by the NI USB-6008 unit from its analog out ports to an INA116 instrumentation amplifier. An ADG333A SPDT switch before the INA116 allows positive and negative polarization of the output signal at the silver head of the Ag/Pt probe. Electron flow between the probe heads may be measured across a load resistor (e.g., 61.9 kΩ in $O_2$ sensing, 470 kΩ in $H_2$ sensing) by another INA116 instrumentation amplifier. The output voltage may be read directly by the NI USB-6008 unit or amplified further in hardware.

INA116—Texas Instruments

The expected sub-microamp currents from the chemical reactions at the probe heads are susceptible to interference from input bias currents in most operational amplifiers. The INA116 may use 3 fA at 25° C. as input bias current and is favorable for this type of precision measurement. As well, the IC has a low 1 mA quiescent current and puts very little stress upon the NI USB-6008 power supply.

ADG333A—Analog Devices

The ADG333A is a quad SPDT (Single Pole Dual Throw) switch capable of channeling a up to approximately 20 mA continuous current through its source and drain terminals. The switches may be digitally controlled by a 5V TTL signal provided by the NI USB-6008. The switches accept Vdd and Vss in positive and negative polarizations, allowing for a wide range of voltages to be passed through without attenuation due to input voltage proximity to the rails. Each ADG333A has a positive and negative power supply to account for this.

MAX860—Maxim IC

The NI USB-6008 can provide approximately +5V at its power terminal, thus a DC-DC converter may be used for a negative and higher positive power supply. The MAX860 does not use any inductors for typical operation, reducing EMI and unit cost, as well as physical height. There are two MAX860's in operation in this circuit, one may act as a voltage inverter to provide −5V and one may act as a voltage doubler to provide +10V. Again, each IC has a low quiescent current of 0.2 mA, for use in a USB powered device.

MAX5451—Maxim IC

In some embodiments, after signal acquisition and differential amplification, a second tier of amplification can be activated in software. Checking this field changes an ADG333A switch and sends the acquired signal to another INA116 with a MAX5451 50 kΩ digital potentiometer acting as its gain resistor. The equation for gain in the INA116 is $G=1+50 k/R_g$. At power-on, the MAX5451 defaults to half of its full value, providing an initial secondary gain of 3 to the signal. The digital potentiometer's resistance can be modulated using a falling edge digital signal at its increment terminals, the direction of which is determined by an Up/Down digital terminal. The MAX5451 can span its entire resistance in 256 discrete steps, allowing for a gain multiplier between 2-1000 V/V on the INA116.

NI USB-6008—National Instruments

In some embodiments, the DAQ 320 may be from National Instruments. However, it should be understood that other DAQs from National Instruments or other manufacturers may be implemented. The National Instruments DAQ has a USB connection and interfaces with LabVIEW software programmed specifically for this device. The unit has a 5V power supply capable of providing 200 mA, two analog output signals (one for each probe), 4 analog input terminals (differential and RSE), 12 digital input/output terminals, 12 bit resolution, and 10 kSample/s acquisition rate.

Hardware Filtering

A capacitor between +5V and ground may be used to clean and protect the power to one or more IC's on the board. At the probe interface on the board, a 0.01 µF capacitor between the silver and platinum terminals may be provided to eliminate or reduce EMI from the probe cables. In parallel with the ADG333A terminals that switch between load resistors, a 0.1 µF capacitor may be provided to clean the power and Johnson noise inherent in the IC and resistors. The raw signal that is acquired by the DAQ from the PCB is sent to software, where the voltage is observed and the standard deviation of the previous 3 seconds of data is processed. As a result of this filtering, the standard deviation may be low (e.g., around 0.006-0.01 V with or without a probe connected). Since hardware filtering cancels predominant noise in the system, including 60 Hz noise, further software filtering may be performed post-acquisition to eliminate any other environmental noise that may arise, such as EMI from nearby instrumentation and high-voltage devices.

Signal Noise

A sample signal taken from the unit with and without hardware filtering (Voltage vs. Seconds), with its respective noise profile (dB vs. Hz), is shown in FIG. 9.

The filtered signal coming from the hardware may be primarily DC. During observation of the acquisition signal, deviation is present, but is on the order of the resolution of the DAQ (14.7 mV), and over 3 seconds of samples, standard deviation is seen to be 4-10 mV. The noise present in the signal does not interfere with the data of interest, as the expected voltage range at 1729 m altitude in an $O_2$ measurement can be 0-2.5 V depending upon the quality of the probe. Standard deviation seen during a $H_2$ measurement is typically 2 mV higher than in an $O_2$ measurement and likewise does not interfere with the data of interest.

Measurement Linearity

Four used YSI 5331 $O_2$ probes were polarized at –0.6 V in order to sense $H_2$ and subjected to three different pre-mixed, ultra-pure (+/−0.001%) concentrations of $H_2$ gas: 0% (argon bubbling), 5%, and 9.6%. The probes were allowed to stabilize over a 2 hour period in 50 mm MOPS solution and were considered stable by visual inspection of the software GUI. 0% voltage levels vary with probe condition (FIG. 10). $H_2$ gas mixtures were then bubbled into the vessel until the voltage was visibly stable and an average of the stable portion of the signal was taken. Then argon was bubbled to purge out $H_2$ until the 0% voltage was reached again. This was repeated in triplicate for both 5% and 9.6% $H_2$ gas mixtures (FIG. 11).

Figure 27C:
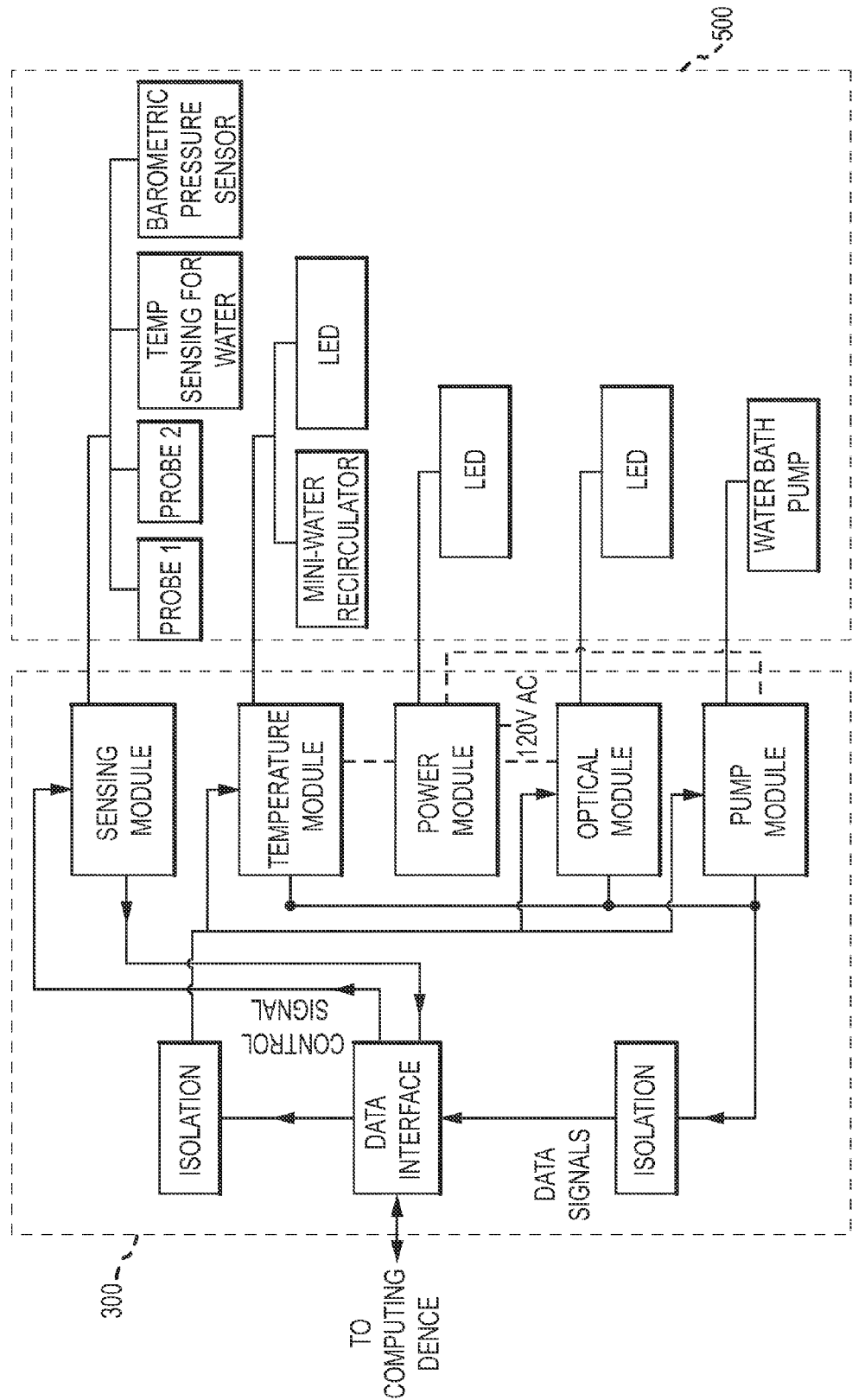
FIGS. 27C-27J are functional diagrams and circuit diagrams of the signal processing and system control board of FIGS. 27A-27B.

Voltages seen in this experiment were specific to the probes' quality and condition (i.e. term of previous use, care taken in cleaning, storage, and Teflon® film thickness, KCl concentration), so different levels may be observed with different probes and preparations; however, the linearity is not expected to change unless physical damage to the probe is present. Two of the probes were sensitive enough to saturate the INA116's maximum voltage, and were not included in the above graph. Thus, in some embodiments, a more variable gain setup in circuitry may be provided to accommodate for probes with much greater sensitivity. Further, calibration measurements may be taken prior to acquisitions. The $R^2$ values show good linear fits with the data, and demonstrate linearity up to 9.6% aqueous $H_2$ gas FIG. 27C is a block diagram for an exemplary circuit. In FIG. 27, the computing device 600 is in communication with a Data Interface device. The Data Interface is in communication with a first Isolation Module, a Second Isolation Module, and a Sensing Module 1000. The Data Interface sends a Control Signal to the Sensing Module 1000. The Sensing Module 1000 is in communication with a Probe 1, a Probe 2, a Temperature Sensor, and a Barometric Pressure Sensor. The Temperature Sensor is for sensing the temperature of water being circulated within the cell jacket. The Barometric Sensor measures pressure. The Sensing Module 1000 sends a Feedback Signal to the Data Interface. The first Isolation Module receives signals from the Data interface and sends signals to a Temperature Module 1100, an Optical Module 1300, and a Pump Module 1400. A Power Module may also be included to provide a DC-Power Source for the Temperature Module 1100, the Optical Module 1300, and the Pump Module 1400. The Temperature Module is in communication with a Peltier Module for a mini-water re-circulator and a peltier module for cooling a Light Emitting Diode (LED). The Temperature Module 1100 helps keep temperature constant even if light output is changed. The Optical Module 1300 provides optical feedback to accurately control the lighting and illumination of the cell. The Optical Module 1300 helps to maintain a constant light output depending on light output parameters.

The Pump Module 1400 controls a pump for a re-circulating water bath. The Power Module 1200 provides power filtering, power conversion, and LED indicators. The Temperature Module 1100, Optical Module 1300, and Pump Module 1400 are in communication with, and send signals to, a second Isolation Module. The Second Isolation Module sends Data Signals to the Data Interface.

Figure 27D:
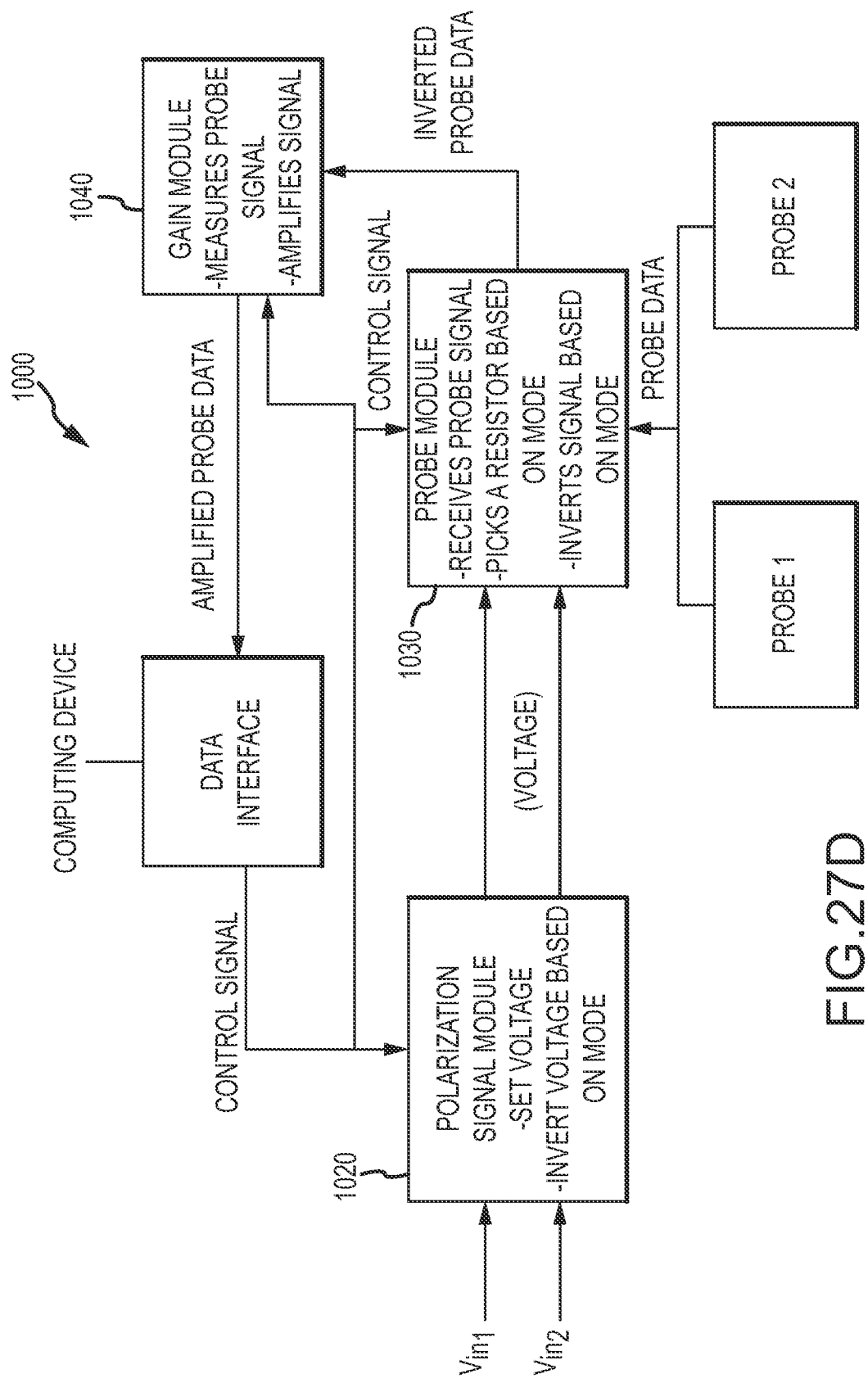

As depicted in FIG. 27D, the Sensing Module 1000 comprises a Polarization Signal Module 1020, a Probe Module 1030, and a Gain Module 1040. The Polarization Signal Module 1020, the Probe Module 1030, and the Gain Module 1040 receive control signals from the Data Interface. The Polarization Signal Module 1020 receives two voltage inputs, $V_{in1}$ and $V_{in2}$. The Polarization Signal Module 1020 sets the voltage and inverts the voltage based on mode. The Polarization Signal Module 1020 outputs two voltage signals to the Probe Module 1030. The Probe Module 1030 inverts signal and picks a resistor based on mode. The Probe Module 1030 receives probe signals from Probe 1 and Probe 2. Inverted Probe Data is sent from the Probe Module 1030 to the Gain Module 1040. The Gain Module measures the probe signal received from the Probe Module 1030, amplifies the signal, and outputs Amplified Probe Signal data to the Data Interface.

Figures 1, 27E:
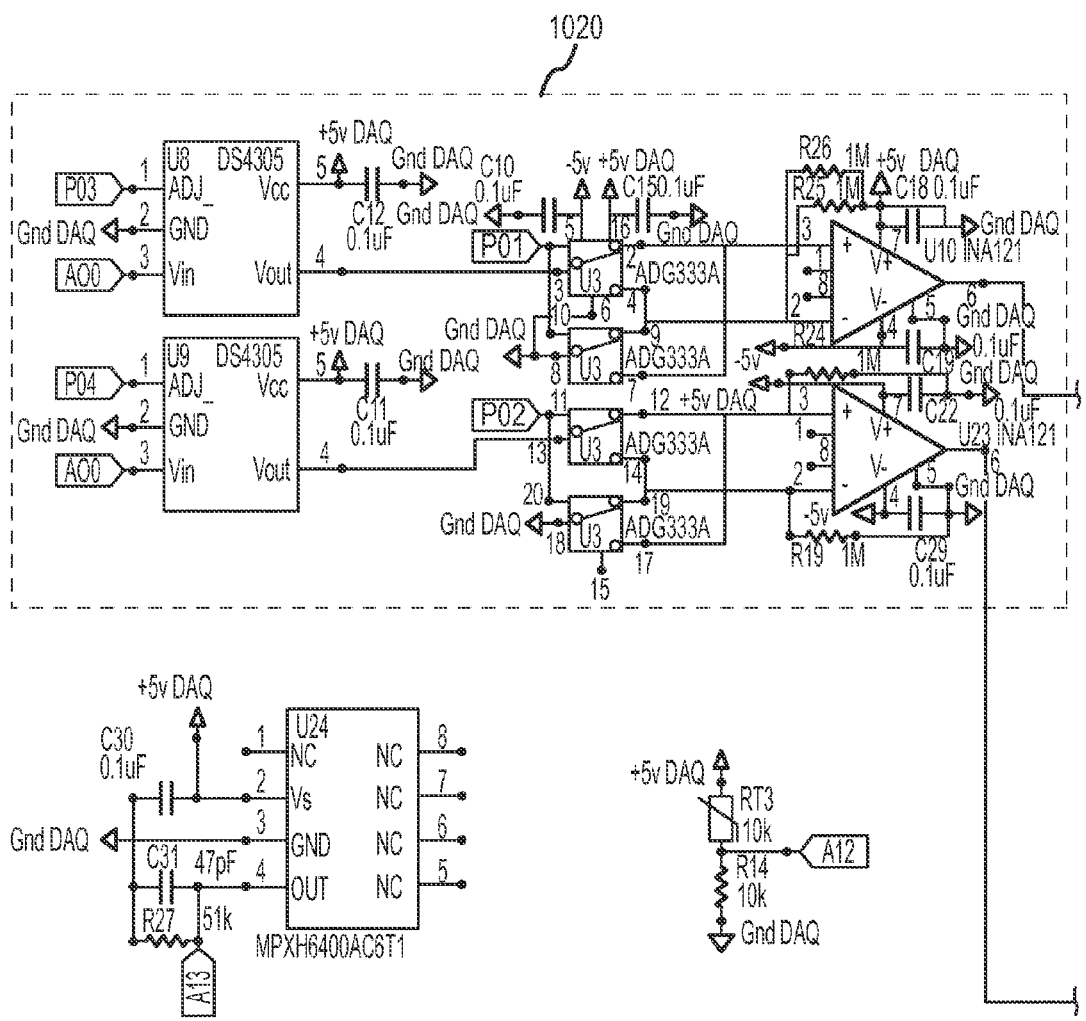
Figures 2, 27E:
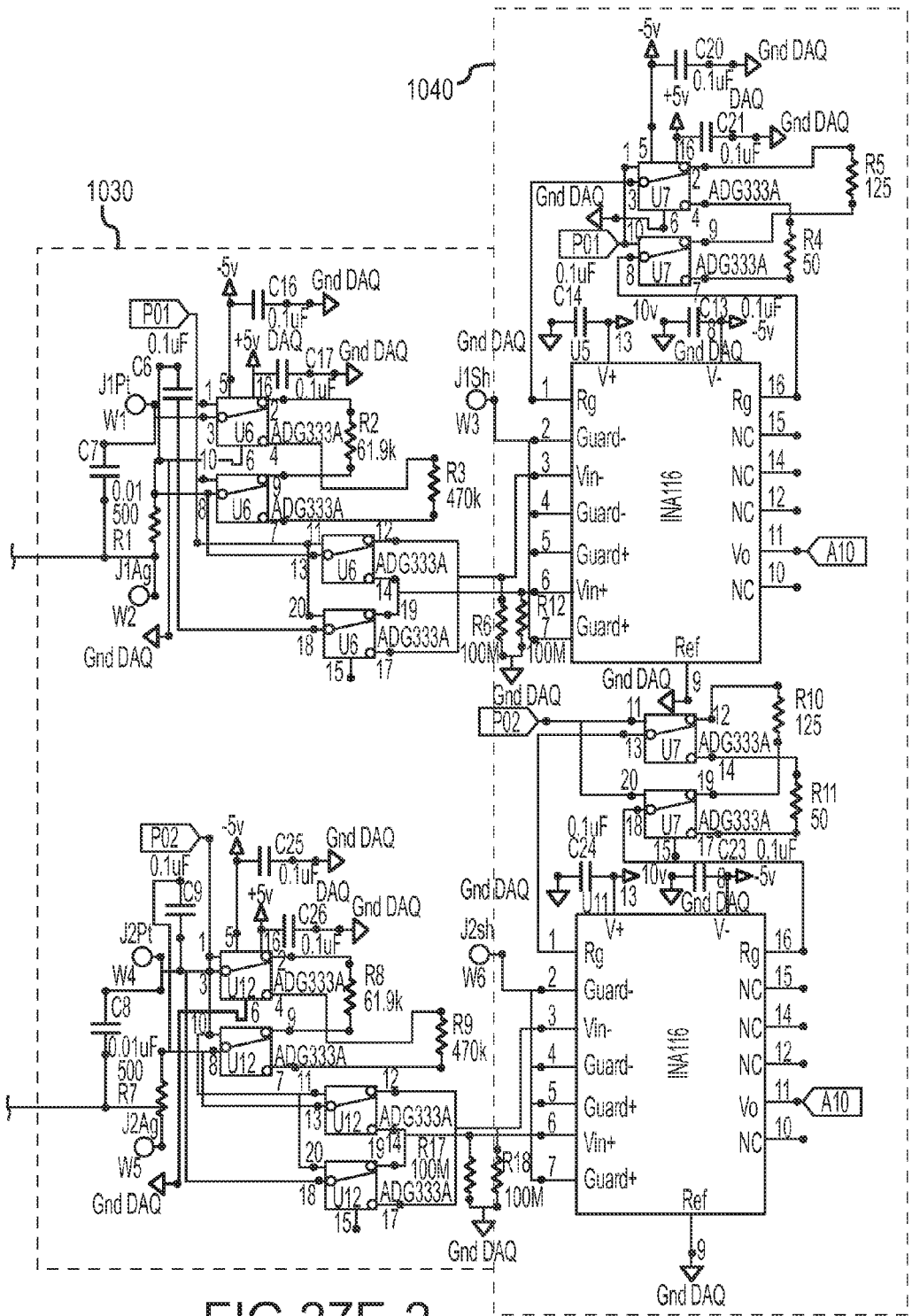
Figure 27F:
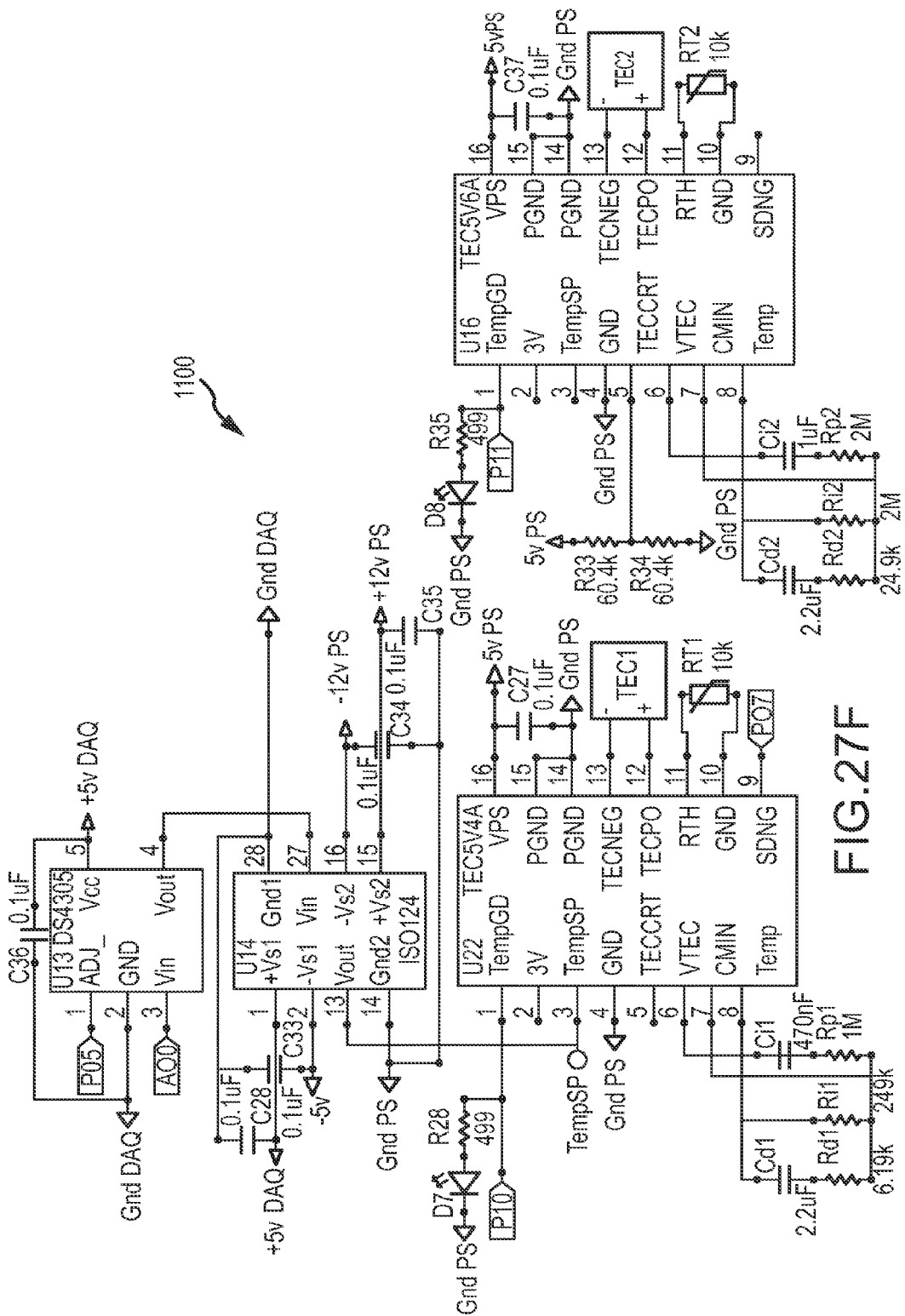
Figure 27G:
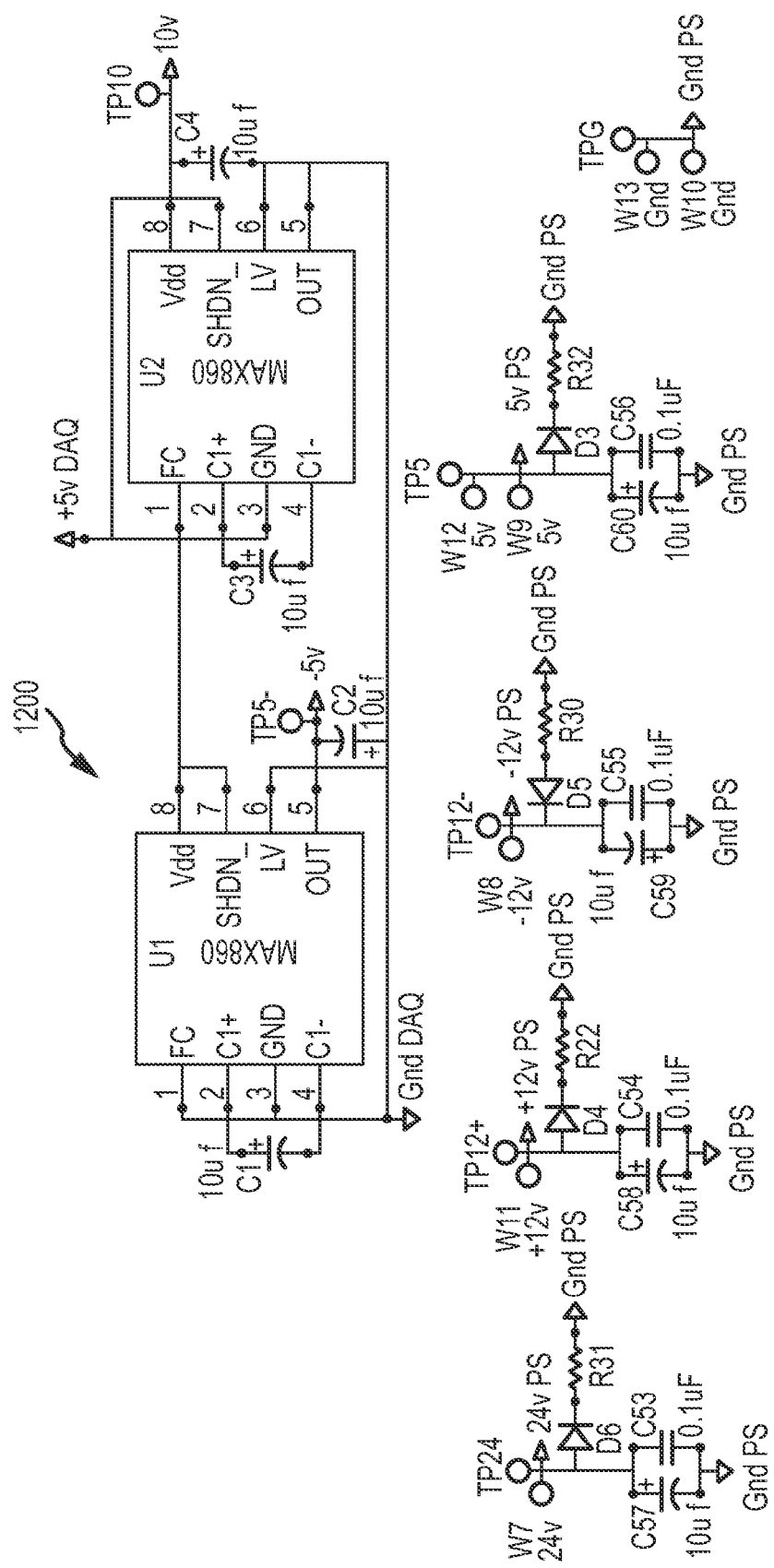
Figure 27H:
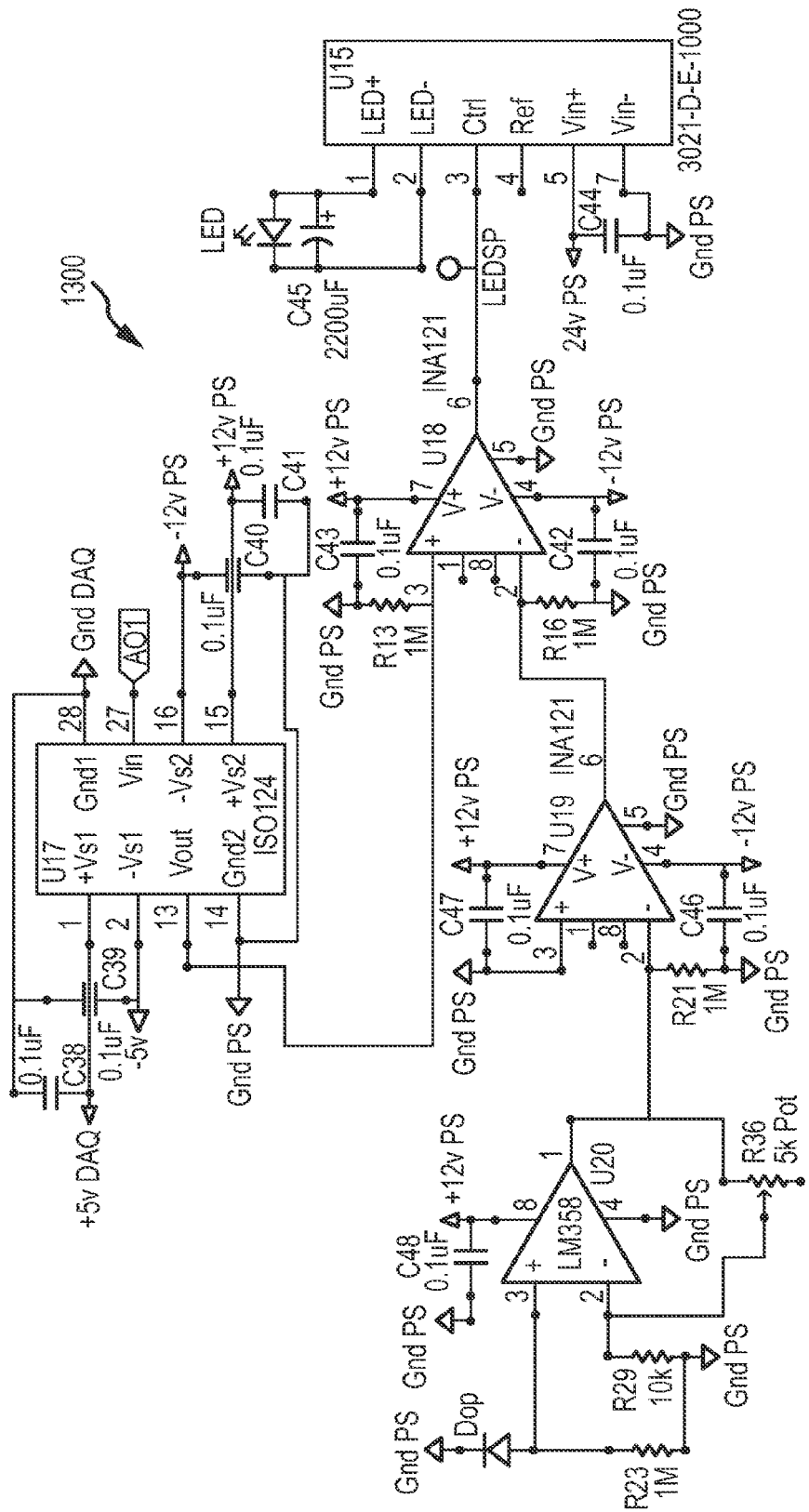
Figure 27I:
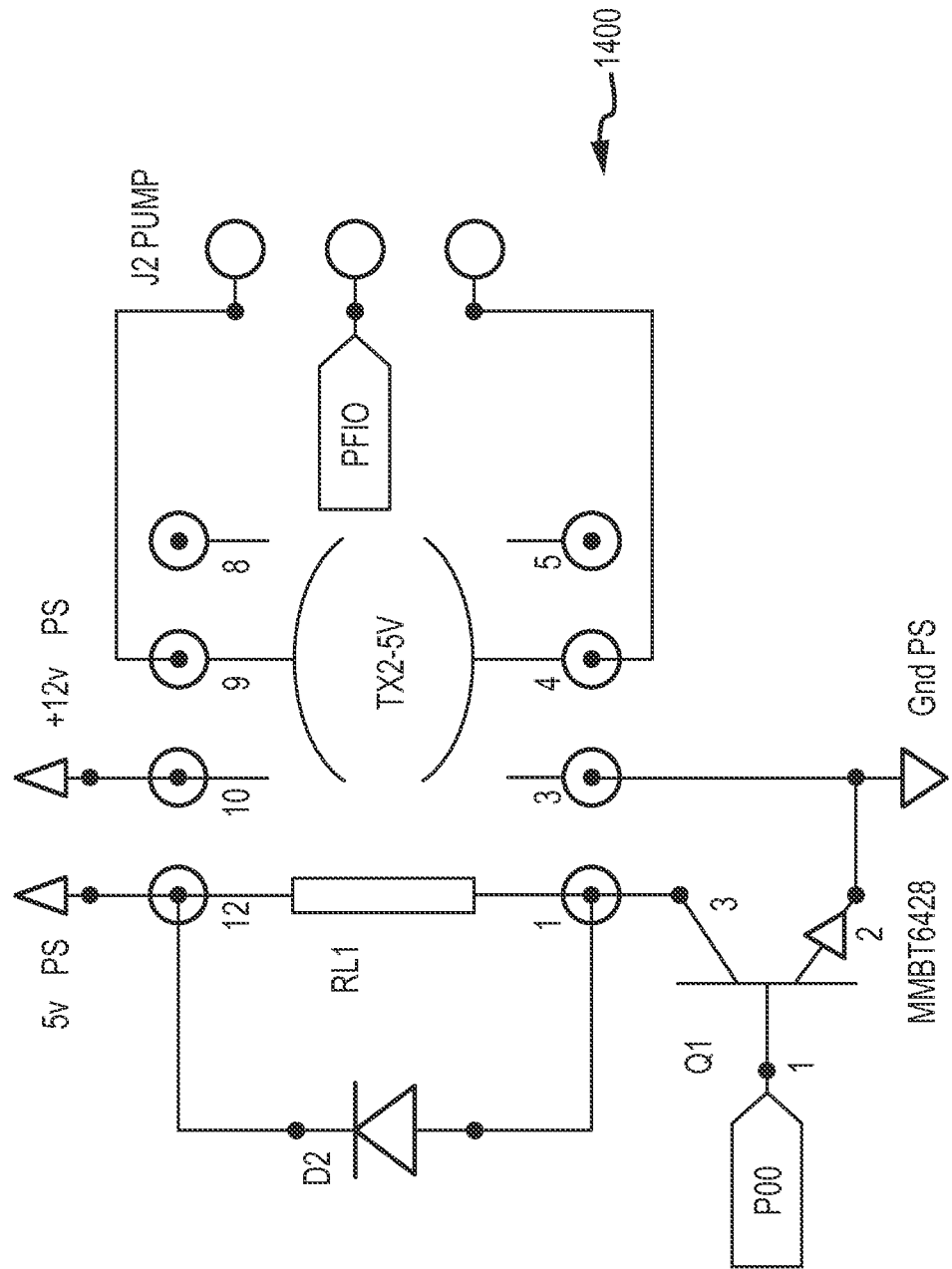
Figure 27J:
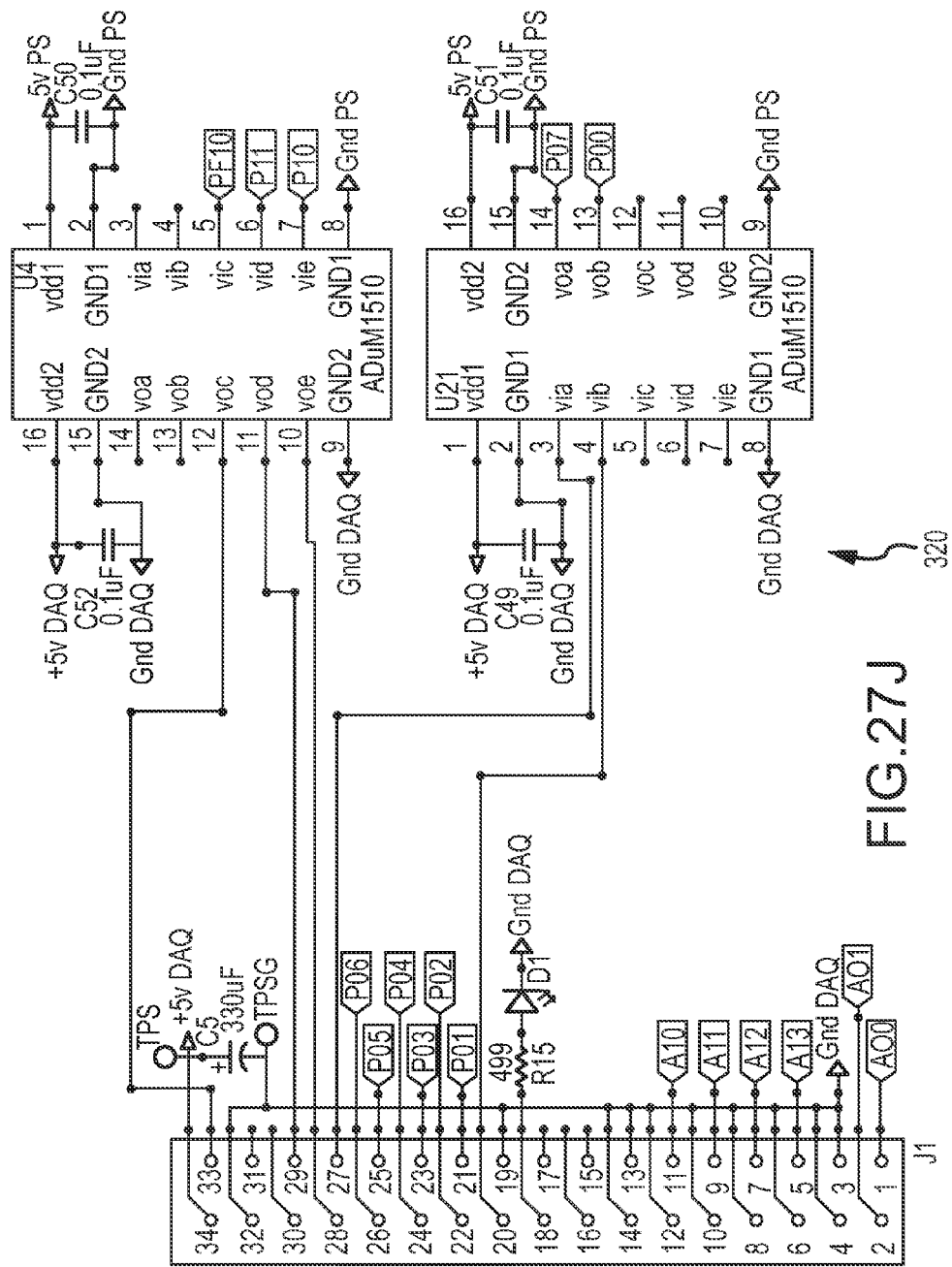

FIG. 27E is a circuit diagram depicting the Sensing Module 1000 (for probe sensing and signal amplification), barometric sensor (bottom left), and Temperature Sensor (middle bottom; for sensing water temperature). FIG. 27F is a circuit diagram depicting the Temperature Module 1100 for controlling the temperature of the water bath and the LED. FIG. 27G is a circuit diagram depicting the Power Module 1200 for power filtering, LED indicators, and power conversion. FIG. 27H is a circuit diagram depicting the Optical Circuit 1300 for providing optical feedback and illumination of the cell. The optical feed back helps in providing accurate control of the lighting and a constant light output. FIG. 27I is a circuit diagram for the Pump Module 1400, which controls the water bath pump. FIG. 27J is a circuit diagram of Signal Processing and Control Device 320, showing 2 digital isolation devices for isolating power from external power and USB power. In FIG. 27J, "J" depicts a connector for signal processing (and where the DAQ connects to a signal and processing board), "P" stands for digital signal and "AO" is analog in/out.

Software

Acquisition Panel

Figure 12:
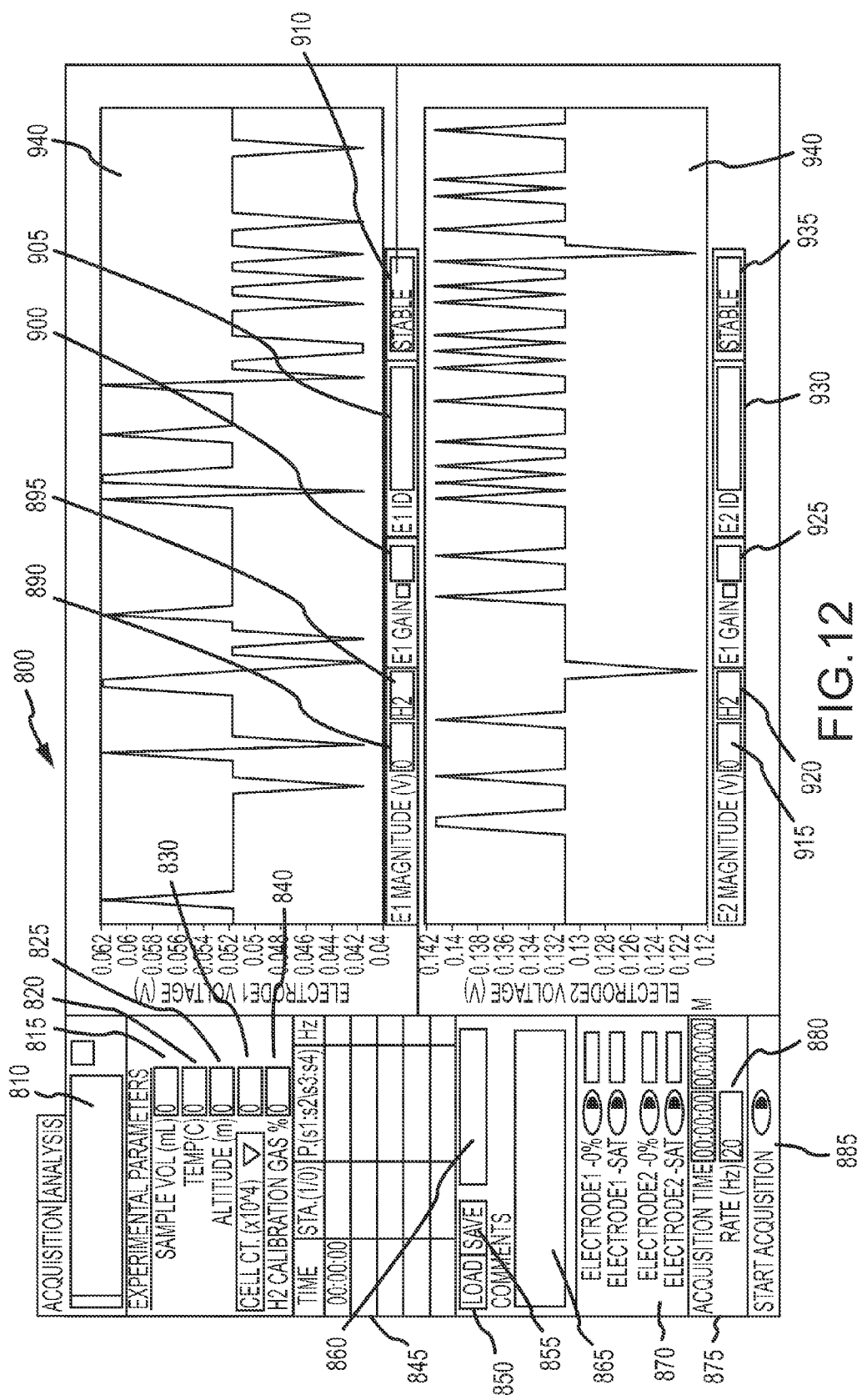
FIG. 12 shows an exemplary data acquisition panel for software interfacing with the system of FIG. 1 according to aspects of the present disclosure.

An exemplary acquisition panel is shown in FIG. 12. The acquisition panel 800 controls the NI-DAQ 6008 USB unit and allows the user to change experiment parameters. Individual electrodes are polarized according to magnitudes and modes which may be defined by the user. FIG. 12 shows a panel displaying raw data 940 acquired by the signal processing and system control device, the data 940 is displayed for two electrodes separately. In various embodiments, a user may input information pertinent to post-processing, such as $H_2$ calibration gas percentage, altitude, temperature, sample volume, cell count, and chlorophyll mass. The state of each channel ($H_2$ or $O_2$ measuring) is saved as a bit in the data file. Lighting schema may be programmed into a table on the GUI.

The upper left field 801 of FIG. 12 shows the file path of an acquisition file. The user may click a browse button to bring up a dialog box for choosing a file folder and name. FIG. 12 also shows $H_2$ calibration gas percentage 840 (obtained from tank label), a box 830 for choosing between cell count ($\times 10^4$) or chlorophyll mass (μg) (obtained prior to acquisition). Other boxes in FIG. 12 allow entering of sample volume (mL) in a volume box 815 (total of algal sample volume and buffer solution, e.g. 50 mM MOPS (pH 6.9) buffer solution), temperature (° C.) in a temp box 820, and altitude (m) in an altitude box 825. In some embodiments, the altitude box is not used where a pressure sensor is already a part of the system. Each of these values can be obtained; quantification of chlorophyll mass may include spectrophotometric measurements, and cell count may be obtained through hemacytomoter or Coulter counter measurements. A lighting table 845 is also shown. The lighting table may allow users to define a lighting schema that may be activated during an acquisition—the function of the lighting schema is described in the "Parse Lighting State" section below. Lighting methods can be saved by clicking a SAVE box 855 or loaded by clicking a LOAD box 850. The active lighting scheme file is indicated in a lighting scheme box 860. Comments may be added in a comments box 865, and these comments may be saved, if desired. A probe's calibration acquisition may be displayed at calibration buttons 870. Data at these buttons 870 may be taken if calibration files have not been acquired or if probe drift has significantly affected calibration values. Depicted below the raw data 940 are boxes for electrode polarization voltage magnitude 890 915, measurement state 895 920, gain activation and control 900 925, probe IDs 905 930, and stability indicators 910 935. Probe IDs may be helpful in tracking sensitivity drift separately from this program, as well as baseline drift. Also included in FIG. 12 are fields for acquisition time 875 and rate 880. Acquisition may be started by clicking a start button 885.

Acquisition State Machine

Figure 13:
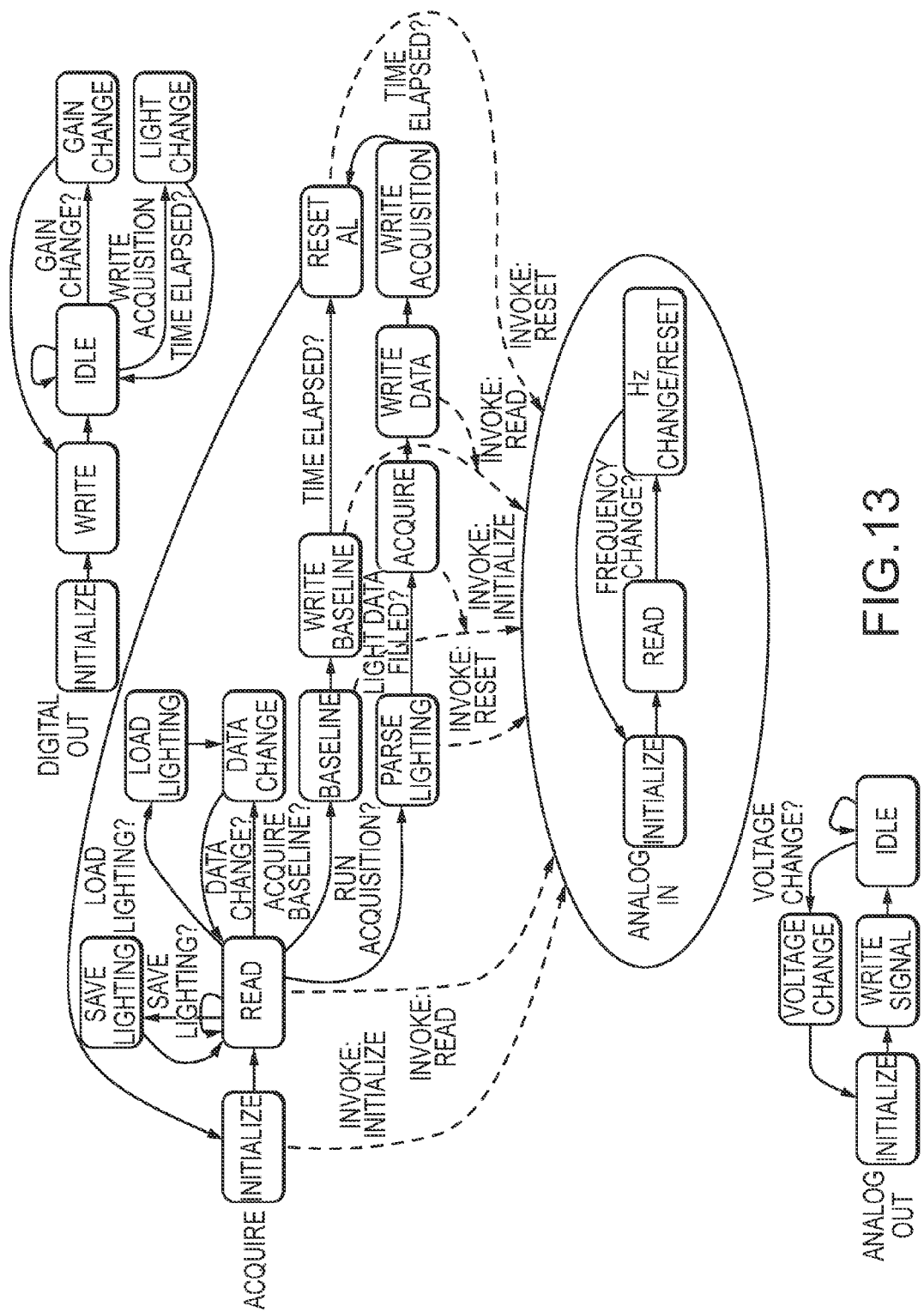
FIG. 13 is a flow diagram for the acquisition state machine that may be used with aspects of the system of FIG. 1.

FIG. 13 is a flow diagram depicting the acquisition state machine. The acquisition state machine controls three parallel tasks running simultaneously pertaining to data acquisition, probe polarization, and state and gain control. The state machine runs continuously at 1 ms/loop iteration, allowing for a maximum sampling rate of 1000 Hz.

Analog Out Task

The Analog Out Task runs separately from the Analog In and the DIO tasks. It sends the user-defined polarization voltage from the USB DAQ Analog Output Channels through the PCB to the two electrodes. The program allows the user to change the voltage any time during execution, so the Analog Out Task continuously polls the Front Panel electrode polarization values and if the value changes, the task writes the new value to the electrodes. The Analog Out Task iterates at the loop iteration speed to maximize responsiveness to the user's changes.

Initialize State

Creates and configures the analog out NIDAQmx task for the AO0 and AO1 channels. AO0 is configured to write a polarization voltage to Electrode 1 and AO1 is configured to write to Electrode 2.

Write State

Writes the user-defined Electrode 1 and Electrode 2 polarization voltages to their respective analog out channels.

Idle State

Checks for a change in user-defined voltage magnitudes.

V Change State

Stops the current task and records new voltage magnitude values.

Analog In Task

The Analog In Task runs separately from the Analog Out and the DIO tasks. It acquires data at the user-defined rate and duration from the USB DAQ Analog Input Channels through the PCB from the two electrodes. The program allows the user to change the acquisition rate at any time during execution, so the Analog In Task continuously polls the Front Panel sample rate control, and if the value changes, the task changes the acquisition rate.

Initialize State

Creates and configures the NIDAQmx analog in voltage task and sample clock with the user-defined acquisition rate, and initializes a 3-second time array used in determining probe stability. AI0 is configured to acquire data from Electrode 1, and AI1 acquires the Electrode 2 signal data.

Read State

Reads samples from the "Analog In" NIDAQmx task. Three seconds of samples are accumulated in an array and analyzed for stability. The samples are analyzed with a linear fit algorithm and the probe is considered stable if the linear slope is within the range of +/−0.0002 V/s (the average slope of the second hour of probe relaxation from FIG. 10). Stability checks do not interfere with acquired data, nor do they prevent the user from performing an acquisition. Stability indicators are simply recommendations to the user that the probe drift is low enough to not significantly affect acquisition data. It is determined by the user whether or not the length of the acquisition would be affected by probe drift at any given point, but it is advisable to wait for probe stability to acquire accurate data.

Hz Change State

The analog in task is stopped and the new acquisition rate is stored in a cluster.

Digital Input/Output Task

The DIO Task runs separately from the Analog In and the Analog Out tasks. It sends a Boolean array (reflecting the respective DIO port) to the DIO NIDAQmx task according to the action performed by the user. It controls the on/off state of the lighting unit, the measurement state of each electrode, and the digital potentiometer dictating the secondary gain value. This task, as well, iterates at the loop iteration speed to maximize resolution and responsiveness of these controls.

Initialize State

Creates and starts the P0.0-P0.7 and P1.0 digital I/O port tasks, where:

P0.0—Light Control
P0.1—Electrode 1 $H_2/O_2$ state.
P0.2—Electrode 2 $H_2/O_2$ state.
P1.0—Electrode 1 gain activation.
P0.3—Electrode 2 gain activation.
P0.4—Electrode 1 gain increment (falling edge).
P0.5—Electrode 2 gain increment (falling edge).
P0.6—Electrode 1 gain direction (U/D_).
P0.7—Electrode 2 gain direction (U/D_).

Write State

Writes the Boolean array to the digital out task.

Idle State

Checks for a change in gain activation switches or gain increments buttons. If in the "Write Acquisition" case is active in the "Acquisition" task, this case is invoked to the "Light Change" state. If gain values are changed, the "Gain Change" state is activated.

Gain Change State

Increments or decrements the MAX5451 digital potentiometer using a simulated digital signal function. If the up or down buttons are held longer than 3 seconds, the signal increment frequency increases from 2 Hz to 5 Hz. This state remains active until the up or down button is released.

Light Change State

This state becomes active during an acquisition. It receives a Boolean from the "Acquire" case and writes it to the NIDAQmx task.

Acquire Task

Initialize State

Sets the "Analog In" case to the "Initialize" state.

Idle State

Checks for an acquisition or experimental data change. If one of the calibration file buttons is pressed, it advances the case to the "Baseline" state and parses the proper file suffix. If the "Start Acquisition" button is pressed, the "Idle" state advances to the "Parse Lighting" state to convert the timing table into Boolean data and executes the "Analog In" case to reset the analog in NIDAQmx task. Upon a change in experimental data, it advances to the "Data Change" state. If the save or load button under the lighting table is pressed, it advances to the "Save Lighting" or "Load Lighting" states.

Save Lighting

Saves the lighting information inputted by the user in the lighting table. File path is determined by a dialog box opened upon state activation.

Load Lighting

Opens a dialog box so the user can navigate to a previously saved lighting information file. The state is then advanced to the "Data Change" state to load the data into a cluster.

Baseline State

Creates the calibration file, advances to the "Write Baseline" state, and sets the "Analog In" case to the "Initialize" state in order to begin a new sample set.

Write Baseline State

Executes the "Analog In" "Read" state to acquire calibration data for 5 seconds, then advances to the "Save Baseline" state. Calibration acquisition progress is shown on a corresponding slide bar on the front panel. Data is written to the user-defined file path while this state is active.

Parse Lighting State

This state executes when the "Start Acquisition" button is pressed and writes the lighting scheme table defined on the front panel into an array. The length of the array is determined by the product of the acquisition rate and the acquisition time. Depending upon which methods and times are present in the spreadsheet, the lighting can be activated in one of three ways: Static (light is on (1) or off (0)), periodic (light is on for x seconds, off for y seconds), or modulated (on/off by frequency). A For-loop populates the array with appropriate data for the lighting control. Using the periodic method, the timing is defined as $s_1{:}s_2\backslash s_3{:}s_4$, where $(s_1, s_3)$ and $(s_2, s_4)$ are on and off times in seconds, respectively, and $(s_1, s_3)$ transitions linearly to $(s_2, s_4)$ over the course of the periodic-defined time interval.

Acquire State

Creates the acquisition, data, and lighting files as per the user-defined file path and stores the developed lighting array as a waveform.

Write Data State

Writes experimental data and comments to a text file corresponding to the active acquisition file name.

Write Acquisition State

Executes the "Analog In" "Read" state until the acquisition time has elapsed. A Boolean is sent to the "Digital Input/Output" case to control the lighting terminal corresponding to the particular instance in the elapsed time of the lighting array. Acquisition data is written to the user-defined file path while this state is active.

Reset AI State

Reinitializes the Analog In task.

Acquisition Panel Protocol

1. Navigate to file path.
2. Set electrode 1 and 2 voltage magnitudes and states (typ. 0.6-0.8 V) (Lien & Pietro, 1981).
3. Set acquisition time (hh:mm:ss).
4. Input $H_2$ calibration gas %, cell ct/chlorophyll, sample volume, temperature, and altitude.
5. Set lighting timing.
6. Allow probe relaxation until probe stabilizes.
7. Perform probe calibrations.
8. Inject sample and start acquisition.

Analysis Panel

Figure 14:
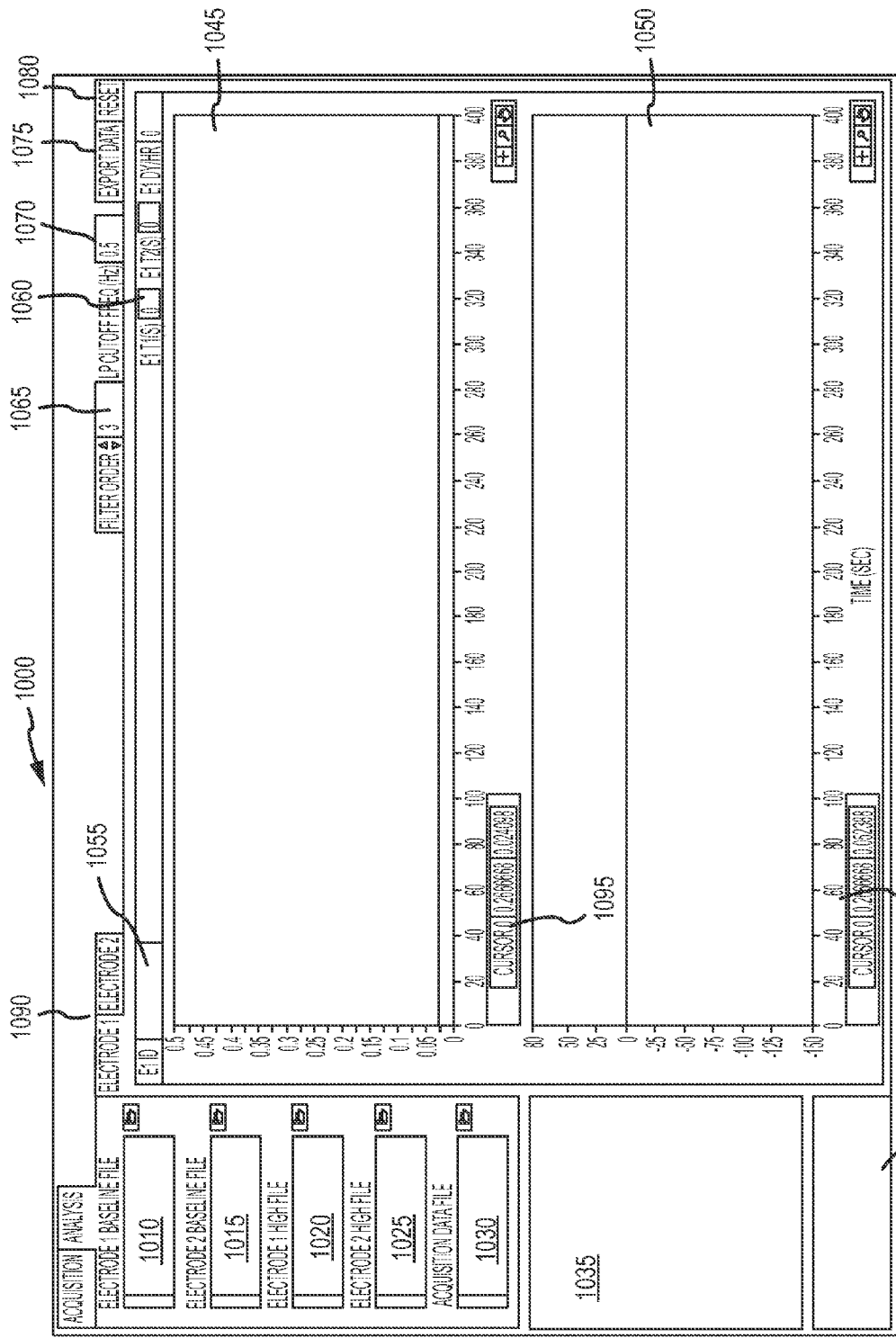
FIG. 14 shows an exemplary data analysis panel for software interfacing with the system of FIG. 1 according to aspects of the present disclosure.

FIG. 14 shows an exemplary data analysis panel for software interfacing with the present system. The analysis panel 1000 processes and displays data acquired by the acquisition program depicted in FIG. 12. The user may select acquisition and calibration files previously saved at boxes for Electrode 1 Baseline File 1010, Electrode 2 Baseline File 1015, Electrode 1 High File 1020, Electrode 2 High File 1025, Acquisition Data File 1030. After entry, the files are loaded into the program for analysis. The experimental information and comments are read by a VI, and displayed in separate fields 1035 and 1040, respectively. The program processes the data and displays it as μmmol gas*($\times 10^4$ cells or mg Chlorophyll$)^{-1}$ in an upper panel 1045 and rates of production, μmmol gas*($\times 10^4$ cells or mg Chlorophyll*hr$)^{-1}$ in a lower panel 1050. FIG. 14 shows that the Probe ID is displayed in field E1ID 1055. Data may be filtered according to filter order displayed in a filter order box 1065 and low-pass cutoff frequency displayed in box LP cutoff freq (Hz) 1070, which may be defined by the user (in some embodiments the defaults may be: filter order=3, low-pass cutoff frequency=0.5 Hz). Views of data for Electrode 1 and 2 may be toggled by clicking on tabs 1090 located above the ID box 1055. Values at any point in the plot are displayed in cursor fields 1095 1100, for amounts and rates, respectively by dragging a cursor over the graph. Pressing a write button 1075 writes the data to a single file. Pressing a reset button 1080 resets the program.

Each file is filtered by a low-pass, zero-phase lag butterworth filter with a low-pass frequency and order defined by the user. The 0% calibration file DC averages are subtracted from saturation calibration file DC averages and acquisition data to correct for DC offset caused by minor differences in probe quality and electrical component characteristics. Altitude, temperature, and $H_2$ calibration gas percentage are used to calculate equilibrium $O_2$ and $H_2$ concentrations at specified atmospheric conditions. Atmospheric pressure is calculated as:

$$\ln P = 5.25 * \ln\left(1 - \frac{h}{44.3}\right)$$

Where h is altitude in kilometers and P is in atmospheres. Partial pressure of water vapor is calculated with an approximation of the Goff-Gratch equation:

$$\ln P_{wv} = 11.8571 - \left(\frac{3840.7}{T}\right) - \left(\frac{216961}{T^2}\right)$$

Where T is temperature in Kelvin and the partial pressure of water ($P_{wv}$) is in atmospheres. Partial pressure of $H_2$ and $O_2$ are calculated as a percentage of the difference between atmospheric pressure and water vapor partial pressure:

$$PP_{H2} = \left(\frac{H_{2calgas}\ \%}{100}\right) * (P - P_{wv})$$

$$PP_{O2} = .2094 * (P - P_{wv})$$

The Henry coefficient, $k_H$, is calculated using a form of the van 't Hoff equation with compensation for temperature:

$$k_H(T) = k_H(T_{std}) * e^{\left(-C*\left(\frac{1}{T}-\frac{1}{T_{std}}\right)\right)}$$

Where T is temperature in Kelvin, $T_{std}$ is 298° K, $k_H(T_{std})$ is Henry's coefficient of a gas at 298° K ($k_{H,O2}$=769.23 L*atm*mol$^{-1}$, $k_{H,H2}$=1282.05 L*atm*mol$^{-1}$), and C is a unitless constant ($C_{O2}$=1700, $C_{H2}$=500). $O_2$ and $H_2$ equilibrium gas concentrations are calculated in mol*L$^{-1}$:

$$c = \frac{PP}{k_H}$$

A correction factor for salinity is calculated from a portion of the Bunsen solubility coefficient equation (Crozier, Yamamoto, 1974):

$$\beta = e^{\left(S+\left(B_1+B_2+\left(\frac{T}{100}\right)+B_2+\left(\frac{T}{100}\right)^2\right)\right)}$$

where S is salinity in ppt, T is temperature in Kelvin, and B1-3 are described in the above citation for both oxygen and hydrogen solubility.

Data are then scaled between the baseline and saturation benchmark DC averages and converted to μmmol gas*(×10$^4$ cells or mg Chlorophyll)$^{-1}$ using sample volume and cell count/chlorophyll data taken from the data file. Its derivative is taken to obtain hourly rates of gas development. User selected time intervals can be entered in two separate fields on each graph tab and 2-point rates can be calculated using linear interpolation. Processed data can then be exported to a .lvm (LabVIEW® measurement) file.

Analysis State Machine

Figure 15:
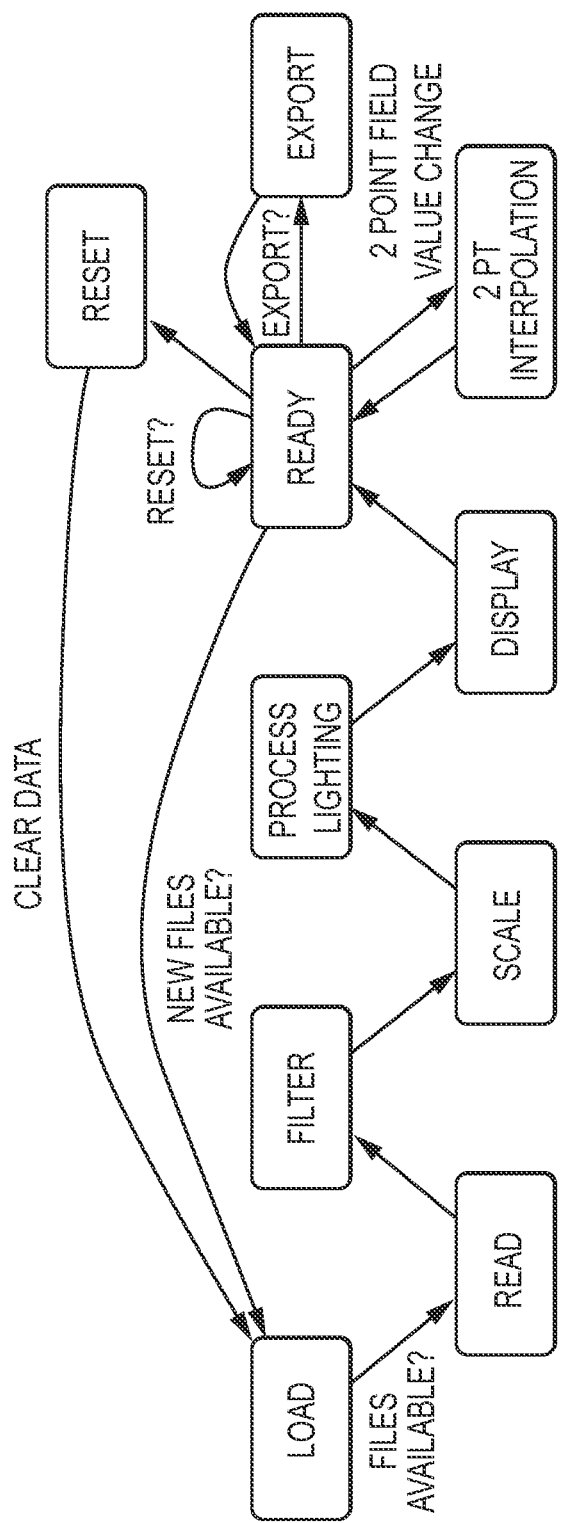
FIG. 15 is a flow diagram for the analysis state machine that may be used with aspects of the system of FIG. 1.

In accordance with some embodiments, an analysis state machine for the device is illustrated in FIG. 15. The various states are described in greater detail below.

Load State

The load state repeats until the four calibration files (*-E1B.lvm, *-E2B.lvm, *-E1H.lvm, *-E2H.lvm) and the acquisition file (*-ACQ.lvm) are available. It then passes the file paths to the read state.

Read State

Each specified file is loaded along with the acquisition's corresponding data file (*-DAT.lvm) and lighting file (*-LIT.lvm). The experimental data is parsed from the data file.

Filter State

Figure 16A:
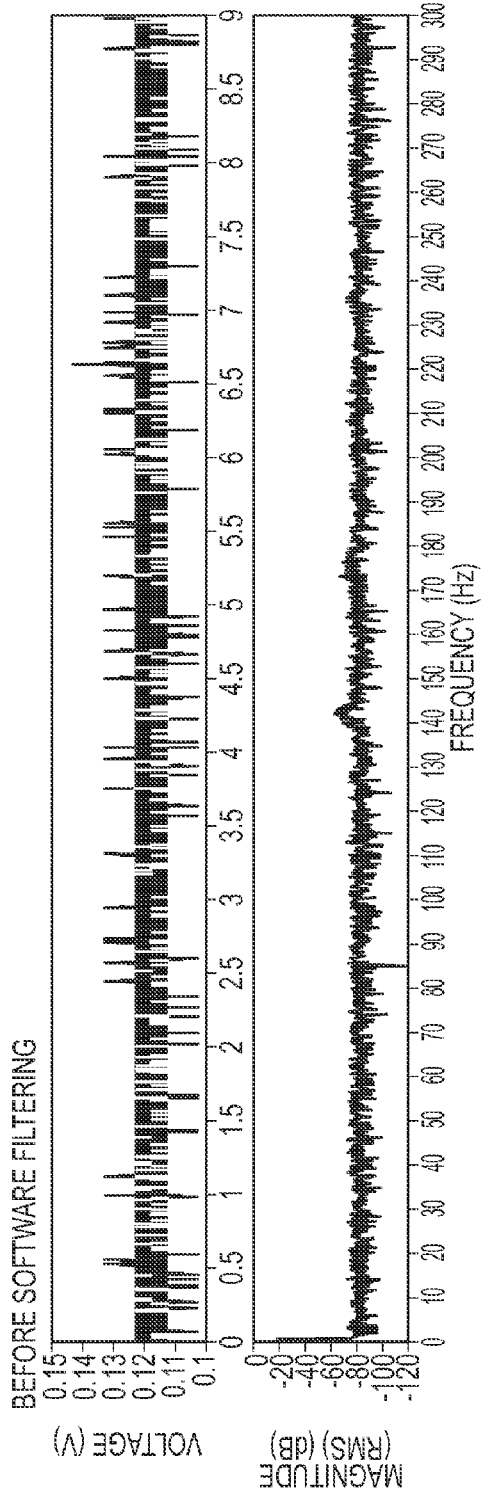
FIGS. 16A-16B depict a display of acquisition data showing voltage vs. frequency and magnitude vs. frequency without connected probes before (FIG. 16A) and after (FIG. 16B) filtering according to aspects of the present disclosure.
Figure 16B:
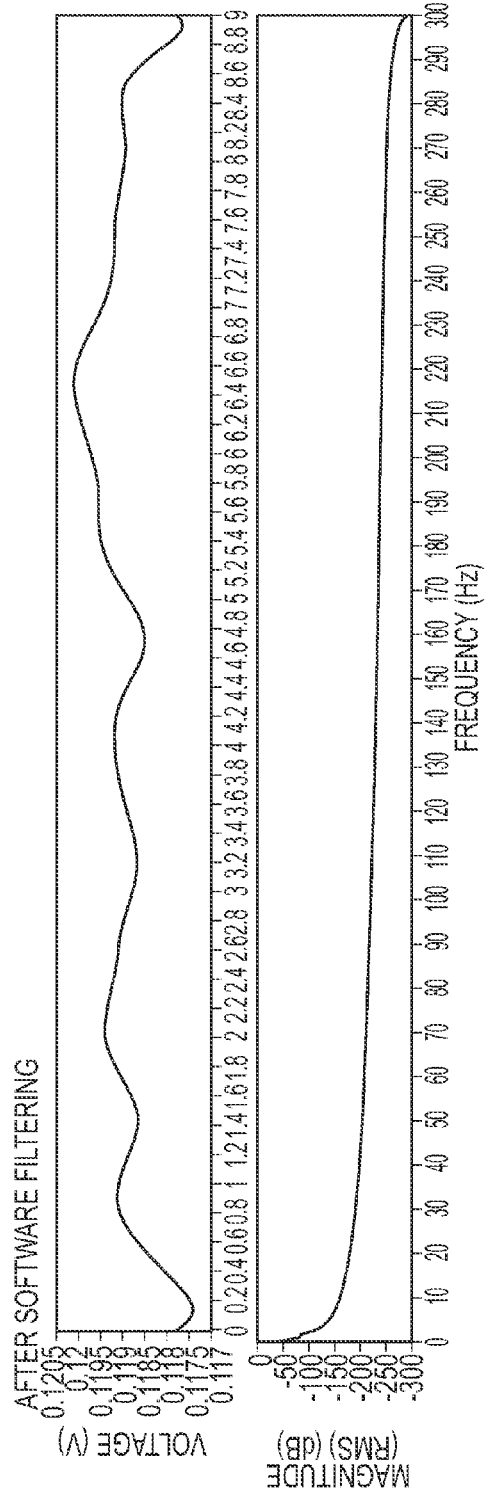

Calibration and acquisition files may be filtered using a low-pass, zero-phase lag Butterworth filter. DC values are read from each calibration file. In some embodiments, little or no filtering may be implemented considering the low level of noise present in the raw data. However external ambient noise from nearby electromagnetic sources may affect signal quality. Therefore, filtering is meant as a safeguard against any noise introduced to the system that is not filtered by hardware. FIGS. 16A-16B show a sample acquisition without connected probes. FIG. 16A illustrates the data before software filtering and FIG. 16B illustrates the data after software filtering. The data in FIGS. 16A-16B were taken at 600 Hz and filtered using a 0.5 Hz, 3$^{rd}$ order, low-pass, zero-phase lag Butterworth filter (FIG. 16B). Higher order noise (29.4 mV p-p) is completely eliminated from the hardware-filtered signal, and only very minor aberrations are observed in the filtered signal (Δ2.5 mV).

Scale State

DC offset is subtracted from the saturation and acquisition files, and the acquisition data is scaled with the saturation files and experimental data as described above.

Process Lighting State

The light array data is parsed into two separate arrays, a high-on and a high-off array. These two arrays are used to indicate on each graph when the light is on or off with a green or red line at the y=0 level.

Display State

Acquired and experimental data are displayed on the front panel.

Ready State

If new files are specified in their corresponding file path fields, the load state is initialized to process the new data. Time values can be entered in the upper right fields to determine gas development rates in the "2 Pt Interpolation" state. Data can also be exported to a separate file.

2 Pt Interpolation State

Y-values are obtained at each user-specified X-value and the slope between the two XY pairs is reported.

Export State

Saves data to a user-selected file path.

Example Application

Experiment Setup

Device (system) performance was tested by $H_2$ linearity measurements and quantification of error arising from experimental parameters and DAQ resolution. The acquired data was tested using typical experiment methods particular to an algal $H_2$-photoproduction investigation, using *Chlamydomonas reinhardtii*, a commonly studied algae species, and compared with data acquired using previous assaying methods.

Figure 17:
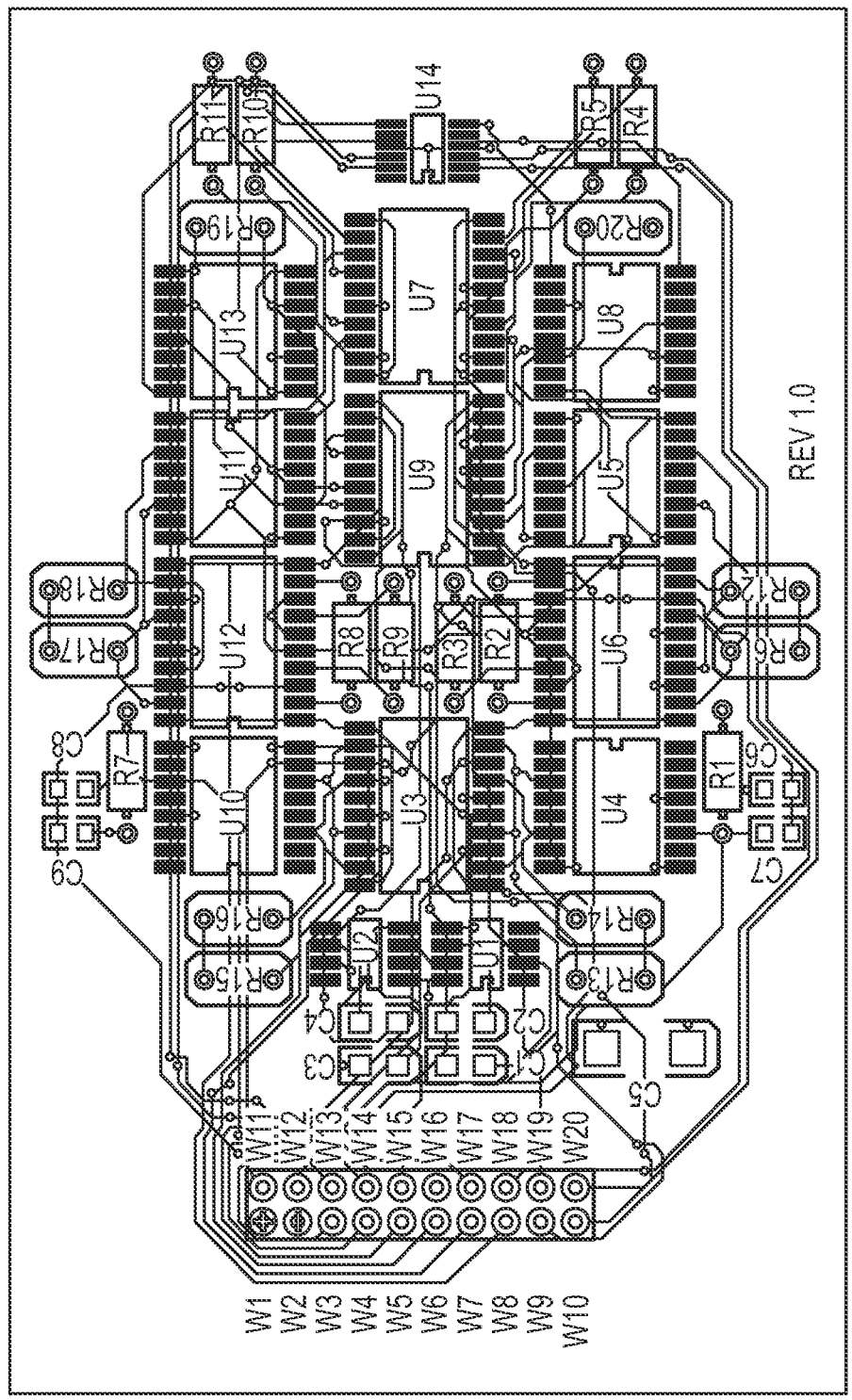
FIG. 17 is an exemplary Circuit Printed Circuit Board (PCB) Layout for use with aspects of the presently described system.
Figure 18:
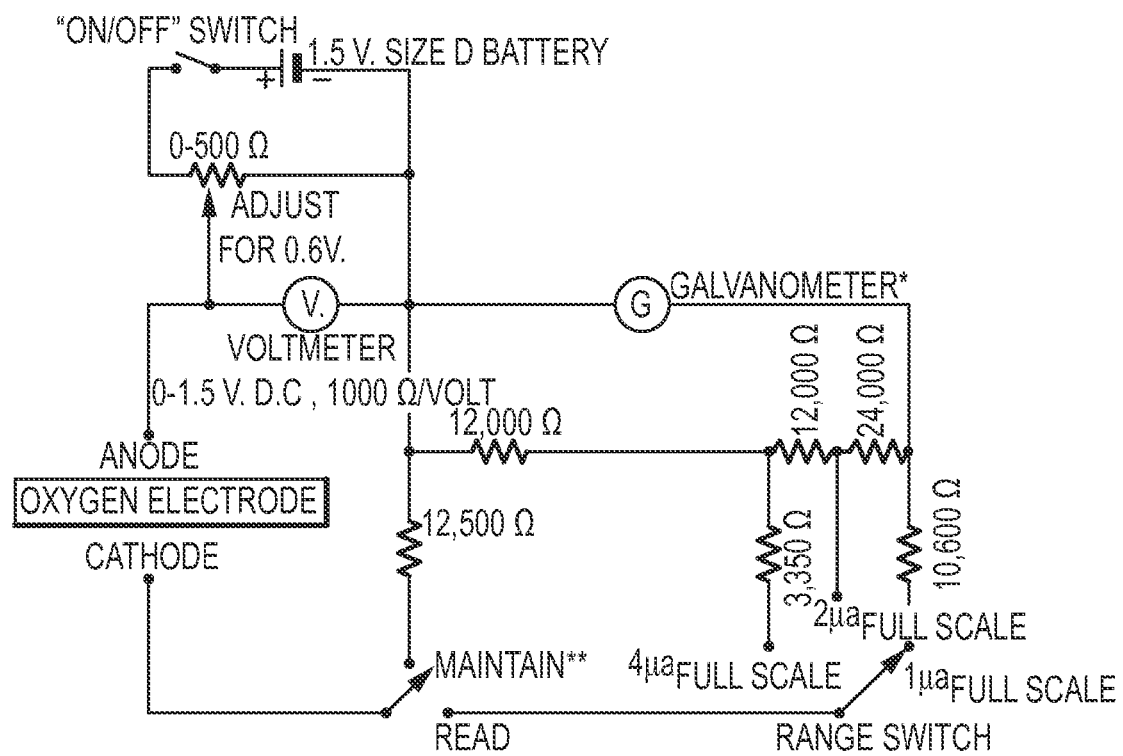
FIG. 18 is a diagram of an exemplary Clark Polarograph Circuit for use with aspects of the present system.
Figure 19C:
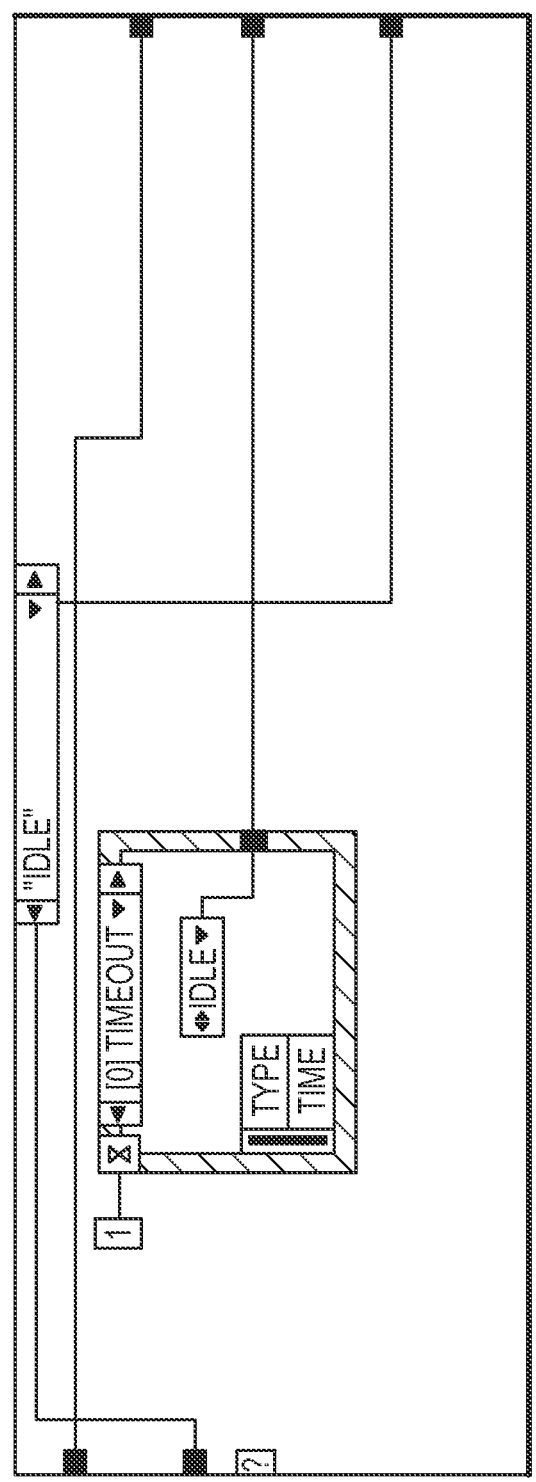
FIG. 19C depicts an "idle" state in LABVIEW® programming for an exemplary embodiment of an analog out case of the presently claimed system.
Figure 19D:
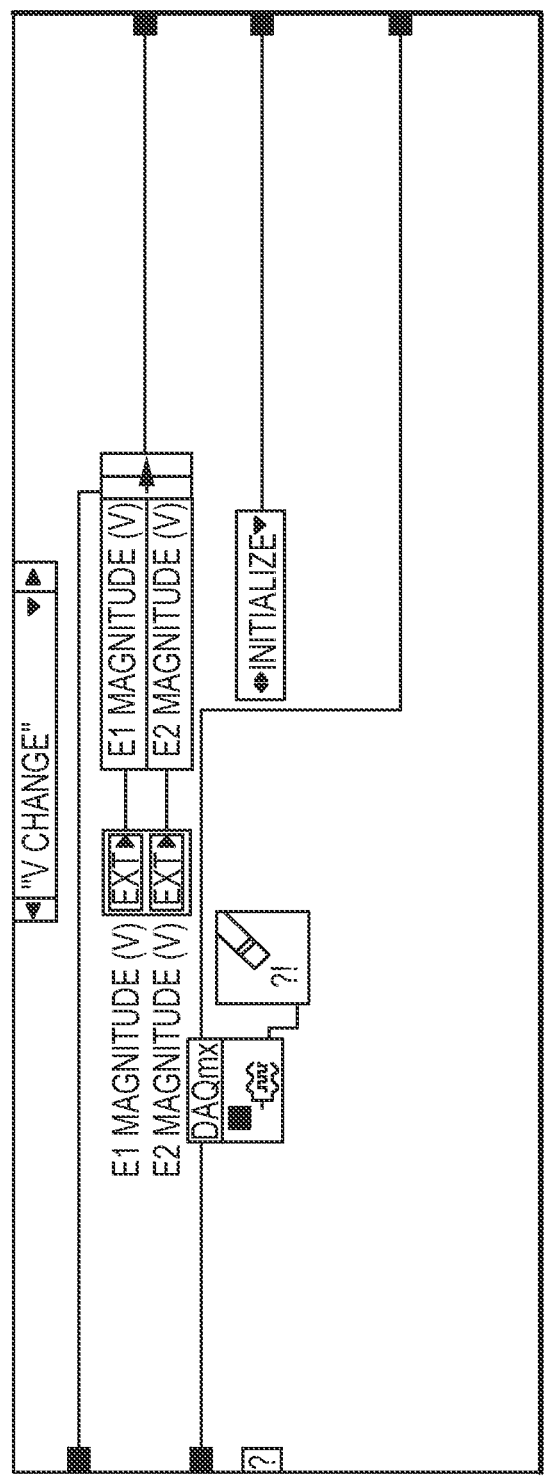
FIG. 19D depicts a "v change" state in LABVIEW® programming for an exemplary embodiment of an analog out case of the presently claimed system.
Figures 1, 20A:
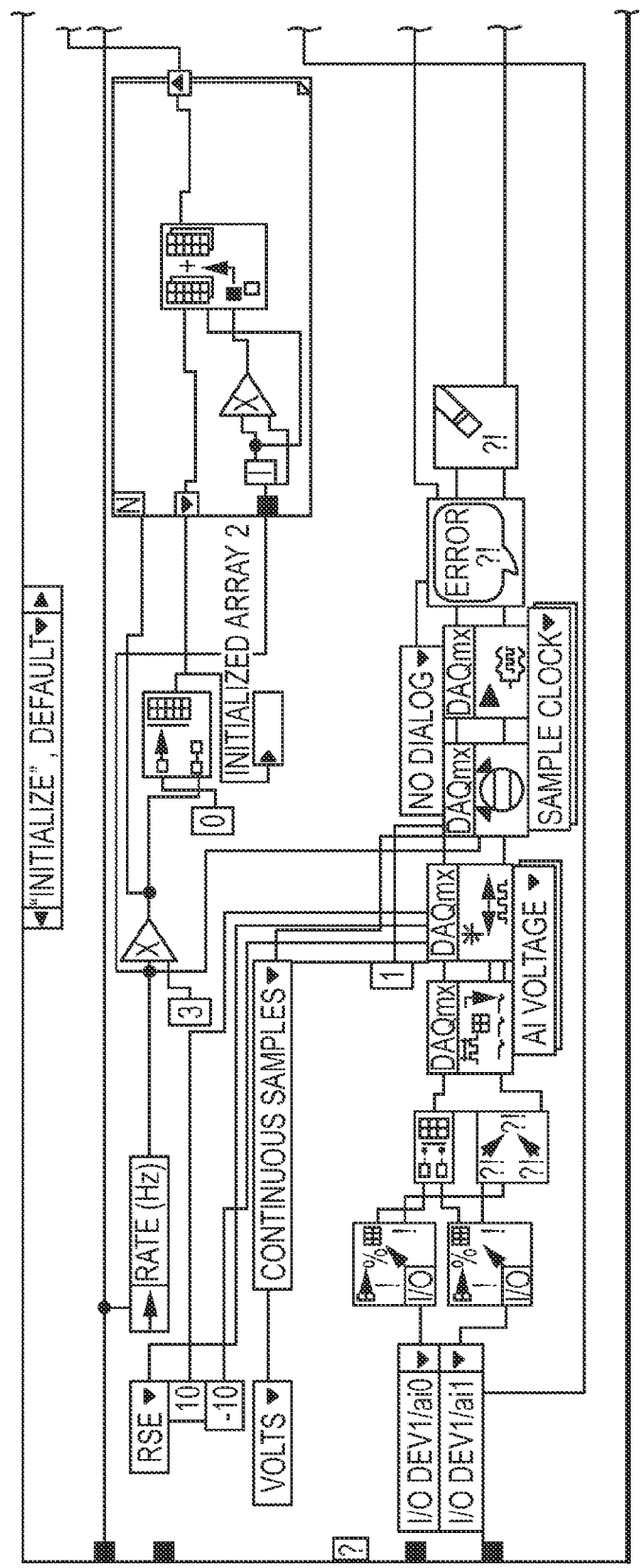
FIG. 20A depicts an "initialize" state in LABVIEW® programming for an exemplary embodiment of an analog in case of the presently claimed system.
Figures 2, 20A:
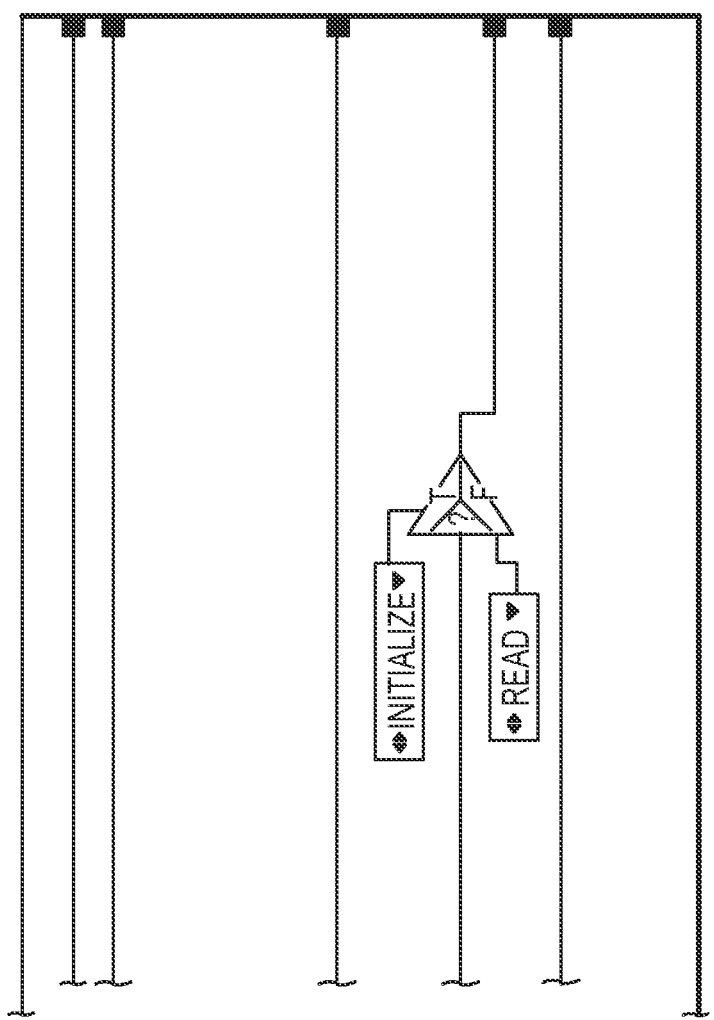
Figure 20B:
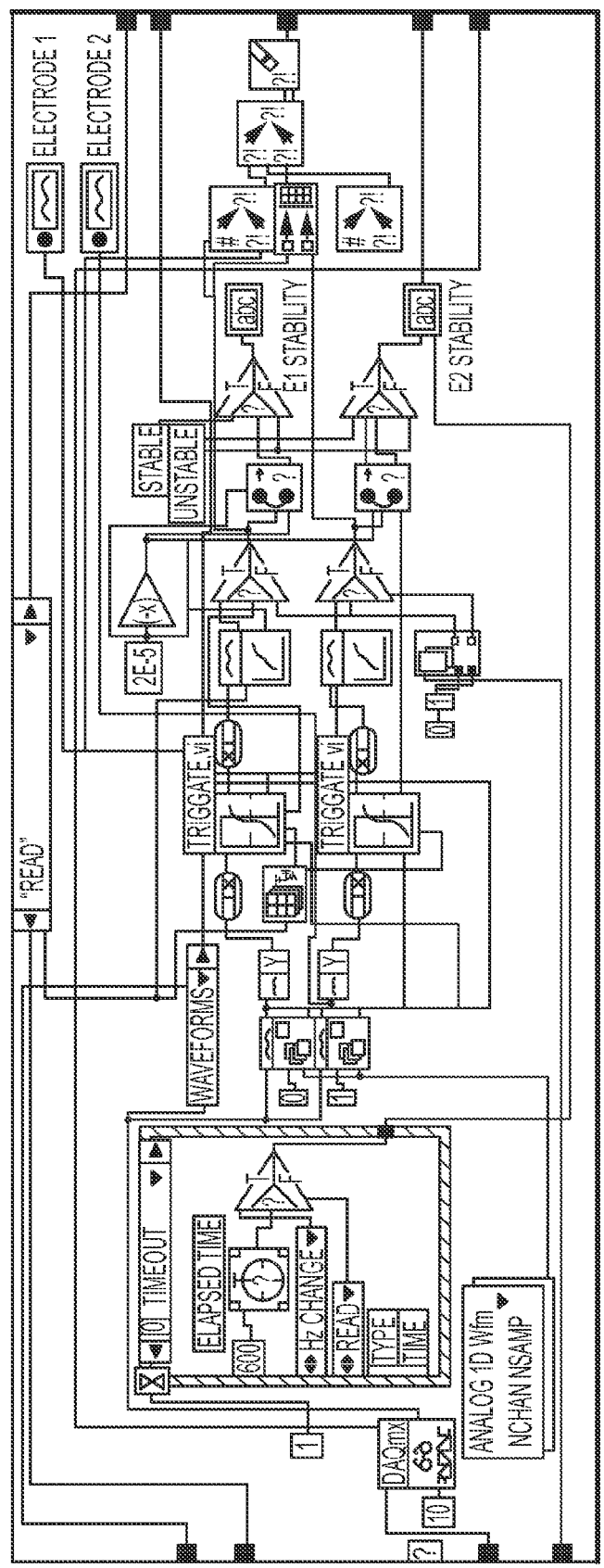
FIG. 20B depicts an "read" state in LABVIEW® programming for an exemplary embodiment of an analog in case of the presently claimed system.
Figure 20C:
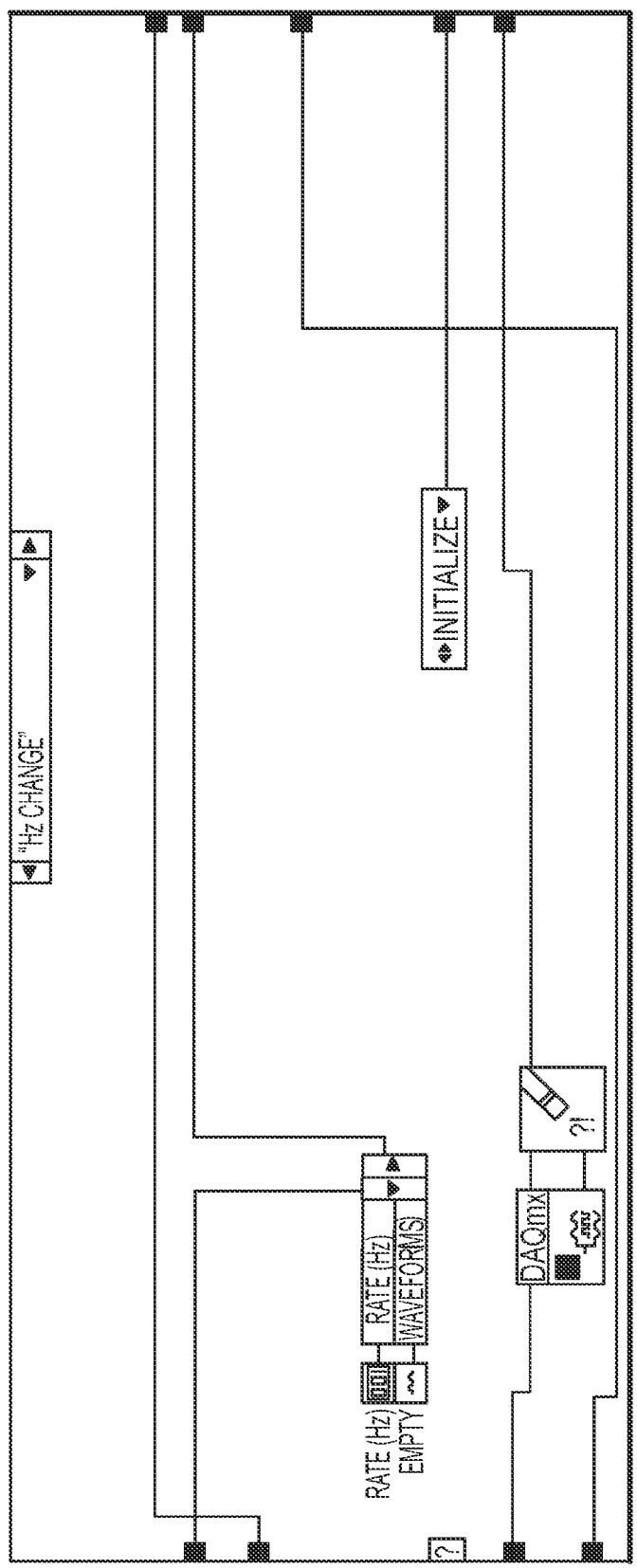
FIG. 20C depicts an "Hz change" state in LABVIEW® programming for an exemplary embodiment of an analog in case of the presently claimed system.
Figure 21A:
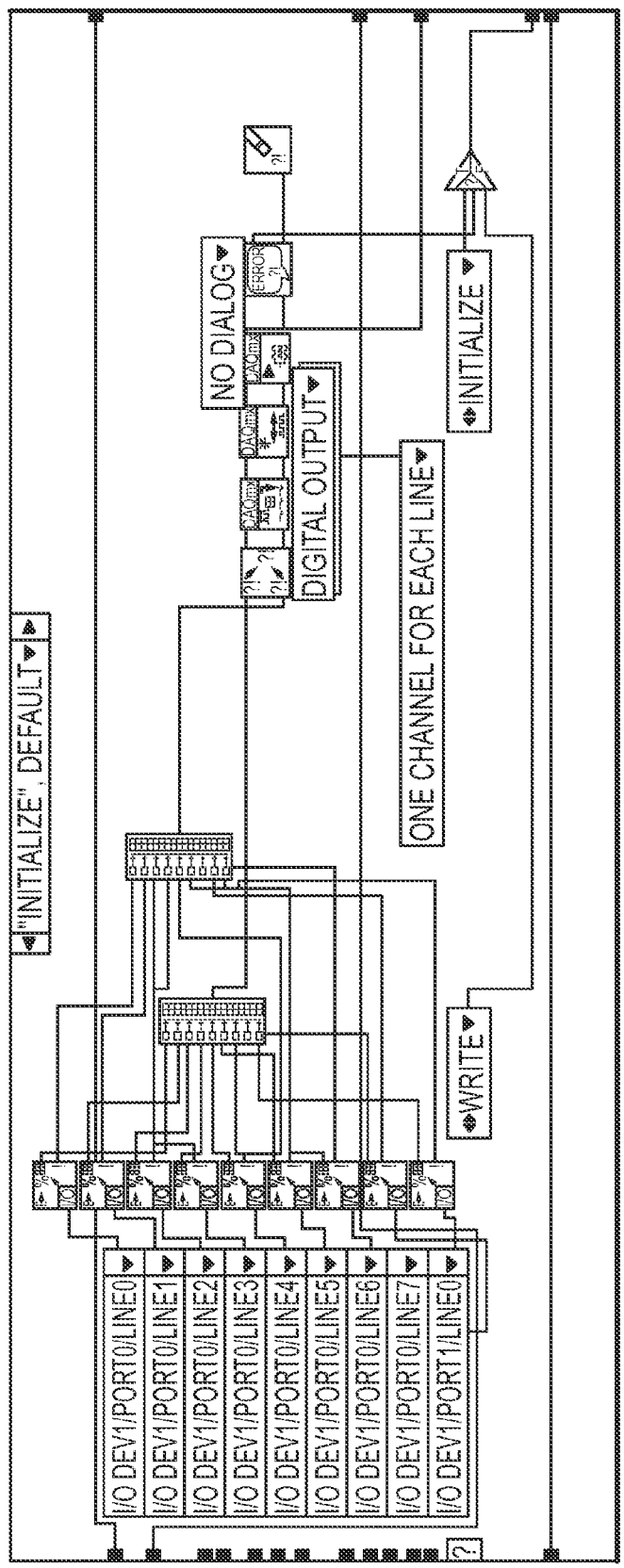
FIG. 21A depicts an "initialize" state in LABVIEW® programming for an exemplary embodiment of a digital out case of the presently claimed system.
Figure 21B:
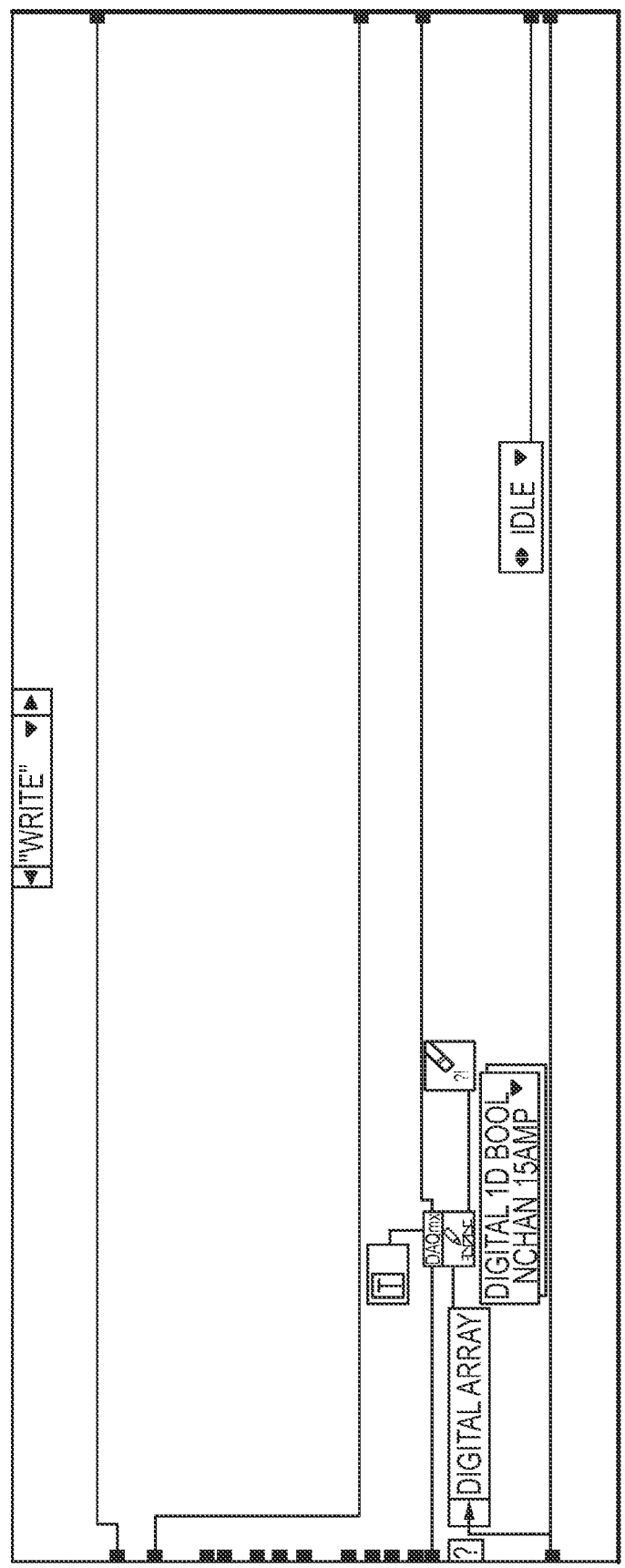
FIG. 21B depicts a "write" state in LABVIEW® programming for an exemplary embodiment of a digital out case of the presently claimed system.
Figure 21C:
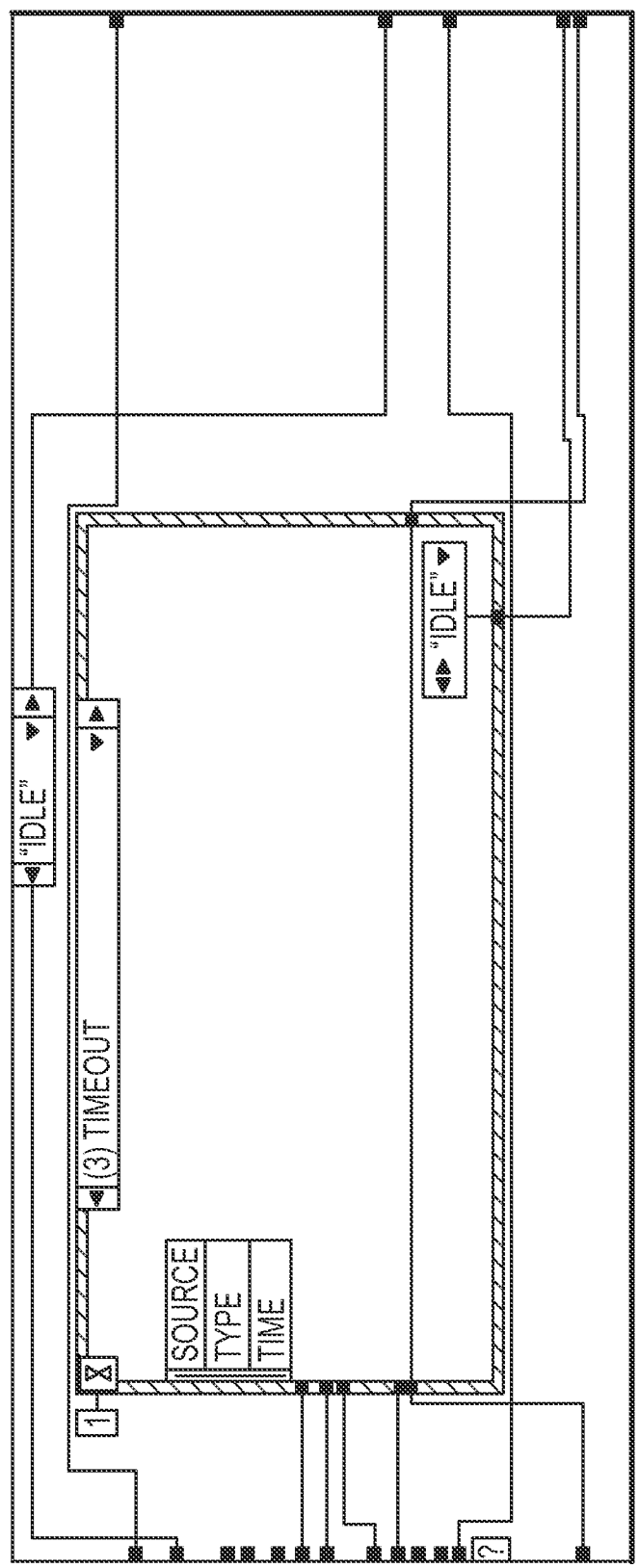
FIG. 21C depicts an "idle" state in LABVIEW® programming for an exemplary embodiment of a digital out case of the presently claimed system.
Figure 21D:
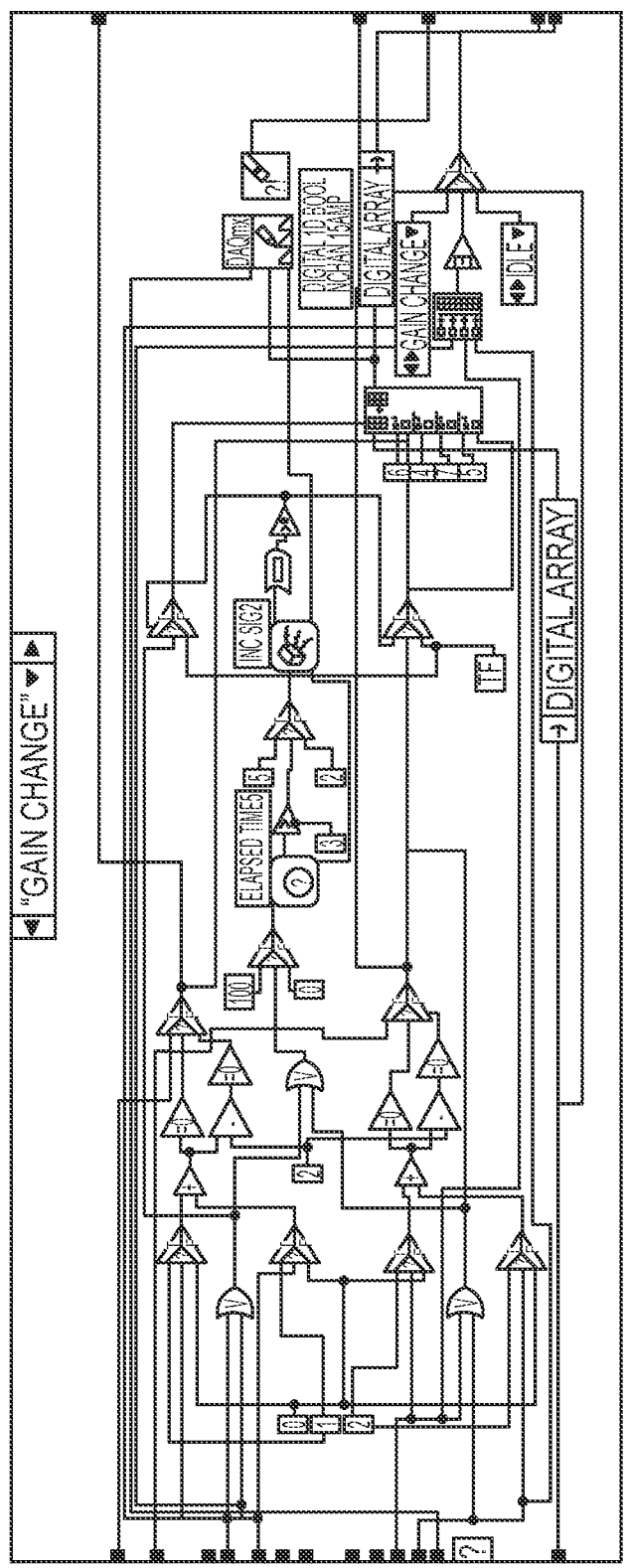
FIG. 21D depicts a "gain change" state in LABVIEW® programming for an exemplary embodiment of a digital out case of the presently claimed system.
Figure 21E:
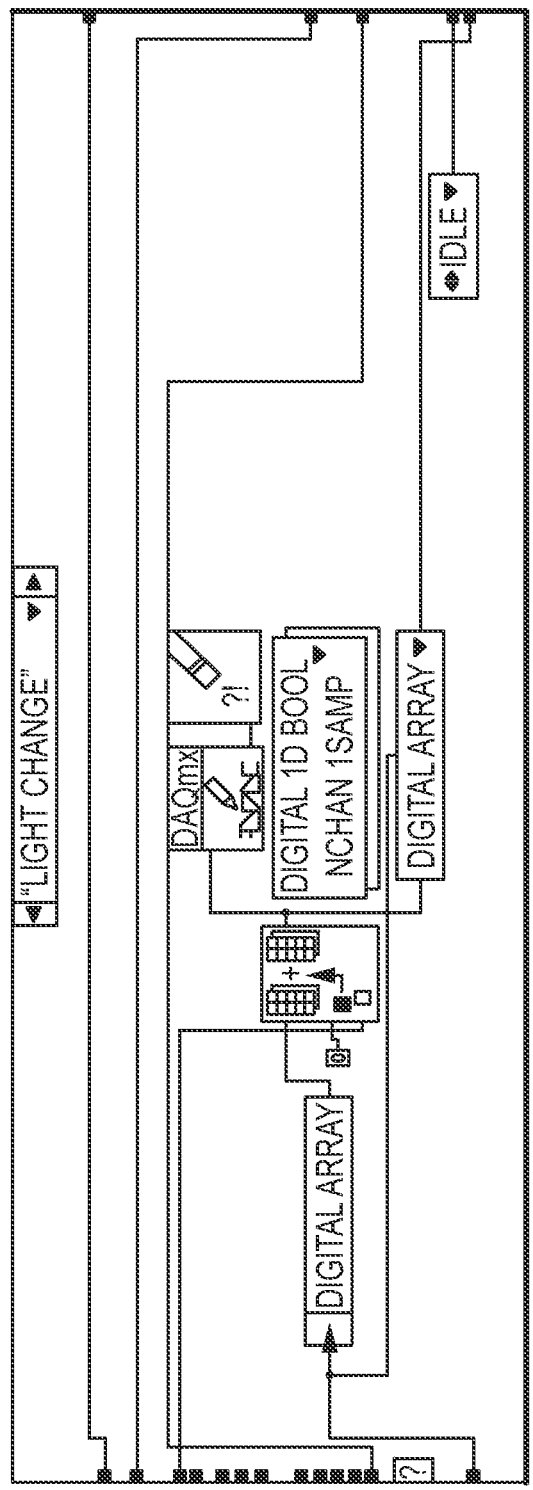
FIG. 21E depicts a "light change" state in LABVIEW® programming for an exemplary embodiment of a digital out case of the presently claimed system.
Figure 22A:
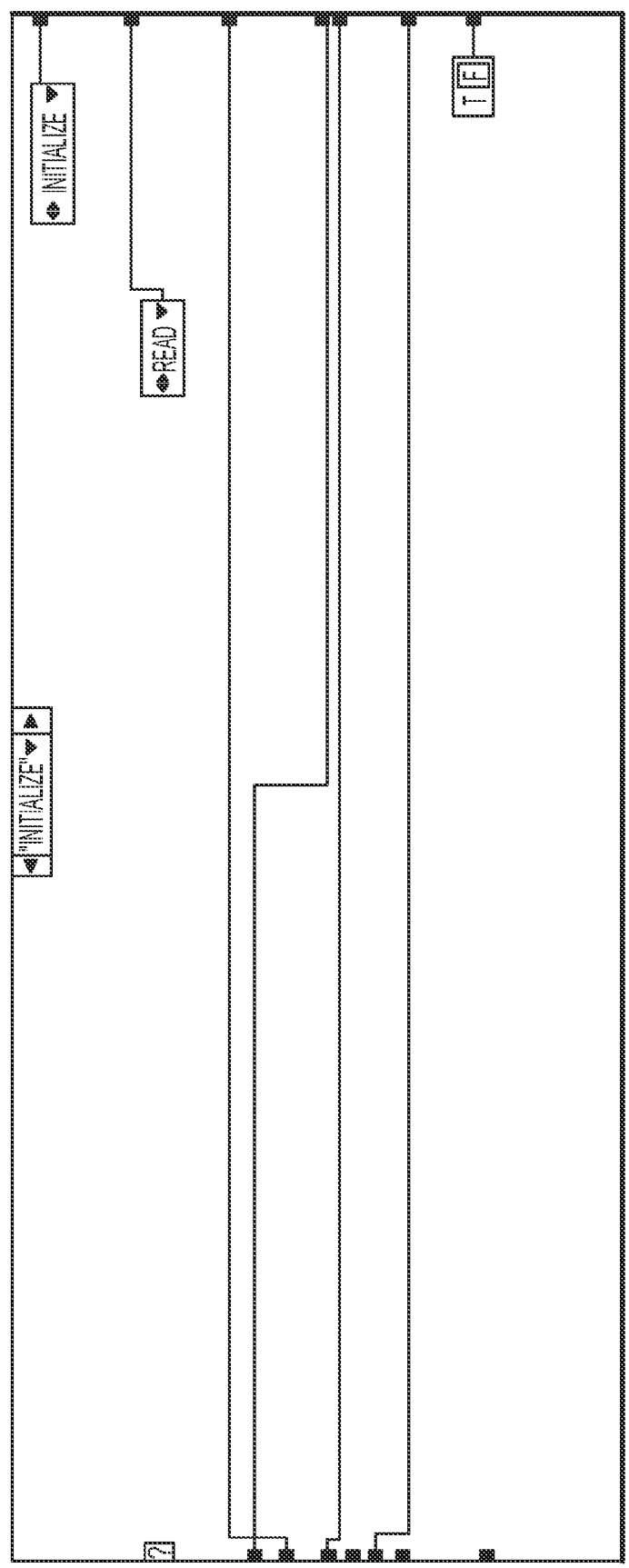
FIG. 22A depicts an "initialize" state in LABVIEW® programming for an exemplary embodiment of an acquire case of the presently claimed system.
Figure 22B:
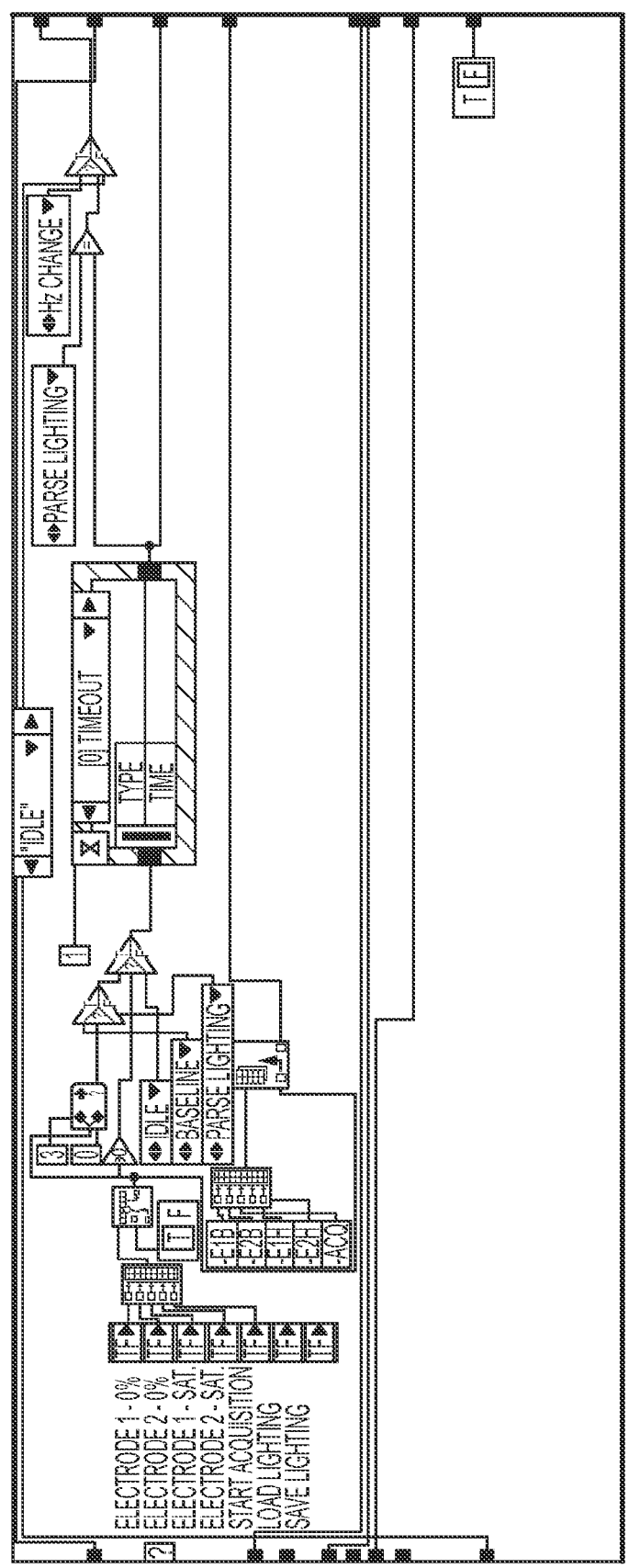
FIG. 22B depicts an "idle" state in LABVIEW® programming for an exemplary embodiment of an acquire case of the presently claimed system.
Figure 22C:
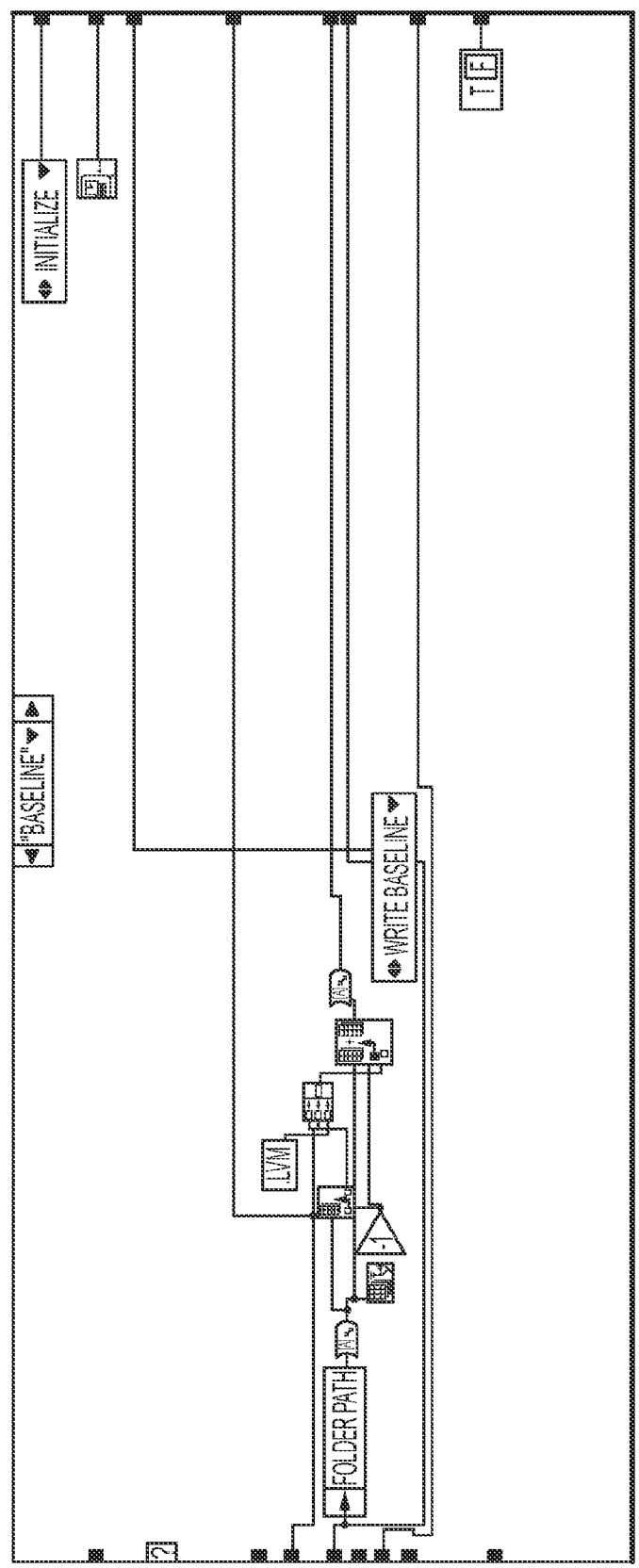
FIG. 22C depicts a "baseline" state in LABVIEW® programming for an exemplary embodiment of an acquire case of the presently claimed system.
Figure 22D:
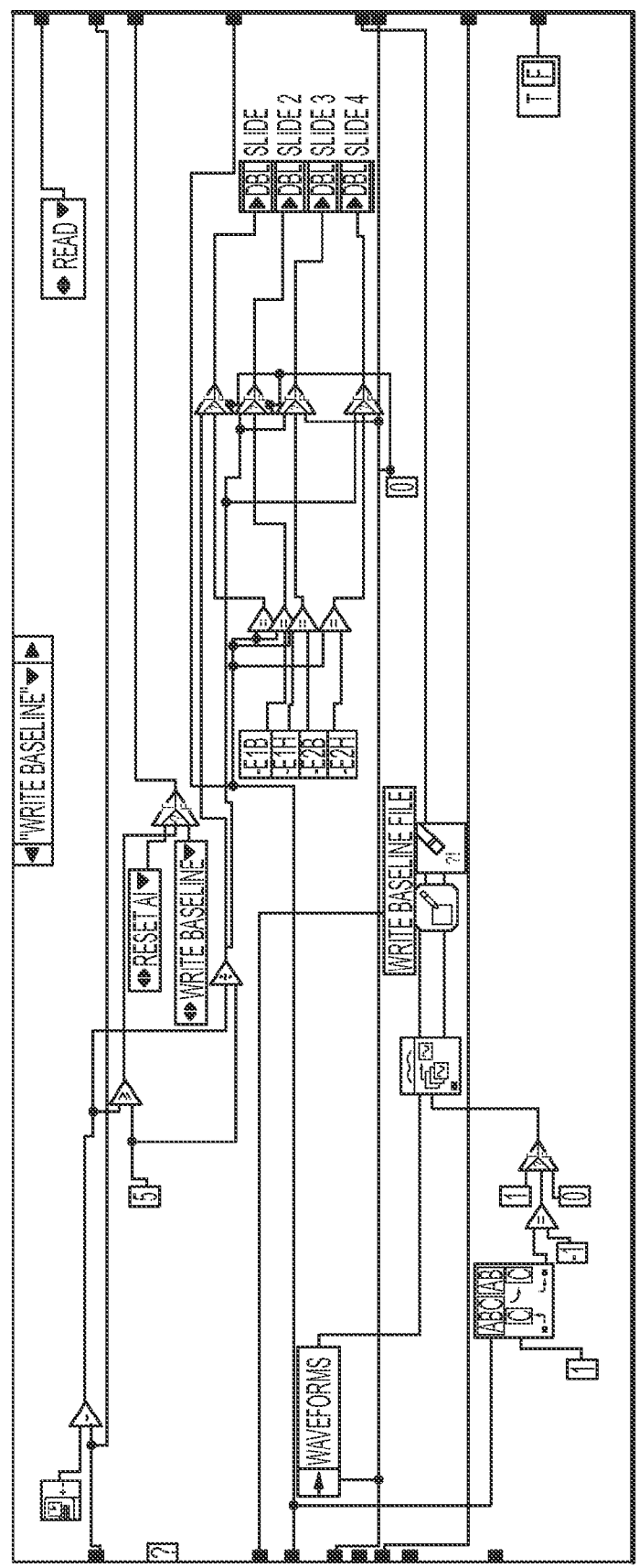
FIG. 22D depicts a "write baseline" state in LABVIEW® programming for an exemplary embodiment of an acquire case of the presently claimed system.
Figure 22E:
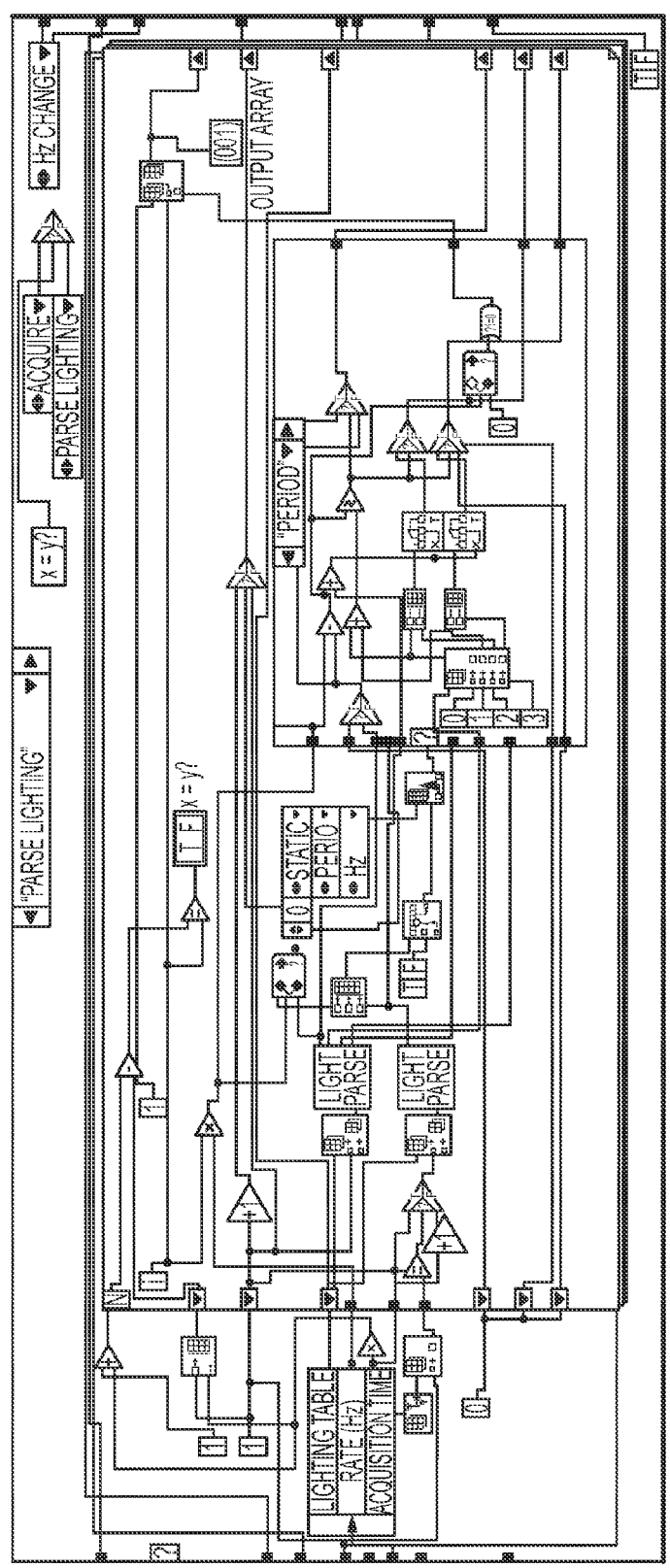
FIG. 22E depicts a "parse lighting" state in LABVIEW® programming for an exemplary embodiment of an acquire case of the presently claimed system.
Figure 22F:
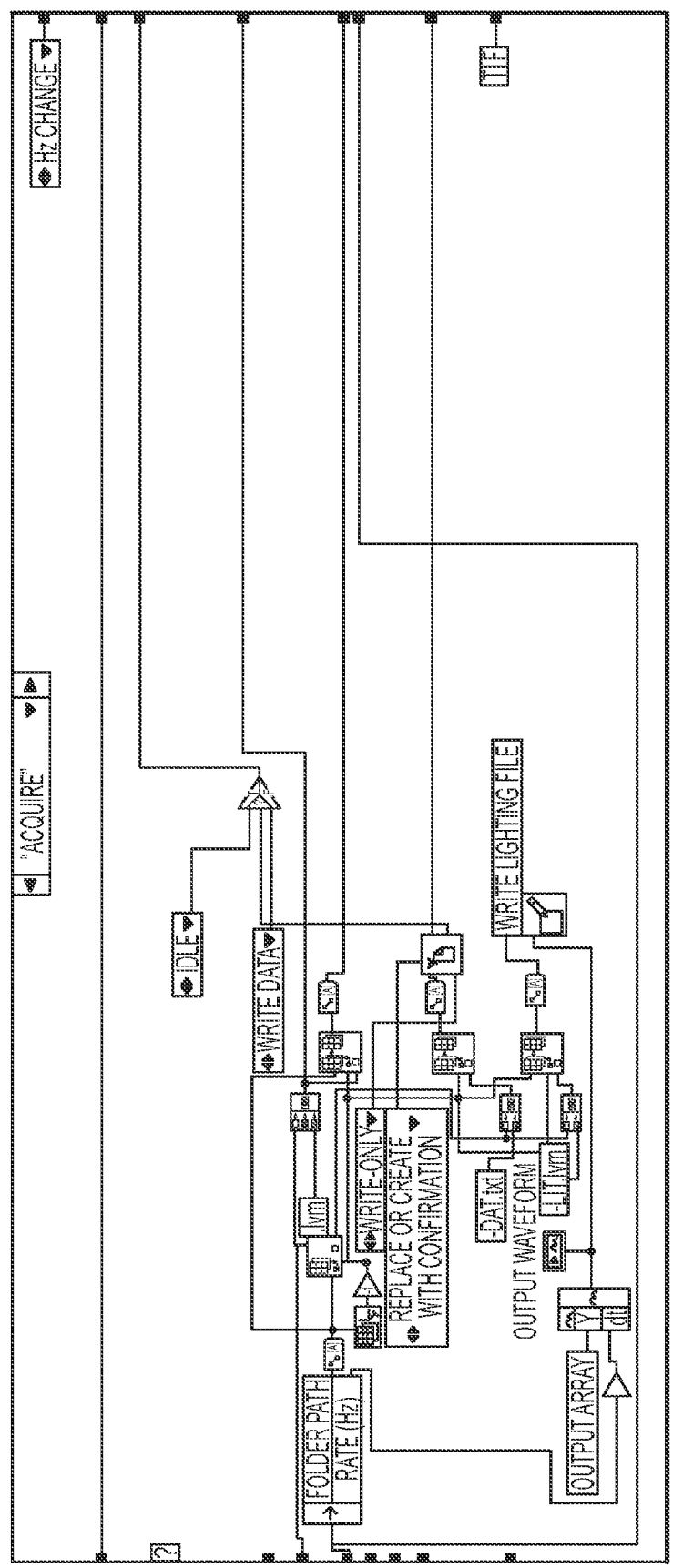
FIG. 22F depicts an "acquire" state in LABVIEW® programming for an exemplary embodiment of an acquire case of the presently claimed system.
Figure 22G:
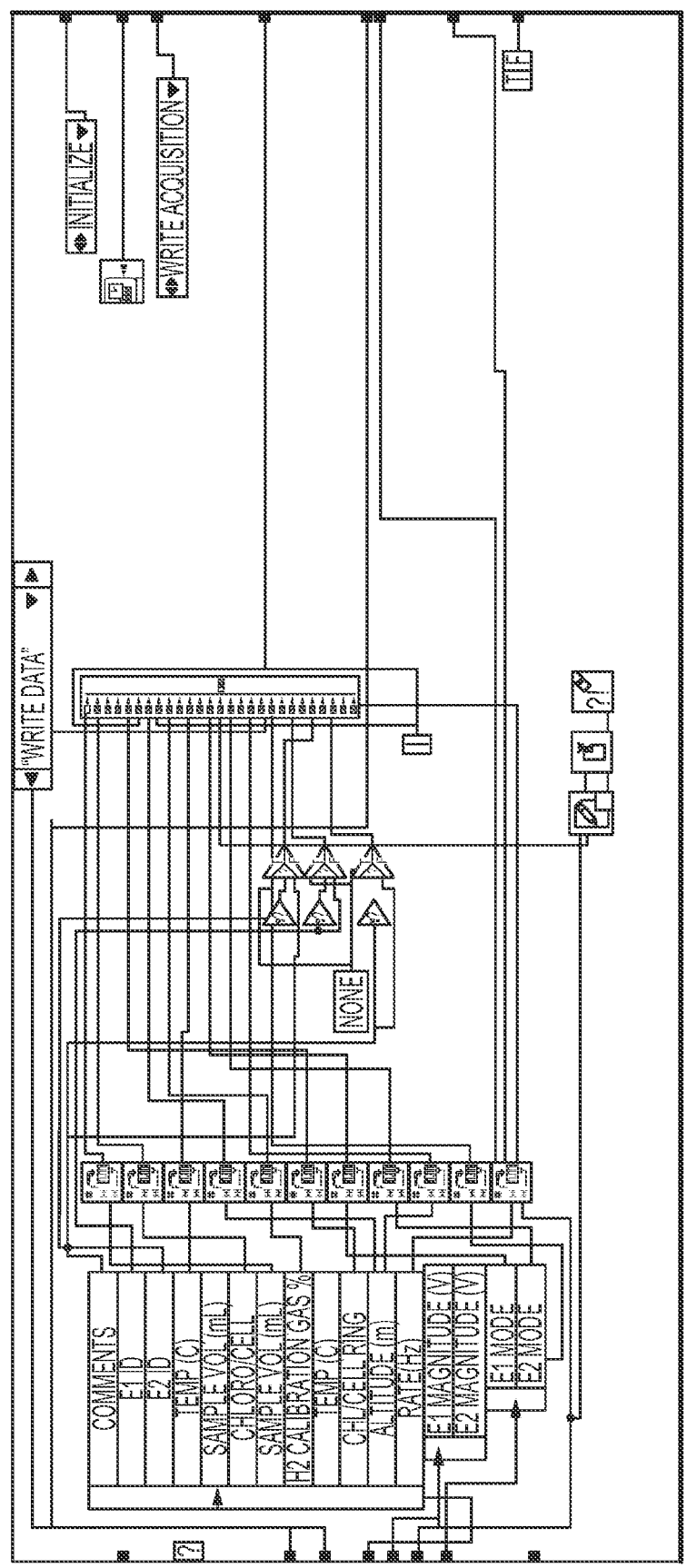
FIG. 22G depicts a "write data" state in LABVIEW® programming for an exemplary embodiment of an acquire case of the presently claimed system.
Figure 22H:
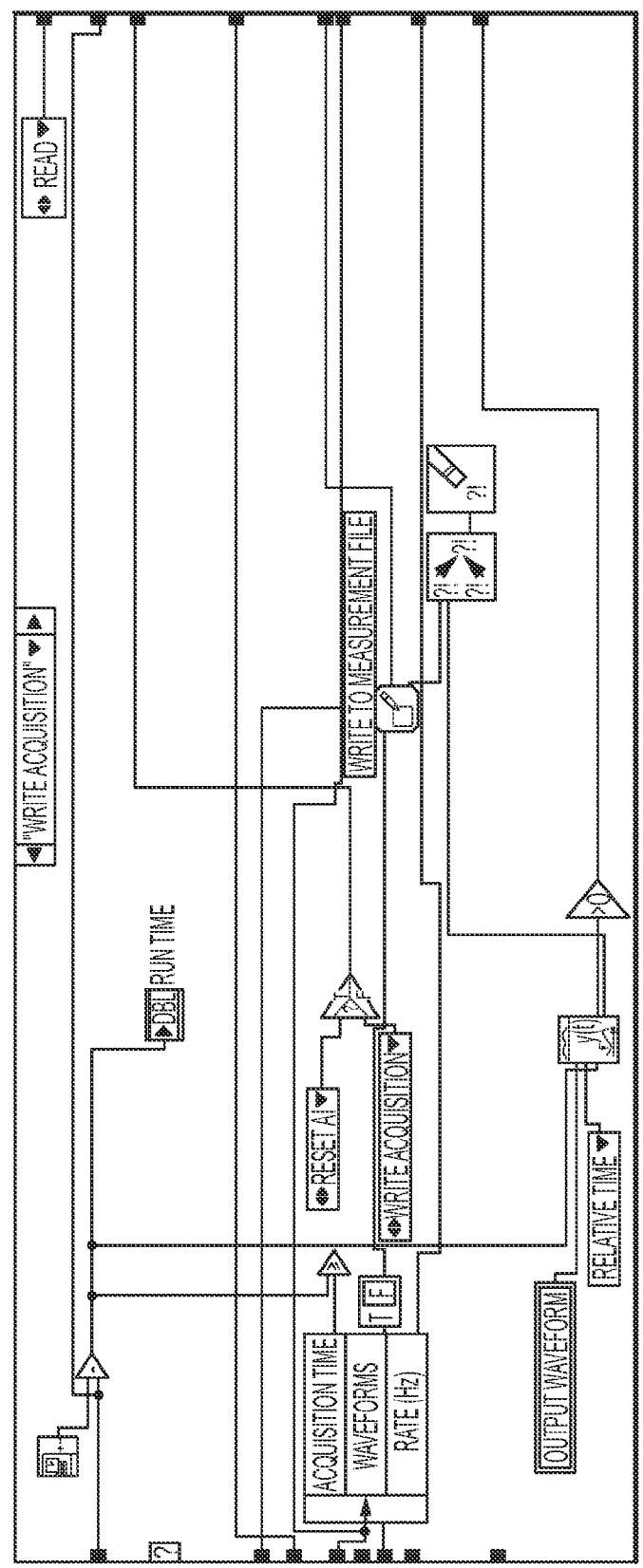
FIG. 22H depicts a "write acquisition" state in LABVIEW® programming for an exemplary embodiment of an acquire case of the presently claimed system.
Figure 23A:
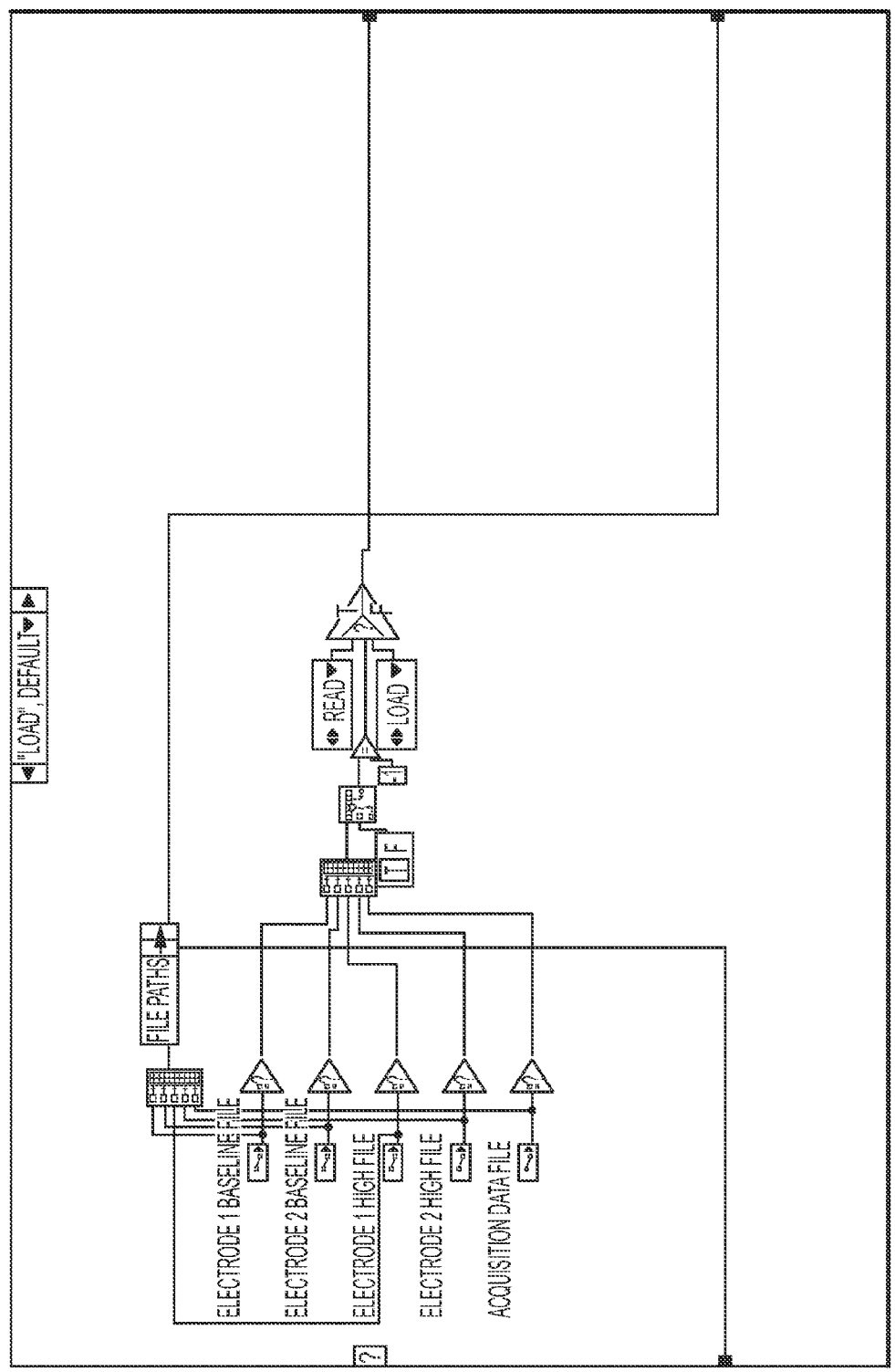
FIG. 23A depicts a "load" state in LABVIEW® programming for an exemplary embodiment of an analysis case in an analysis state machine of the presently claimed system.
Figure 23B:
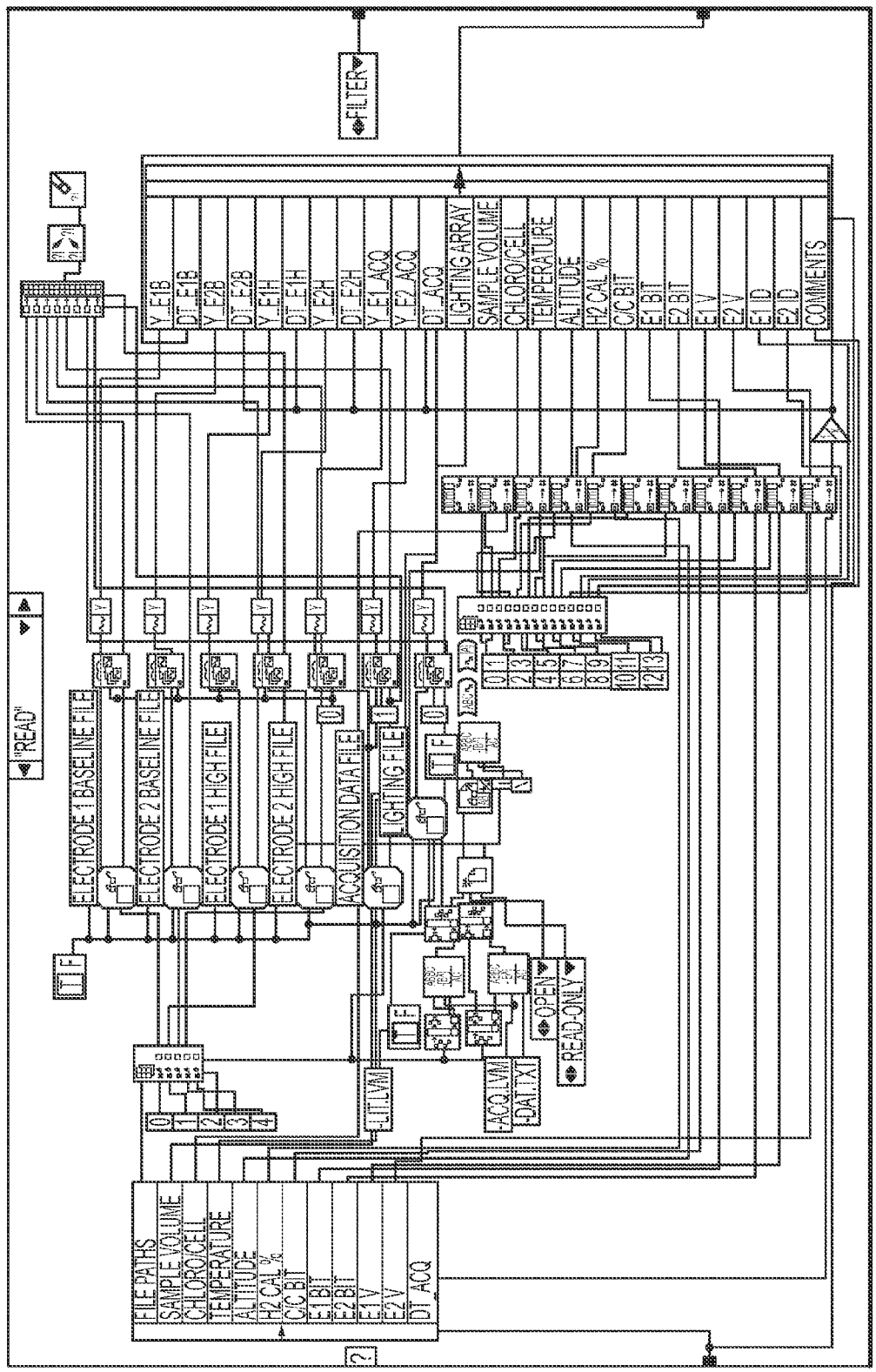
FIG. 23B depicts a "read" state in LABVIEW® programming for an exemplary embodiment of an analysis case in an analysis state machine of the presently claimed system.
Figure 23C:
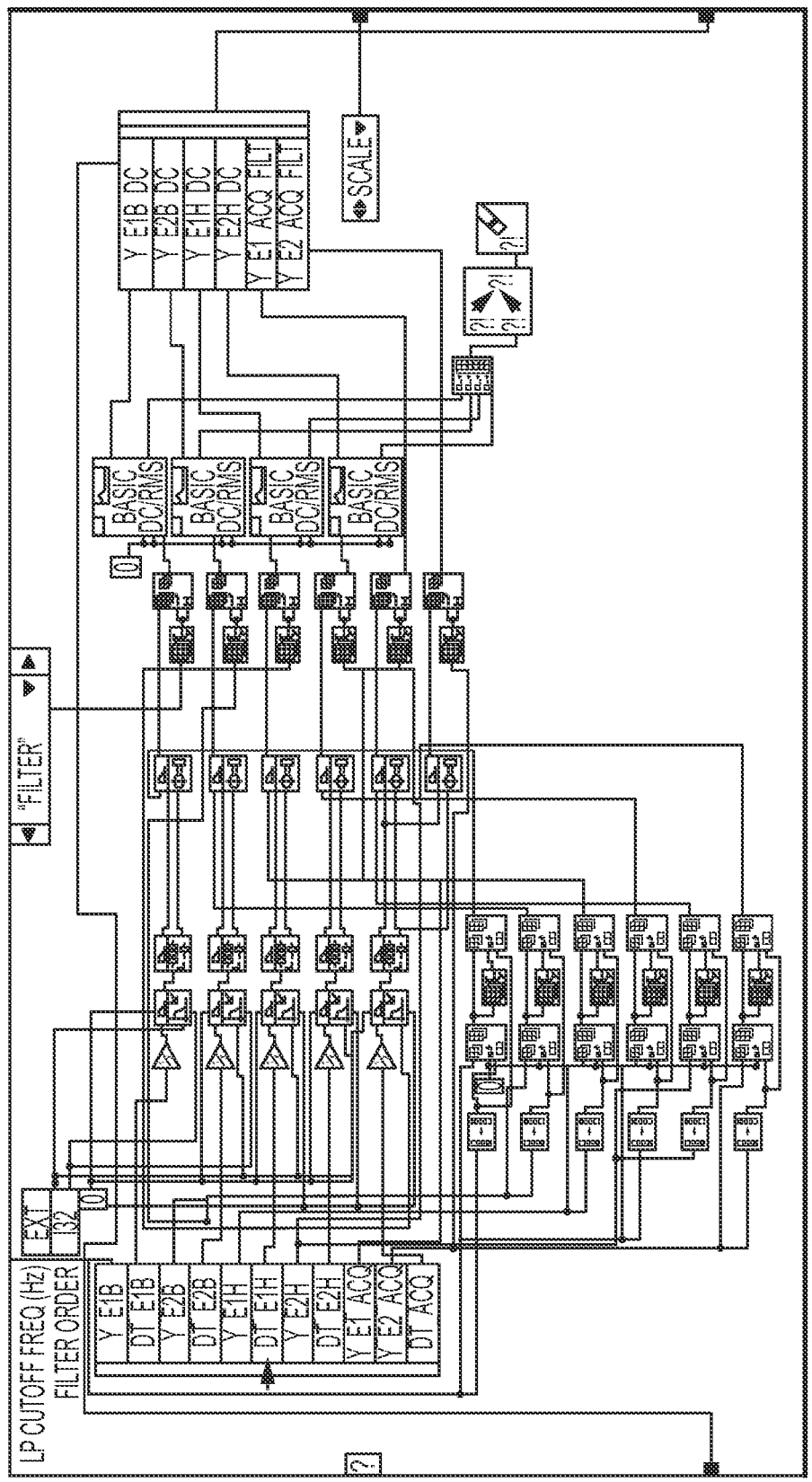
FIG. 23C depicts a "filter" state in LABVIEW® programming for an exemplary embodiment of an analysis case in an analysis state machine of the presently claimed system.
Figure 23D:
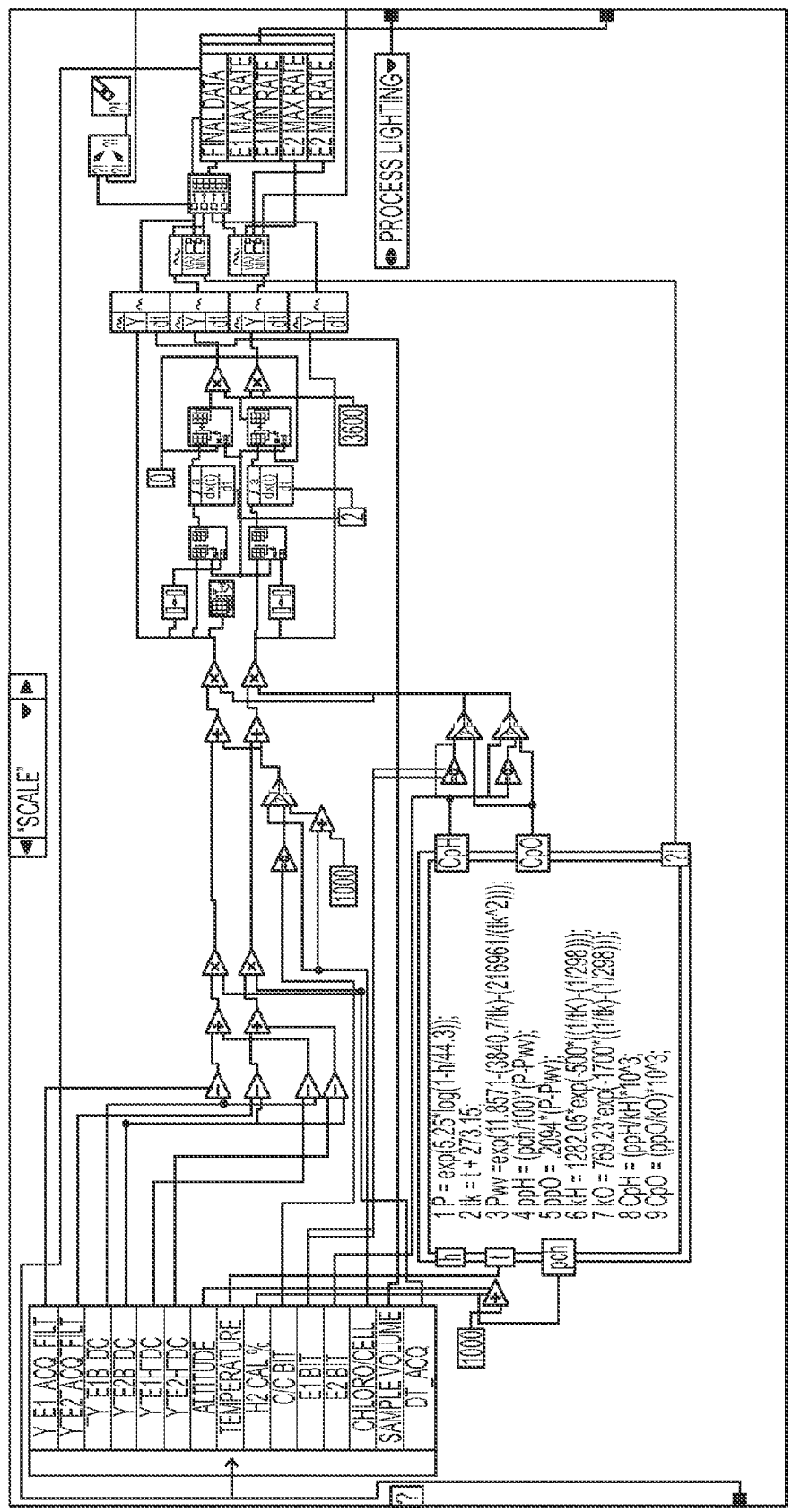
FIG. 23D depicts a "scale" state in LABVIEW® programming for an exemplary embodiment of an analysis case in an analysis state machine of the presently claimed system.
Figure 23E:
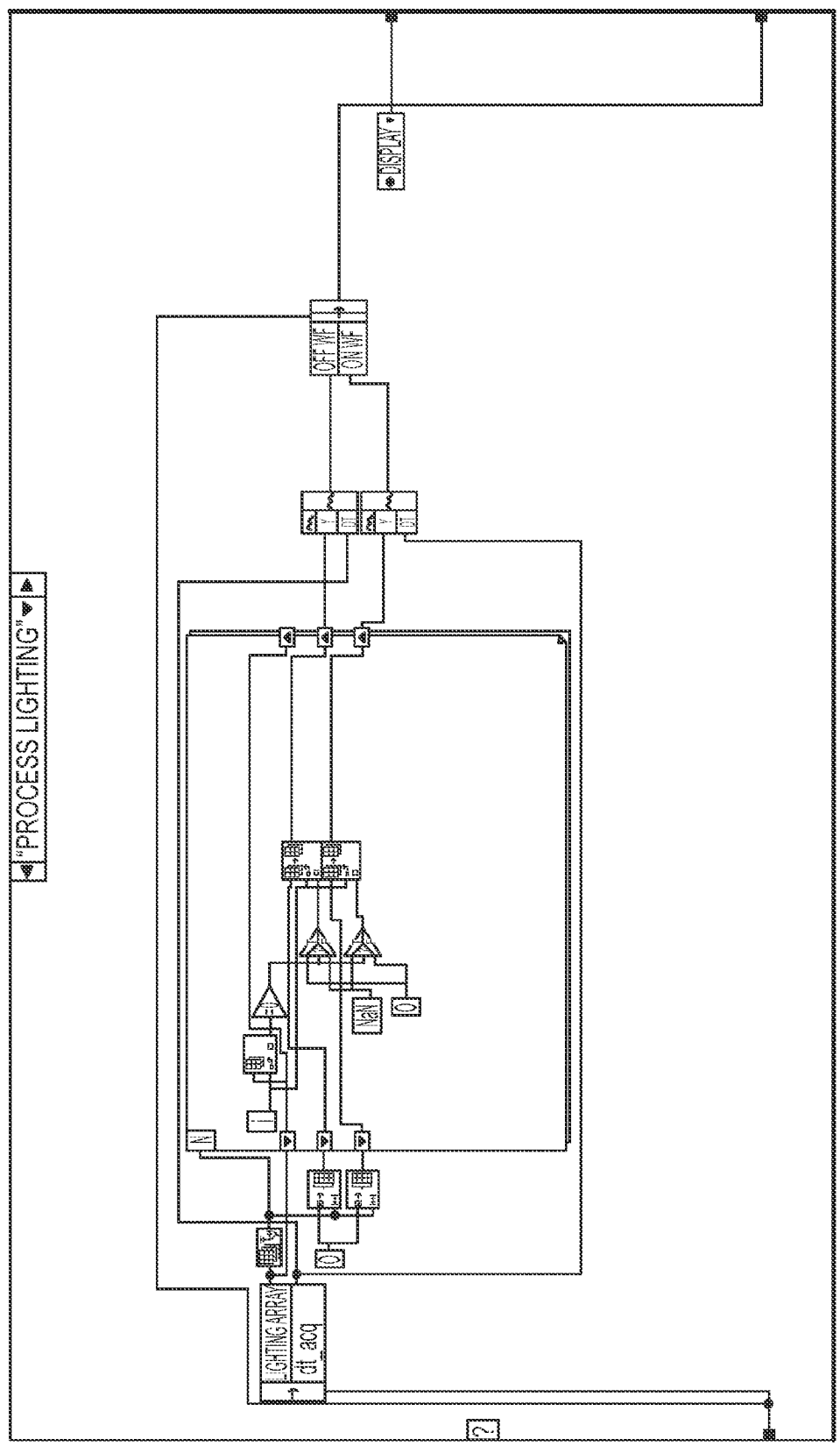
FIG. 23E depicts a "process lighting" state in LABVIEW® programming for an exemplary embodiment of an analysis case in an analysis state machine of the presently claimed system.
Figure 23F:
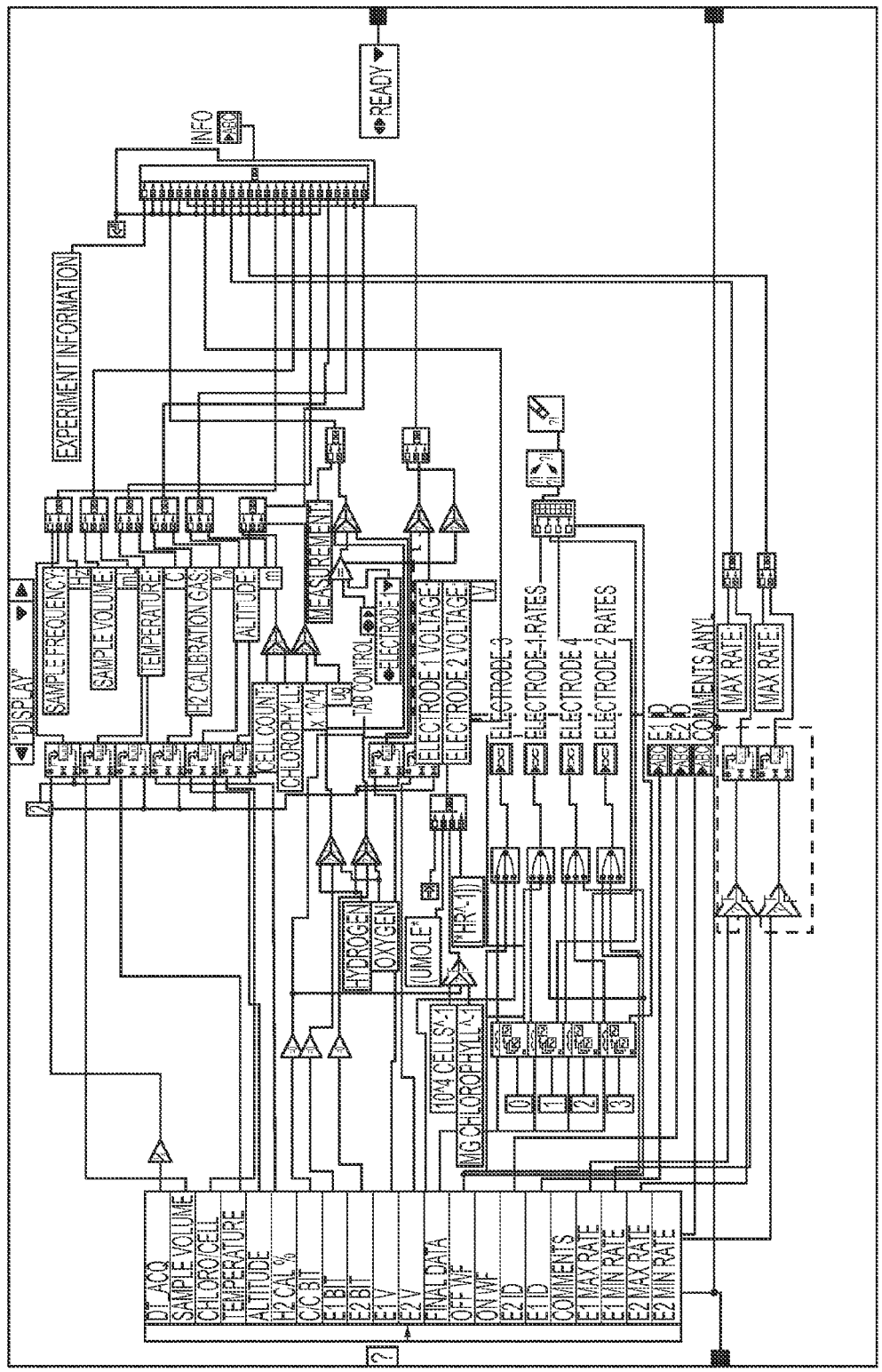
FIG. 23F depicts a "display" state in LABVIEW® programming for an exemplary embodiment of an analysis case in an analysis state machine of the presently claimed system.
Figure 23G:
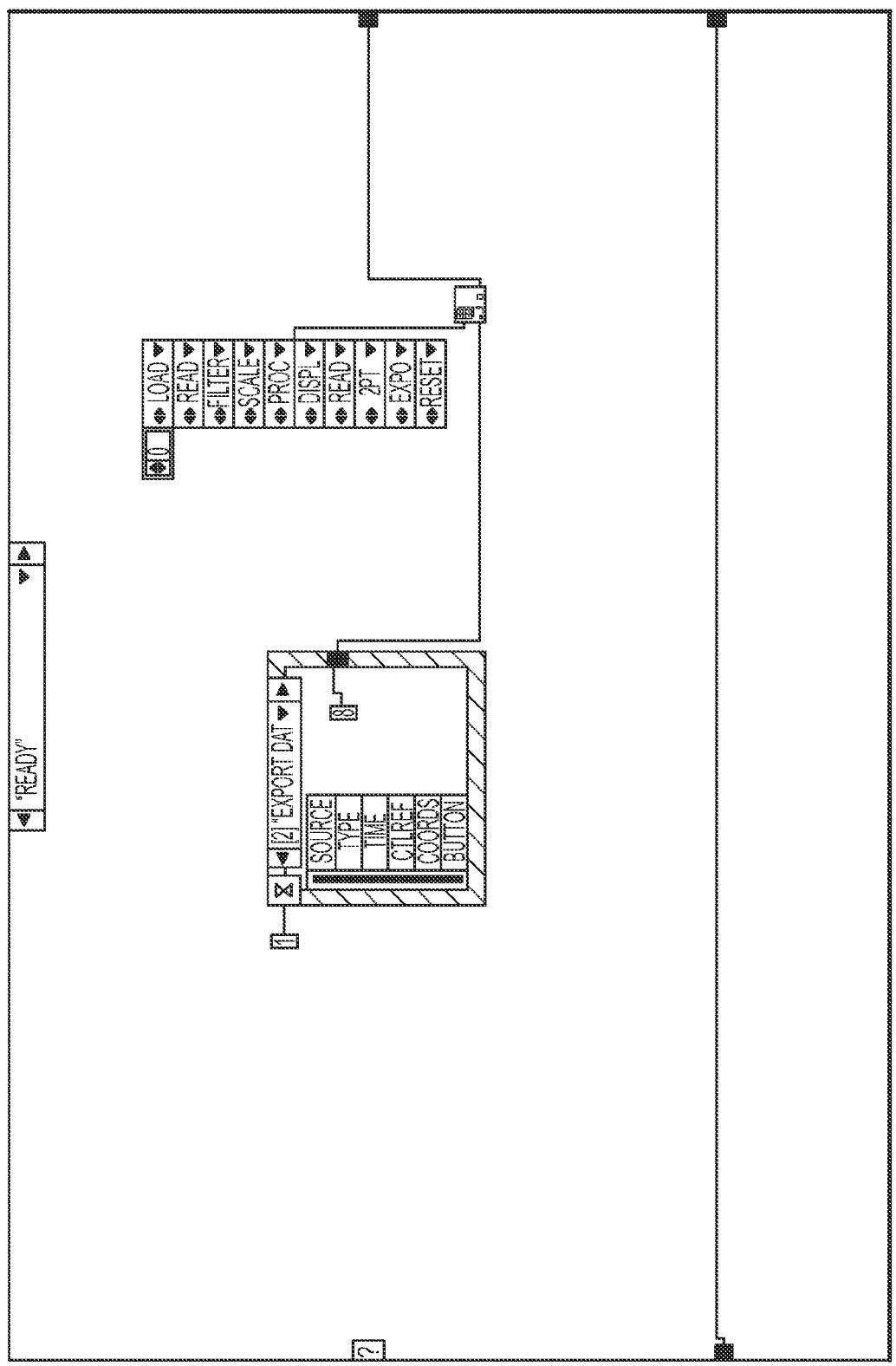
FIG. 23G depicts a "ready" state in LABVIEW® programming for an exemplary embodiment of an analysis case in an analysis state machine of the presently claimed system.
Figure 23H:
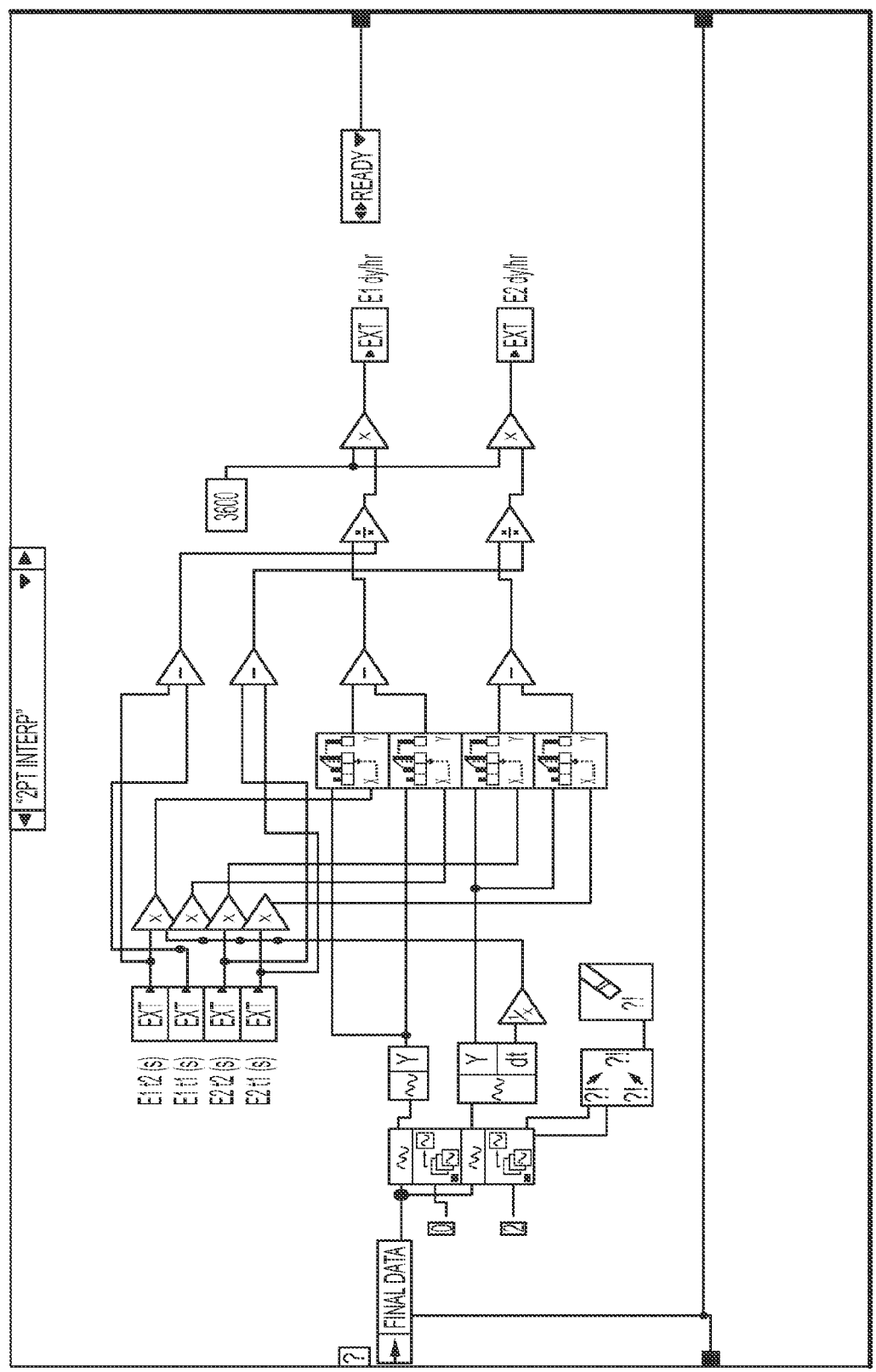
FIG. 23H depicts a "Pt interpolation" state in LABVIEW® programming for an exemplary embodiment of an analysis case in an analysis state machine of the presently claimed system.
Figure 23I:
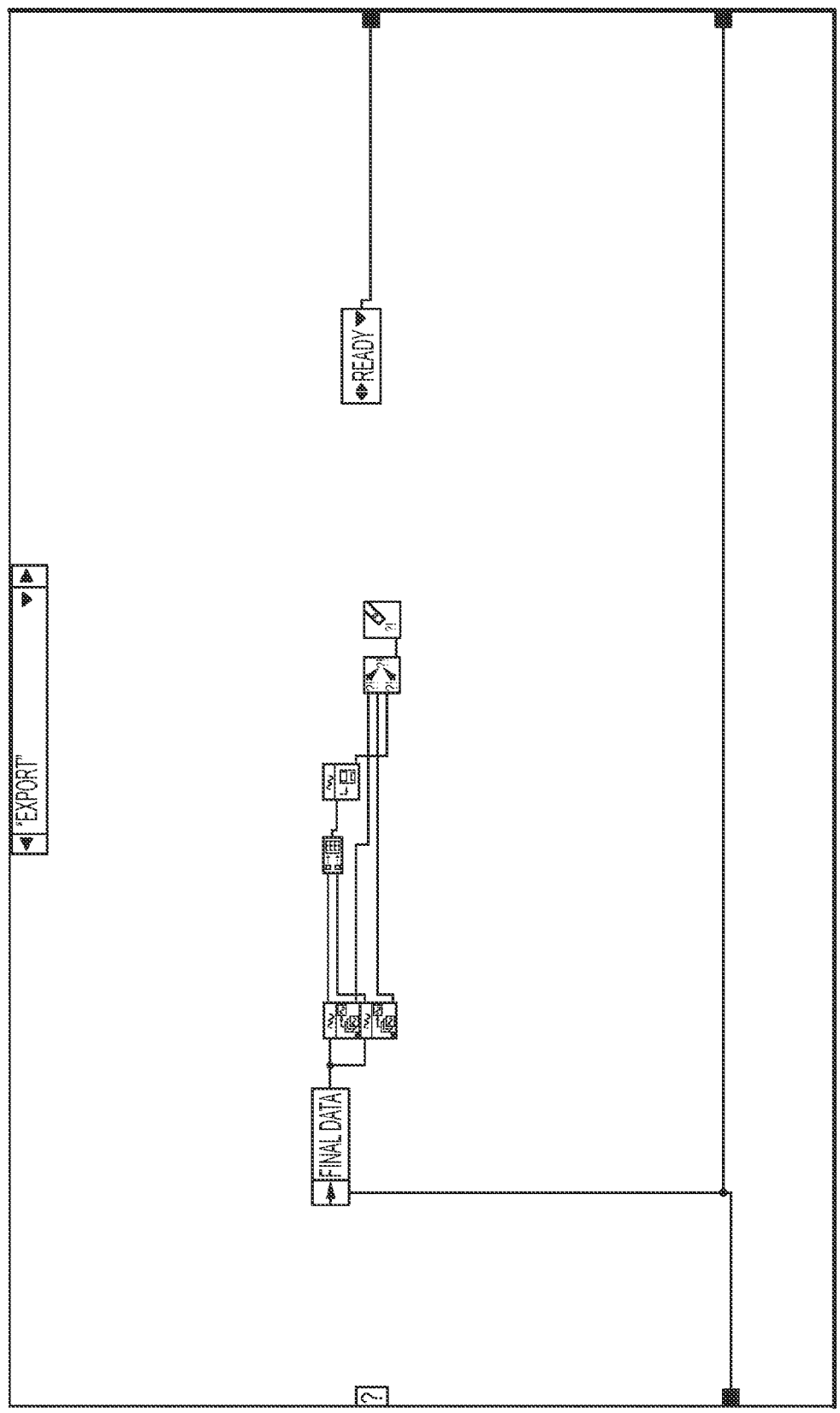
FIG. 23I depicts an "export" state in LABVIEW® programming for an exemplary embodiment of an analysis case in an analysis state machine of the presently claimed system.

FIG. 1, discussed in more detail above, depicts an embodiment of an example experimental setup for the system 100. The following circuit diagrams and programming steps were used in this example with respect to the system shown in FIG. 1. The circuits and programming steps illustrated herein may be modified in certain respects and, as such, these circuits and programming steps are provided as an example only and should not be interpreted as limiting in any way. FIGS. 8A and 8B, discussed in more detail above, illustrate an embodiment of a Circuit Wiring Diagram for use with the present system. FIG. 17 is an exemplary Circuit PCB Layout and FIG. 18 is a diagram of an exemplary Clark Polarograph Circuit for use with the present system.

FIGS. 19A-23I depict various LABVIEW® programming steps for an exemplary embodiment of the present system. For example, LABVIEW® programming steps for the Acquisition State Machine are depicted in FIGS. 20A-23H. An Analog Out Case of the Acquisition State Machine is depicted at FIGS. 19A-D, an Analog In Case is depicted at FIGS. 20A-C, a Digital Out Case is depicted at FIGS. 21A-E, and an Acquire Case is depicted at FIGS. 22A-H. An Analysis State Machine is depicted with an Analysis Case in FIGS. 23A-I.

Example Procedure

Probes were allowed to stabilize over a 2 hour period. Calibration files were taken in 1 mL, 50 mm MOPS (pH 6.9) buffer solution as follows:

$O_2$ saturation calibration: solution at atmospheric $O_2$ equilibrium.

$H_2$ saturation calibration: Ultra-high purity (UHP) 5% $H_2$:balance Ar calibration gas purging.

H₂ 0% calibration: Ar purging.

O₂ 0% calibration: Ar purging.

Argon was allowed to continue bubbling until the algal sample was ready. The following experiment was conducted by one of the inventors, following a typical procedure for quantifying H$_2$-photoproduction activity in algae. A 100 µL sample of 10× concentrated *C. reinhardtii* (strain CC124) algae was tested for H$_2$-photoproduction after 4 h of anoxia. The sample was injected into an Ar-purged 0.9 mL, 50 mm MOPS buffer (pH 6.9) solution in the sample cell. Chlorophyll content in the algal sample was determined spectrophotometrically to contain 33.65 µg chlorophyll. Temperature and altitude were entered as 25° C. and 1729 m, respectively. A 3:30 minute acquisition was taken, with manual light (1000 µmol PAR·m$^{-2}$·s$^{-1}$) Dolan-Jenner Fiber-lite, Dolan-Jenner Industries, Inc. MA, USA) activation at ~60 seconds and deactivation at ~150 seconds. 1" of 10% CuSO$_4$ solution was placed in between the light and sample to remove heat from this particular light source. The algal sample was injected at t=0 seconds and the acquisition was taken at 20 Hz in order to obtain a finely detailed profile of dissolved H$_2$ amounts, production, and uptake rates.

Results

Figure 24A:
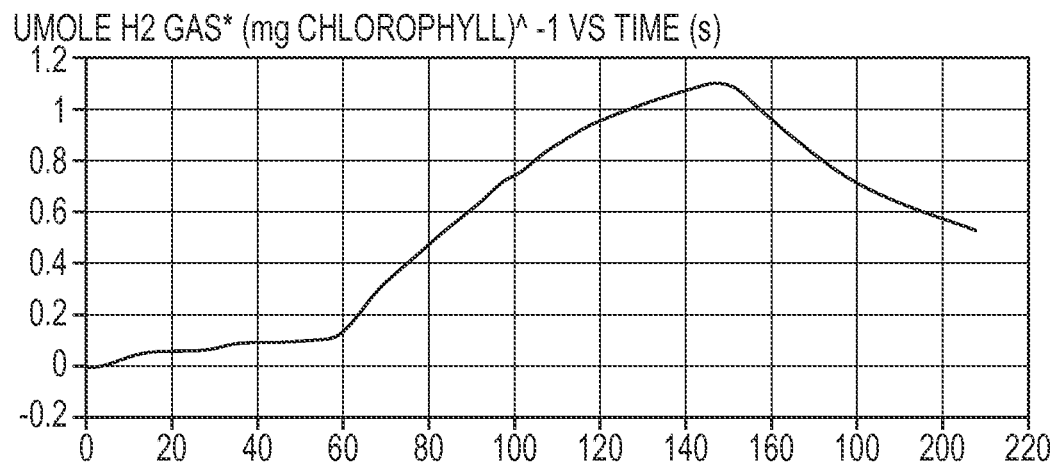
FIGS. 24A-24B depicts exemplary sample acquisition data (FIG. 24A) and rate (FIG. 24B).
Figure 24B:
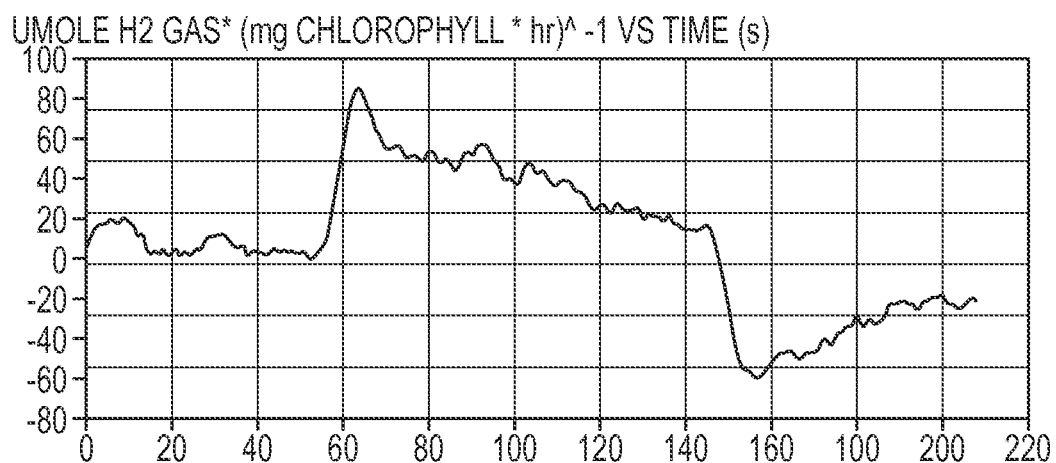

Acquired data was analyzed by software, and waveform data was exported to a separate file. FIGS. 24A-24B show exemplary sample acquisition data (FIG. 24A) and rate (FIG. 24B). As can be understood from FIG. 24A, fermentative H$_2$ production can be observed after injection until ~60 seconds as a small increase in H$_2$ gas, resulting in a total increase of 0.1 µmole H$_2$ gas*(mg chlorophyll)$^{-1}$. At that point the light was activated and an immediate increase in production rate can be seen in the hourly rate graph of FIG. 24B. Production rate remained positive, and decreased after light activation throughout the light-on period. After light deactivation at ~150 seconds, immediate H$_2$ uptake was seen throughout the rest of the acquisition. In this example, maximum instantaneous H$_2$-photoproduction activity is measured to be ~85 µmol H$_2$ gas·mg Chl$^{-1}$·hr$^{-1}$ and maximum instantaneous dark H$_2$ uptake (following illumination (i.e. oxy-hydrogen reaction, Gaffron, 1942; Posewitz et al., 2009) is measured to be ~60 µmol H$_2$ gas*(mg chlorophyll*hr)$^{-1}$. Previously measured H$_2$-photoproduction rates (Meuser J E, Ananyev G, Wittig L E, Kosourov S, Ghirardi M L, Seibert M, Dismukes G C, Posewitz M C (2009) Phenotypic diversity of hydrogen production in chlorophycean algae reflects distinct anaerobic metabolisms. J Biotechnol 142: 21-30) recorded with another custom-built Clark electrode system coincides well with this data. The current embodiment is also ideal for measurement of H$_2$ uptake in the light (i.e. CO$_2$ photoreduction, Gaffron H (1942) Reduction of carbon dioxide coupled with the oxyhydrogen reaction in algae. J Gen Physiol 26: 241-267; Posewitz M C, Dubini A, Meuser J E, Seibert M, Ghirardi M L (2009) Hydrogenases, hydrogen production and anoxia in *Chlamydomonas reinhardtii*. In: Stern D, Harris E H (eds) The *Chlamydomonas* SourceBook, Vol 2. Elsevier, 217-255).

Error Analysis

The five user-defined experimental parameters (altitude, temperature, sample volume, chlorophyll/cell count, and H$_2$ calibration gas %) were tested for translated error into the final gas calculations. A +/−10% error was independently introduced to each parameter, and a simulated signal was calculated. The following errors in calculated gas amounts were reported:

| | H$_2$ Error (+/−) | O2 Error (+/−) |
|---|---|---|
| Sample Volume | 10% | 10% |
| Temperature | 2% | 5.5% |
| Altitude | 2.1% | 2.1% |
| H$_2$ Calibration Gas % | 10% | 0% |
| Cell Count/Chlorophyll | 10% | 10% |

The 12-bit resolution of the DAQ allows a +/−14.7 mV deviation from any given voltage level in this device's configuration. This resolution does not universally translate into an error in calculated gas amounts, as calculated measurements are highly dependent upon calibration voltage levels, but can be accounted for in each measurement as:

$$\text{Error} = \left(\frac{14.7 \text{ mV}}{V_{HighCal} - V_{LowCal}}\right) * Gas_{HighCal}$$

For example, a typical value seen for O$_2$ saturation calibration is ~1.8 V, and for H$_2$ saturation calibration, ~5 V (this value will vary). Assuming:

Altitude=1729 m

Temperature=25° C.

Sample Volume=2 mL

Chlorophyll=10 µg

H$_2$Calibration Gas=5%

This translates to +/−~0.34 µmole O$_2$ gas*(mg chlorophyll)$^{-1}$ and +/−~0.018 µmole H$_2$ gas*(mg chlorophyll)$^{-1}$ error in measurements. Setting the secondary signal gain to 3 yields a smaller error in measurement, +/−~0.115 µmole O$_2$ gas*(mg chlorophyll)$^{-1}$, and +/−~0.006 µmole H$_2$ gas*(mg chlorophyll)$^{-1}$. The amount of error in each experiment is highly dependent upon the span between calibration values, thus it is important to maximize the high calibration value using secondary gain. Although error in temperature values can introduce error, it should be noted that since temperature compensation in calculating the Goff-Gratch and van 't Hoff equations is used, a greater error in probe measurement due to sample temperature change is averted.

Calibration Procedure

Calibration using other Clark electrode systems designed only for O$_2$ measurements often require probe conditioning to produce platinum black at the electrode surface. Platinum black deposition involves the periodic alternating of voltage polarization across the probe heads in order to remove layers of platinum into solution and redeposit them in a more chaotic orientation such that the effective surface area of the platinum probe head is greater. Platinum black increases the Clark electrode sensitivity to H$_2$. However, the increased sensitivity produced by this method is unstable, causing gas calibrations to quickly become invalid because of the fast decline in sensitivity. In the current disclosure, certain embodiments allow the benefits of a stable polished H$_2$ electrode allowed by a higher amplification of the H$_2$-polarized circuit than the O$_2$-polarized circuit. Calibration should be performed if:

Baselines have drifted from their original, recorded values.

Probes have become unresponsive.

Probes are being prepared with new Teflon membranes and KCl solution.

It is recommended to change and replace the Teflon membranes and KCl solutions two to three times a day to ensure maximal probe sensitivity.

Calibration Procedure:
1. Apply Teflon membrane and KCl solution.
2. Insert probe into cuvet with test solution (e.g. 50 mm MOPS solution), ensuring probe heads are entirely immersed.
3. Allow time for probe stabilization (e.g. 1-2 hrs).
4. For $O_2$ calibration:
   a. Saturation Calibration: Perform at ambient $O_2$ concentration when probe is stable (no gas bubbling).
   b. 0% Calibration: Perform with argon gas bubbling until probe is stable.
5. For $H_2$ calibration:
   a. Saturation Calibration: Perform with known $H_2$ gas concentration (5% recommended) bubbling until probe is stable.
   b. 0% Calibration: Perform with argon gas bubbling until probe is stable.
6. Bubble argon gas into solution until $O_2$ is stable at its 0% calibration level in order to prevent $O_2$ interference in algal photosystem performance.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An oxygen and hydrogen measurement system comprising:
   a polarograph system comprising:
      a signal processing and system control device; and
      a polarograph device communicatively coupled to the signal processing and system control device, the polarograph device comprising at least one probe configured to take biological $H_2$ or $O_2$ measurements, wherein a response of the at least one probe is processed based in part on feedback from environmental measurement of pressure, temperature and salinity;
   a sample system comprising:
      a sample housing for containing a photobiological, chemical, photochemical or biological redox reaction, the sample housing configured for receiving the at least one probe of the polarograph device; and
   a computing device communicatively coupled to the polarograph system, the computing device comprising:
      a processor; and
      a memory communicatively coupled to the processor, the processor configured to execute instructions stored in the memory to compute oxygen and hydrogen measurements based on information received from at least the polarograph system.

2. The system of claim 1, wherein the sample housing is environmentally-controlled and gas impermeable.

3. The system of claim 1, wherein the signal processing and system control device dynamically modifies a polarization of the at least one probe.

4. The system of claim 1, wherein the system is portable.

5. The system of claim 1, further comprising a portable power source coupled to the system.

6. The system of claim 1, further comprising an optical system operably connected to the sample system and in electrical communication with the signal processing and system control device.

7. The system of claim 1, further comprising a water temperature control system.

8. The system of claim 7, wherein the water temperature control system further comprises a fan, a heat sink, a water temperature system, and a water block.

9. The system of claim 7, wherein the water temperature control system is peltier-controlled water temperature system.

10. The system of claim 1, wherein the at least one probe is a Clark-style electrode.

11. The system of claim 1, further comprising a single housing which encloses both the signal processing and system control device, and the sample system therein.

12. The system of claim 11, wherein the housing further comprises a wall configured to separate the signal processing and system control device and the sample system while allowing the device and sample system to remain coupled.

13. The system of claim 1, wherein the computing device further comprises an input/output device communicatively coupled to the processor and communicatively coupleable to a polarographic device to receive and transmit signals therebetween, the received signals being used by the processor to compute the oxygen and hydrogen measurements and the transmitted signals being used to control lighting, temperature, pressure or other operating parameters related to the photobiological, chemical, photochemical or biological redox reaction.

14. The system of claim 1, wherein the sample system further comprises a stir plate.

15. The system of claim 1, wherein the polarograph device is configured to receive, filter and amplify signals representative of a current generated in the at least one probe coupled to the device, when the at least one probe is coupled to the sample system and exposed to a photobiological, chemical, photochemical or biological redox reaction.

16. The system of claim 15, wherein the signal processing and system control device is configured to receive the filtered and amplified signals from the polarograph device and make the signals external to the polarograph system.

17. A polarograph system comprising:
   a polarograph device comprising one or more probes and configured to receive, filter and amplify signals representative of a current generated in the one or more probes, wherein the one or more probes are coupled to a sample system and exposed to a photobiological, chemical, photochemical or biological redox reaction, wherein the one or more probes are configured to take biological $H_2$ or $O_2$ measurements, and wherein a response of the one or more probes is processed based in part on feedback from environmental measurements of pressure, temperature and salinity; and a signal processing and system control device communicatively coupled to the polarograph device and configured to receive the filtered and amplified signals and make the signals external to the polarograph system.

18. The system of claim 17, wherein the one or more probes are configured to measure hydrogen in a first mode and oxygen in a second mode.

19. The system of claim 17, wherein the system comprises two probes and the probes are oppositely polarized.

* * * * *